United States Patent
Deane et al.

(10) Patent No.: US 12,006,354 B2
(45) Date of Patent: Jun. 11, 2024

(54) ANTIBODY-IL2 ENGRAFTED PROTEINS AND METHODS OF USE IN THE TREATMENT OF CANCER

(71) Applicant: NOVARTIS AG, Basel (CH)

(72) Inventors: Jonathan Deane, San Diego, CA (US); Yaiza Diaz-De-Durana, San Diego, CA (US); Michael DiDonato, San Diego, CA (US); Christophe Filippi, Studio City, CA (US); Glen Spraggon, San Diego, CA (US)

(73) Assignee: NOVARTIS AG, Basel (CH)

( * ) Notice: Subject to any disclaimer, the term of this patent is extended or adjusted under 35 U.S.C. 154(b) by 192 days.

(21) Appl. No.: 16/616,318

(22) PCT Filed: May 22, 2018

(86) PCT No.: PCT/IB2018/053623
§ 371 (c)(1),
(2) Date: Nov. 22, 2019

(87) PCT Pub. No.: WO2018/215936
PCT Pub. Date: Nov. 29, 2018

(65) Prior Publication Data
US 2020/0270334 A1 Aug. 27, 2020

Related U.S. Application Data

(60) Provisional application No. 62/510,533, filed on May 24, 2017.

(51) Int. Cl.
| | |
|---|---|
| *C07K 14/55* | (2006.01) |
| *A61K 38/20* | (2006.01) |
| *A61K 39/395* | (2006.01) |
| *A61K 47/68* | (2017.01) |
| *A61P 35/00* | (2006.01) |
| *C07K 16/08* | (2006.01) |
| *C07K 16/10* | (2006.01) |
| *C07K 19/00* | (2006.01) |
| *C12N 5/071* | (2010.01) |
| *C12N 5/0783* | (2010.01) |
| *A61K 39/00* | (2006.01) |
| *A61K 45/06* | (2006.01) |

(52) U.S. Cl.
CPC ...... *C07K 16/1027* (2013.01); *A61K 38/2013* (2013.01); *A61K 39/3955* (2013.01); *A61K 47/6801* (2017.08); *A61P 35/00* (2018.01); *C07K 14/55* (2013.01); *C07K 19/00* (2013.01); *C12N 5/0636* (2013.01); *C12N 5/0682* (2013.01); *A61K 2039/505* (2013.01); *A61K 45/06* (2013.01); *C07K 2317/56* (2013.01); *C07K 2317/565* (2013.01); *C07K 2317/94* (2013.01); *C07K 2319/30* (2013.01)

(58) Field of Classification Search
CPC .. C07K 14/55; C07K 19/00; C07K 2317/565; C07K 16/1027; A61K 38/2013; A61K 39/3955; A61P 35/00
See application file for complete search history.

(56) References Cited

U.S. PATENT DOCUMENTS

| | | | |
|---|---|---|---|
| 5,061,488 A | 10/1991 | Wiltrout et al. | |
| 5,126,129 A | 6/1992 | Wiltrout et al. | |
| 5,126,132 A | 6/1992 | Rosenberg | |
| 5,229,109 A * | 7/1993 | Grimm | C07K 14/55 424/85.2 |
| 6,013,659 A | 1/2000 | Goldfarb et al. | |
| 7,943,743 B2 | 5/2011 | Korman et al. | |
| 8,008,449 B2 | 8/2011 | Korman et al. | |
| 8,034,334 B2 | 10/2011 | Dudley et al. | |
| 8,454,960 B2 | 6/2013 | Barbas, III | |
| 9,074,185 B2 | 7/2015 | Dudley et al. | |
| 9,844,569 B2 | 12/2017 | Gros et al. | |
| 2002/0039571 A1 | 4/2002 | Falkenberg | |
| 2002/0193371 A1 | 12/2002 | Telerman et al. | |
| 2003/0105294 A1 | 6/2003 | Gillies et al. | |
| 2004/0121971 A1 | 6/2004 | Chen et al. | |
| 2005/0106717 A1 | 5/2005 | Wilson et al. | |
| 2005/0191239 A1 | 9/2005 | Griffiths et al. | |
| 2006/0084123 A1 | 4/2006 | Harris et al. | |
| 2008/0221551 A1 | 9/2008 | Goodson et al. | |
| 2009/0274647 A1 | 11/2009 | Montero Casimiro et al. | |

(Continued)

FOREIGN PATENT DOCUMENTS

| | | |
|---|---|---|
| CN | 1721533 A | 1/2006 |
| EP | 0267615 A2 | 5/1988 |

(Continued)

OTHER PUBLICATIONS

Tam et al., 2017. Antibodies. 6(12): 1-34.*

(Continued)

*Primary Examiner* — Zachary C Howard
(74) *Attorney, Agent, or Firm* — Morgan, Lewis & Bockius LLP

(57) ABSTRACT

The present disclosure provides for IL2 engrafted into the CDR sequences of an antibody having preferred therapeutic profiles over molecules known and used in the clinic. In particular, the provided antibody cytokine engrafted protein compositions increase or maintain CD8+ T effector cells while reducing the activity of Treg cells. Additionally, provided compositions convey improved half-life, stability and producibility over recombinant human IL2 formulations such as Proleukin®.

27 Claims, 14 Drawing Sheets

Specification includes a Sequence Listing.

(56) References Cited

U.S. PATENT DOCUMENTS

| | | | |
|---|---|---|---|
| 2011/0052530 A1 | 3/2011 | Dudley et al. | |
| 2011/0136228 A1 | 6/2011 | Vera et al. | |
| 2012/0201750 A1 | 8/2012 | Ryu | |
| 2012/0244133 A1 | 9/2012 | Rosenberg et al. | |
| 2013/0102075 A1 | 4/2013 | Vera et al. | |
| 2013/0115617 A1 | 5/2013 | Wilson | |
| 2014/0127200 A1 | 5/2014 | Barbas, III | |
| 2014/0377739 A1 | 12/2014 | Welch et al. | |
| 2015/0011431 A1* | 1/2015 | Smider | C07K 16/1081 |
| | | | 506/17 |
| 2015/0023915 A1 | 1/2015 | Morrison et al. | |
| 2015/0175966 A1 | 6/2015 | Vera et al. | |
| 2016/0010058 A1 | 1/2016 | Gros et al. | |
| 2016/0208216 A1 | 7/2016 | Vera et al. | |
| 2016/0215262 A1 | 7/2016 | Powell | |
| 2017/0044496 A1 | 2/2017 | Sarnaik et al. | |
| 2017/0081635 A1 | 3/2017 | Sarnaik et al. | |
| 2017/0107490 A1 | 4/2017 | Maeurer | |
| 2017/0152478 A1 | 6/2017 | Rosenberg et al. | |

FOREIGN PATENT DOCUMENTS

| | | |
|---|---|---|
| EP | 0248516 B1 | 7/1991 |
| EP | 0241242 B1 | 3/1992 |
| EP | 0211769 B1 | 4/1992 |
| EP | 1043025 B1 | 6/2005 |
| EP | 1640018 A1 | 3/2006 |
| EP | 1688146 B1 | 7/2007 |
| EP | 2050458 A1 | 4/2009 |
| EP | 2272513 A1 | 1/2011 |
| RU | 2312677 C9 | 3/2008 |
| RU | 2484845 C2 | 6/2013 |
| WO | WO89/02746 A1 | 4/1989 |
| WO | WO89/09062 A1 | 10/1989 |
| WO | WO93/20829 A1 | 10/1993 |
| WO | WO94/04196 A1 | 3/1994 |
| WO | WO95/07995 A2 | 3/1995 |
| WO | WO95/29193 A2 | 11/1995 |
| WO | WO1996/018412 A1 | 12/1995 |
| WO | WO96/40176 A1 | 12/1996 |
| WO | WO97/10002 A1 | 3/1997 |
| WO | WO97/31622 A1 | 9/1997 |
| WO | WO97/42217 A1 | 11/1997 |
| WO | WO99/26663 A2 | 6/1999 |
| WO | WO1999/043713 A1 | 9/1999 |
| WO | WO1999/60128 A1 | 11/1999 |
| WO | WO99/61085 A2 | 12/1999 |
| WO | WO00/04048 A1 | 1/2000 |
| WO | WO00/47228 A1 | 8/2000 |
| WO | WO00/50080 A1 | 8/2000 |
| WO | WO2000047228 A1 | 8/2000 |
| WO | WO00/59515 A1 | 10/2000 |
| WO | WO2001010912 A1 | 2/2001 |
| WO | WO01/14424 A2 | 3/2001 |
| WO | WO01/52874 A2 | 7/2001 |
| WO | WO2001/79258 A1 | 10/2001 |
| WO | WO0174847 A2 | 10/2001 |
| WO | WO01/97843 A2 | 12/2001 |
| WO | WO2002/044197 A2 | 6/2002 |
| WO | WO2002/046238 A2 | 6/2002 |
| WO | WO02/053176 A2 | 7/2002 |
| WO | WO2002066514 A2 | 8/2002 |
| WO | WO2002072605 A2 | 9/2002 |
| WO | WO2002090566 A2 | 11/2002 |
| WO | WO02/097044 A2 | 12/2002 |
| WO | WO03/015697 A2 | 2/2003 |
| WO | WO04/080445 A1 | 3/2003 |
| WO | WO 2003/048334 A2 | 6/2003 |
| WO | WO2003048334 A2 | 6/2003 |
| WO | WO03/082212 A2 | 10/2003 |
| WO | WO2003/085086 A2 | 10/2003 |
| WO | WO03/097040 A1 | 11/2003 |
| WO | WO04/002526 A1 | 1/2004 |
| WO | WO04/20468 A2 | 3/2004 |
| WO | WO04/021995 A2 | 3/2004 |
| WO | WO04/022747 A1 | 3/2004 |
| WO | WO04/056392 A1 | 7/2004 |
| WO | WO2004/050017 A2 | 7/2004 |
| WO | WO04/098529 A2 | 11/2004 |
| WO | WO2004/108078 A2 | 12/2004 |
| WO | WO2005/000266 A2 | 1/2005 |
| WO | WO2005/007121 A2 | 1/2005 |
| WO | WO2005016969 A2 | 2/2005 |
| WO | WO05/044855 A2 | 5/2005 |
| WO | WO2005/060642 A2 | 7/2005 |
| WO | WO2005063820 A2 | 7/2005 |
| WO | 2005087797 A1 | 9/2005 |
| WO | WO05/082368 A1 | 9/2005 |
| WO | WO06/033766 A2 | 3/2006 |
| WO | WO2006/042237 A2 | 4/2006 |
| WO | 2006/050166 | 5/2006 |
| WO | WO2006061219 A2 | 6/2006 |
| WO | WO06/089150 A2 | 8/2006 |
| WO | WO06/089230 A2 | 8/2006 |
| WO | WO2006081510 A2 | 8/2006 |
| WO | WO06/093666 A2 | 9/2006 |
| WO | WO06/093677 A1 | 9/2006 |
| WO | WO06/112869 A2 | 10/2006 |
| WO | WO06/122431 A1 | 11/2006 |
| WO | WO07/002222 A2 | 1/2007 |
| WO | WO07/030668 A2 | 3/2007 |
| WO | WO07/038428 A2 | 4/2007 |
| WO | WO07/051119 A1 | 5/2007 |
| WO | WO07/103009 A2 | 9/2007 |
| WO | WO08/003473 A2 | 1/2008 |
| WO | WO08/042814 A2 | 4/2008 |
| WO | WO08/051220 A1 | 5/2008 |
| WO | WO08/112509 A1 | 9/2008 |
| WO | WO2008/109953 A1 | 9/2008 |
| WO | WO08/146167 A2 | 12/2008 |
| WO | WO09/046205 A1 | 4/2009 |
| WO | WO2009/088805 A2 | 7/2009 |
| WO | WO09/152610 A1 | 12/2009 |
| WO | WO10/020766 A2 | 2/2010 |
| WO | WO10/042765 A1 | 4/2010 |
| WO | WO10/081172 A1 | 7/2010 |
| WO | WO2010/099019 A1 | 9/2010 |
| WO | WO10/132867 A1 | 11/2010 |
| WO | WO11/005380 A2 | 1/2011 |
| WO | WO2011/020783 A2 | 2/2011 |
| WO | WO11/031865 A1 | 3/2011 |
| WO | WO11/066521 A1 | 6/2011 |
| WO | WO11/090492 A1 | 7/2011 |
| WO | WO11/139738 A2 | 11/2011 |
| WO | WO2012/009705 | 1/2012 |
| WO | WO2012/021609 A2 | 2/2012 |
| WO | WO12/037551 A2 | 3/2012 |
| WO | WO2012/045334 A1 | 4/2012 |
| WO | WO2012/062228 A2 | 5/2012 |
| WO | WO2012/107416 A2 | 8/2012 |
| WO | WO2012/107417 A1 | 8/2012 |
| WO | WO2012/146628 A1 | 11/2012 |
| WO | WO12/178137 A1 | 12/2012 |
| WO | WO2013/044169 A1 | 3/2013 |
| WO | WO13/056240 A1 | 4/2013 |
| WO | WO2013/045125 A2 | 4/2013 |
| WO | WO 2013/057500 A1 | 4/2013 |
| WO | WO 2013/088147 A1 | 6/2013 |
| WO | WO 2013/106485 A2 | 7/2013 |
| WO | WO2013/106485 A2 | 7/2013 |
| WO | WO2013/106489 A1 | 7/2013 |
| WO | WO13/116781 A1 | 8/2013 |
| WO | WO2013/148337 A1 | 10/2013 |
| WO | WO13/169386 A1 | 11/2013 |
| WO | WO 2013/173835 A1 | 11/2013 |
| WO | WO2013/177187 A1 | 11/2013 |
| WO | WO 2013/188427 A1 | 12/2013 |
| WO | WO2014/023673 A1 | 2/2014 |
| WO | WO2014/023679 A1 | 2/2014 |
| WO | WO2014/023752 A1 | 2/2014 |
| WO | WO14/078272 A1 | 5/2014 |
| WO | WO2014/110368 A1 | 7/2014 |
| WO | WO14/152122 A2 | 9/2014 |

(56) References Cited

FOREIGN PATENT DOCUMENTS

| | | |
|---|---|---|
| WO | WO2014/138725 A1 | 9/2014 |
| WO | WO14/201378 A1 | 12/2014 |
| WO | WO2015/006736 A2 | 1/2015 |
| WO | WO2015/006744 A1 | 1/2015 |
| WO | WO2015/010100 A2 | 1/2015 |
| WO | WO2015/017146 A2 | 2/2015 |
| WO | 2015118016 A1 | 8/2015 |
| WO | WO2015/117930 A1 | 8/2015 |
| WO | WO2015/118016 A1 | 8/2015 |
| WO | WO15/134577 A1 | 9/2015 |
| WO | WO15/140150 A1 | 9/2015 |
| WO | WO15/140172 A1 | 9/2015 |
| WO | WO 2015/189357 A1 | 12/2015 |
| WO | WO16/025642 A1 | 2/2016 |
| WO | WO2016/025647 A1 | 2/2016 |
| WO | WO2016025645 A1 | 2/2016 |
| WO | WO2016/030350 A1 | 3/2016 |
| WO | WO 2016/053338 A1 | 4/2016 |
| WO | WO16/070051 A2 | 5/2016 |
| WO | WO16/075440 A1 | 5/2016 |
| WO | WO 2016/096903 A1 | 6/2016 |
| WO | WO2017/093947 A1 | 6/2017 |
| WO | WO2017/118761 A1 | 7/2017 |
| WO | WO 2018/081473 A1 | 5/2018 |

OTHER PUBLICATIONS

Tokuriki et al., 2009, Current Opinion in Structural Biology. 19: 596-604.*

Bhattacharya et al., 2017. Plos One. 12(3): e0171355, pp. 1-22 as printed.*

Rudikoff et al (1982. Proc Natl Acad Sci USA. 79: 1979-1983).*

Zhang, et al., "Functional Antibody CDR3 fusion Proteins with Enhanced Pharmacological Properties", Angewandte Chemie International Edition, Aug. 5, 2013, pp. 8295-8298, vol. 52, No. 32, Wiley-VCH Verlag GmbH & Co. KGaA, Weinheim.

Zhang, et al., "An Antibody CDR3-Erythropoietin Fusion Protein", ACS Chemical Biology, Oct. 18, 2013, pp. 2117-2121, vol. 8, No. 10, American Chemical Society.

Liu, et al., "Rational Design of CXCR4 Specific Antibodies with Elongated CDRs", Journal of the American Chemical Society, Jul. 30, 2014, pp. 10557-10560, vol. 136, No. 30, American Chemical Society.

Liu, et al., "Functional human antibody CDR fusions as long-activing therapeutic endocrine agonists", Proceedings of the National Academy of Sciences, Jan. 20, 2015, pp. 1356-1361, vol. 112, No. 5.

Wang, et al., "Reshaping Antibody Diversity", Cell, Jun. 6, 2013, pp. 1379-1393, vol. 153, Elsevier Inc.

Zhang, et al., "Rational Design of Humanized Dual-Agonist Antibodies", Journal of the American Chemical Society, 2015, pp. 38-41, vol. 137, American Chemical Society.

Sauve, et al., "Localization in human interleukin 2 of the binding site to the alpha chain (p55) of the interleukin 2 receptor", Proc. Natl. Acad. Sci. USA, Jun. 1991, pp. 4636-4640, vol. 88.

Rosenberg, et al., "Observations on the systemic administration of autologous lymphokine-activated killer cells and recombinant interleukin-2 to patients with metastatic cancer", The New England Journal of Medicine, Dec. 5, 1985, pp. 1485-1492, DOI: 10.1056/NEJM198512053132327.

Translation of Search Report dated Sep. 30, 2021 for Russian Application No. 2019142479, 4 pages.

Kontermann R. E. et al., Bispecific antibodies, Drug Discovery Today, 2015, V. 7, N. 20, p. 838-847.

Acchione M. et al., Impact of linker and conjugation chemistry on antigen binding, Fc receptor binding and thermal stability of model antibody-drug conjugates, MAbs, 2012, V. 4, N. 3, p. 362-372.

Torres M. et al., The immunoglobulin constant region contributes to affinity and specificity, Trends in immunology, 2008, V. 29, N. 2, p. 91-97.

Tokuriki N. et al., Stability effects of mutations and protein evolvability, Curr. Opin. Struct. Biol., 2009, v.19, n.5, p. 596-604.

Rudikoff S. et al., Single amino acid substitution altering antigen-binding specificity, Proc Natl Acad Sci USA, 1982, v.79, n.6, p. 1979-1983.

Halin C. et al., Synergistic therapeutic effects of a tumor targeting antibody fragment, fused to interleukin 12 and to tumor necrosis factor alpha, Cancer Research, 2003, v. 63, n. 12, p. 3202-3210.

Frankel A.E. et al., Characterization of diphtheria fusion proteins targeted to the human interleukin-3 receptor, Protein Eng., 2000, v.13, n.8, p. 575-581.

Arnau J. et al., Current strategies for the use of affinity tags and tag removal for the purification of recombinant proteins, Protein expression and purification, 2006, V. 48, N. 1, p. 1-13.

Chen X. et al., Fusion protein linkers: property, design and functionality, Advanced drug delivery reviews, 2013, v. 65, n. 10, p. 1357-1369.

Maeda Y. et al., Engineering of functional chimeric protein G-Vargula Luciferase, Analytical biochemistry, 1997, v. 249, n. 2, p. 147-152.

Berry M. J. et al., Substitution of cysteine for selenocysteine in type I iodothyronine deiodinase reduces the catalytic efficiency of the protein but enhances its translation, Endocrinology, 1992, V. 131, N. 4, p. 1848-1852.

Gasser B. et al., Antibody production with yeasts and filamentous fungi: on the road to large scale?, Biotechnology letters, 2007, V. 29, N. 2, p. 201-212.

Burns W. R. et al., A high molecular weight melanoma-associated antigen-specific chimeric antigen receptor redirects lymphocytes to target human melanomas, Cancer research, 2010, V. 70, N. 8, p. 3027-3033.

Muller S. et al., Spliceosomal peptide P140 for immunotherapy of systemic lupus erythematosus: results of an early phase II clinical trial, Arthritis & Rheumatism: Official Journal of the American College of Rheumatology, 2008, V. 58, N. 12, p. 3873-3883.

Office Action dated Aug. 13, 2021 for Colombian Patent Application No. NC2019/0013001, 8 pages.

Examination Report No. 1 dated Oct. 12, 2020 for Australian Patent Application No. 2018274216, 5 pages.

Dario et al., "Immunocytokines for cancer treatment: past, present and future", Current Opinion in Immunology, Elsevier, Oxford, GB, vol. 40, Apr. 6, 2016, pp. 96-102, XP029551352, ISSN: 0952-7915, DOI: 10.1016/J.COI.2016.03.006.

Arenas-Ramirez et al., "Interleukin-2: Biology, Design and Application", Trends in Immunology, Elsevier Ltd. Trends Journals, GB, vol. 36, No. 12, Nov. 10, 2015, pp. 763-777, XP029348694, ISSN: 1471-4906, DOI: 10.1016/J.IT.2015.10.003.

Wang et al., "Structure of the Quarternary Complex of Interleukin-2 with Its α, β, γ c Receptors", Science, vol. 310, No. 5751, Nov. 18, 2005, pp. 1159-1163, XP055493897, ISSN: 0036-8075, DOI: 10.1126/science.1117893.

Rickert et al., "The Structure of Interleukin-2 Complexed with Its Alpha Receptor", Science, vol. 308, No. 5727, Jun. 3, 2005, pp. 1477-1480, XP055494089, ISSN: 0036-8075, DOI: 10.1126/science.1107627.

International Search Report issued for PCT/IB2018/053623, dated Jul. 31, 2018.

Besser et al., "Minimally Cultured or Selected Autologous Tumor-infiltrating Lymphocytes After a Lympho-depleting Chemotherapy Regimen in Metastatic Melanoma Patients"; J Immunother 32, 415-423 (2009).

Besser, et al., "Adoptive Transfer of Tumor-Infiltrating Lymphocytes inPatients with Metastatic Melanoma: Intent-to-Treat Analysis and Efficacy after Failure to Prior Immunotherapies"; Clin Cancer Res, 19(17):0F1-0F9 (2013).

Donia M, et al., Simplified protocol for clinical-grade tumor-infiltrating lymphocyte manufacturing with use of the Wave bioreactor. Cytotherapy. 2014;16(8):1117-20.

Donia, et al., "Characterization and Comparison of 'Standard' and 'Young' Tumour-Infiltrating Lymphocytes for Adoptive Cell Therapy at a Danish Translational Research Institution"; Scandinavian Journal of Immunology, 75, 157-157 (2012).

Dudley et al., "Adoptive Cell Transfer Following Non-Myeloablative but Lymphodepleting Chemotherapy for the Treat-

(56) References Cited

OTHER PUBLICATIONS ment of Patients with Refractory Metastatic Melanoma", J. Clin. Oncol. Apr. 2005, 23(10), 2346-57.

Dudley et al., "Generation of Tumor-Infiltrating Lymphocyte Cultures for Use in Adoptive Transfer Therapy for Melanoma Patients," J Immunother., 2003: 26(4): 332-342.

Dudley, et al.,"Cancer Regression and Autoimmunity in Patients After Clonal Repopulation with Antitumor Lymphocytes", Science, Oct. 2002, 298, 850-54.

International Search Report and Written Opinion for International Patent Application No. PCT/US2018/012633 dated May 25, 2018, 14 pages.

He et al., "Ex vivo expansion of tumor-infiltrating lymphocytes from nasopharyngeal carcinoma patients for adoptive immunotherapy," Chinese Journal of Cancer, vol. 31, No. 6, Jun. 5, 2012.

Jin et al., "Simplified method of the growth of human tumor infiltrating lymphocytes in gas-permeable flasks to numbers needed for patient treatment", J. Immunotherapy, 2012, 35:283-292.

Li et al. MART-1-specific melanoma tumor-infiltrating lymphocytes maintaining CD28 expression have improved survival and expansion capability following antigenic restimulation in vitro. J Immunol. Jan. 1, 2010;184(1):452-65.

Robbins, et al., "Cutting Edge: Persistence of Transferred Lymphocyte Clonotypes Correlates with Cancer Regression in Patients Receiving Cell Transfer Therapy"; J. Immunol 2004; 173, 7125-7130.

Rosenberg SA, Dudley ME. "Adoptive cell therapy for the treatment of patients with metastatic melanoma", Curr Opin Immunol. 2009;21(2):233-40.

Rosenberg, "IL-2: The First Effective Immunotherapy for Human Cancer," The Journal of Immunology, col. 192, No. 12, Jun. 6, 2014.

Sadeghi, et al., "Rapid expansion of T cells: Effects of culture and cryopreservation and importance of short-term cell recovery", Acta Oncologica 2013, 52, 978-986.

Somerville RP, et al., "Clinical scale rapid expansion of lymphocytes for adoptive cell transfer therapy in the Wave® bioreactor", J Transl Med. Apr. 4, 2012;10:69.

Tran et al., "Minimally Cultured tumor-infiltrating lymphocytes display optimal characteristics for adoptive cell therapy", J. Immunother., Oct. 2008; 31(8), 742-751.

Ye, Q. et al.; "Engineered artificial antigen presenting cells facilitate direct and efficient expansion of tumor infiltrating lymphocytes", Journal of Translational Medicine 2011, 9:131.

Kratchmarova I. et al. Mechanism of Divergent Growth Factor Effects in Mesenchymal Stem Cell Differentiation / Irina Kratchmarova, Blagoy Blagoev, Mandana Haack-Sorensen, Moustapha Kassem and Matthias Mann// Science.—2005.—vol. 308.—No. 5727.—p. 1472-1477.

Office Action dated Apr. 2, 2021 for Chilean Patent Application No. 201903390, 16 pages.

Neri D., et al. Current Opinion in Immunology. 40: 96-102.

Search Report dated Mar. 31, 2021 for Singapore Patent Application No. 11201910629Y, 2 pages.

* cited by examiner

Figure 1

Protein Engineering to Modulate IL2-R Selectivity

| Name | Yield (mg/L) | Aggreg. (%) | Tm | LAL (EU/mg) | Format | Treg (fold expan.) | NK (fold expan.) | CD8 Teff (fold expan.) | IL-2Rαβγ ($EC_{50}$ vs. IL-2) | IL-2Rβγ ($EC_{50}$ vs. IL-2) |
|---|---|---|---|---|---|---|---|---|---|---|
| rhIL-2 (Proleukin) | N/A | N/A | N/A | N/A | Non-grafted | 1.5 | 2.4 | 1.9 | 1 | 1 |
| IgG.IL2R67A.H1 | 5.6 | 0.01 | 70.9/73.2 | 0.85 | R38A in H1 | 1.5 | 1 | 3.6 | 0.03 | 90 |
| IgG.IL2F71A.H1 | 8.9 | 1.6 | 70.6/72.9 | 0.16 | F42A in H1 | 1.5 | 0.6 | 6.6 | 8 | 2 |
| GFTX3b-IL2-H1 | 9.6 | 1.8 | 68.6 | 0.95 | H1 | 1.5 | 0.8 | 2.1 | 1 | 0.3 |
| GFTX3b-IL2-H2 | 6.6 | 1.6 | 67.4 | 0.76 | H2 | 0.9 | 0.9 | 2.2 | 6 | 1 |
| GFTX3b-IL2-H3 | 6.8 | 2.3 | 67 | 0.96 | H3 | 1.1 | 1.2 | 1.3 | 250 | 3400 |
| GFTX3b-IL2-L1 | 3.4 | 1.9 | 63.7/76.5 | 1.04 | L1 | 0.9 | 0.5 | 2 | 1 | 0.5 |
| GFTX3b-IL2-L2 | - | - | - | - | L2 | - | - | - | - | - |
| GFTX3b-IL2-L3 | 3.6 | 3.6 | 69.3 | 0.98 | L3 | 1.5 | 0.7 | 4.1 | 4 | 4 |

IgG.IL2R67A.H1 has extended half-life compared to Proleukin® (IL-2)

IgG.IL2R67A.H1/IL-2Fc 100ug (~1nmol of IL-2 equivalent) 4.3mg per kg in 1 dose given on day 1
Proleukin 3.41 ug (1nmol of IL-2) 0.14mg per kg in 5 consecutive daily doses/week IgG.IL2R67A.H1/IL-2Fc 100ug (~1nmol of IL-2 equivalent) 4.3mg per kg in 1 dose given on day 1
Proleukin 3.41 ug (1nmol of IL-2) 0.14mg per kg in 5 consecutive daily doses/week IgG.IL2R67A.H1/IL-2Fc 100ug (~1nmol of IL-2 equivalent) 4.3mg per kg in 1 dose given on day 1
Proleukin 3.41 ug (1nmol of IL-2) 0.14mg per kg in 5 consecutive daily doses/week IgG.IL2R67A.H1/IL-2Fc 500ug (5nmol) 21.7mg per kg in 1 dose given on day 1 Proleukin 17.04 ug (5nmol) 0.74mg per kg in 5 consecutive daily doses/week IgG.IL2R67A.H1/IL-2Fc 500ug (5nmol) 21.7mg per kg in 1 dose given on day 1 Proleukin 17.04 ug (5nmol) 0.74mg per kg in 5 consecutive daily doses/week IgG.IL2R67A.H1/IL-2Fc 500ug (5nmol) 21.7mg per kg in 1 dose given on day 1 Proleukin 17.04 ug (5nmol) 0.74mg per kg in 5 consecutive daily doses/week

IgG.IL2R67A.H1 selectively expands CD8 $T_{eff}$, better tolerated than Proleukin® in NOD Mice

Figure 4B

IgG.IL2R67A.H1 selectively expands CD8 $T_{eff}$, better tolerated than Proleukin® in NOD Mice

Fold cellular changes in prediabetic mice
(treatment vs. vehicle)

|  | Dose nmol IL-2 equiv per kg | IgG.IL2R67A.H1 | IgG.IL2F71A.H1 | IL-2 proleukin |
|---|---|---|---|---|
| CD8 $T_{eff}$ | 200 | 3.8 | 6.1 | 2.8 |
|  | 40 | 1.7 | 2.2 | 0.9 |
| $T_{reg}$ | 200 | 1.0 | 1.5 | 1.4 |
|  | 40 | 0.9 | 1.2 | 1.1 |
| CD4 $T_{eff}$ | 200 | 1.1 | 1.2 | 1.1 |
|  | 40 | 1.0 | 1.1 | 0.8 |
| NK | 200 | 0.4 | 0.7 | 1.2 |
|  | 40 | 0.4 | 0.6 | 0.9 |

IgG.IL2R67A.H1 shows single-agent efficacy in CT26 model

IgG.IL2R67A.H1 +/- TA99 shows efficacy in B16 model

Figure 7

Activity of IL-2 Grafts in Human Cells

| Equimolar graft/IL-2 2nM | Fold pSTAT5 | | | |
|---|---|---|---|---|
| | CD8 | NK | T$_{reg}$ | CD4 |
| Proleukin (IL-2) | 102 | 71 | 30 | 300 |
| GFTX3b_IL-2-H1 | 98 | 83 | 37 | 347 |
| IgG.IL2R67A.H1 | 71 | 64 | 24 | 234 |
| IgG.IL2F71A.H1 | 36 | 34 | 11 | 70 |
| GFTX3b_IL-2-H2 | 20 | 28 | 13 | 142 |
| GFTX3b_IL-2D113A | 4 | 12 | 15 | 118 |

SEQUENCE LISTING

```
<160> NUMBER OF SEQ ID NOS: 78

<210> SEQ ID NO 1
<211> LENGTH: 822
<212> TYPE: DNA
<213> ORGANISM: Homo sapiens

<400> SEQUENCE: 1
agttccctat cactctcttt aatcactact cacagtaacc tcaactcctg ccacaatgta      60
caggatgcaa ctcctgtctt gcattgcact aagtcttgca cttgtcacaa acagtgcacc     120
tacttcaagt tctacaaaga aaacacagct acaactggag catttactgc tggatttaca     180
gatgattttg aatggaatta ataattacaa gaatcccaaa ctcaccagga tgctcacatt     240
taagttttac atgcccaaga aggccacaga actgaaacat cttcagtgtc tagaagaaga     300
actcaaacct ctggaggaag tgctaaattt agctcaaagc aaaaactttc acttaagacc     360
cagggactta atcagcaata tcaacgtaat agttctggaa ctaaagggat ctgaaacaac     420
attcatgtgt gaatatgctg atgagacagc aaccattgta gaatttctga acagatggat     480 tacctttgt caaagcatca tctcaacact gacttgataa ttaagtgctt cccacttaaa     540
acatatcagg ccttctattt atttaaatat ttaaatttta tatttattgt tgaatgtatg     600
gtttgctacc tattgtaact attattctta atcttaaaac tataaatatg gatcttttat     660 gattctttt gtaagcccta ggggctctaa aatggtttca cttatttatc ccaaaatatt     720
tattattatg ttgaatgtta aatatagtat ctatgtagat tggttagtaa aactatttaa     780
taaatttgat aaatataaaa aaaaaaaaa aaaaaaaaaa aa                        822

<210> SEQ ID NO 2
```

<211> LENGTH: 153
<212> TYPE: PRT
<213> ORGANISM: Homo sapiens

<400> SEQUENCE: 2

```
Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150
```

<210> SEQ ID NO 3
<211> LENGTH: 759
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 3

```
caagtcacac tgcgtgaaag cggccctgcc ctggtcaagc ccacccagac cctgaccctg      60
acctgcacct tctccggctt cagcctggcc cctacctcct ccagcaccaa gaaaacccag     120
ctgcagctcg aacatctgct gctggacctg cagatgatcc tgaacggcat caacaactac     180
aagaacccca agctgacccg gatgctgacc ttcaagttct acatgcccaa gaaggccacc     240
gagctgaaac atctgcagtg cctggaagag aactgaagc cctggaagaa gtgctgaac      300
ctggcccagt ccaagaactt ccacctgagg cctcgggacc tgatctccaa catcaacgtg     360
atcgtgctgg aactgaaggg ctccgagaca accttcatgt gcgagtacgc cgacgagaca     420
gccaccatcg tggaatttct gaaccggtgg atcaccttct gccagtccat catctccacc     480
ctgacctcca cctccggcat gtccgtgggc tggatccggc agcctcctgg caaggccctg     540
gagtggctgc cgacatttg gtgggacgac aagaaggact acaaccccag cctgaagtcc     600
cggctgacca tctccaagga cacctccaag aaccaagtgg tgctgaaagt gaccaacatg     660
gaccccgccg acaccgccac ctactactgc gcccggtcca tgatcaccaa ctggtacttc     720
gacgtgtggg gcgctggcac caccgtgacc gtgtcctct                            759
```

<210> SEQ ID NO 4
<211> LENGTH: 133
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"

<400> SEQUENCE: 4
```

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Ala Met Leu Thr Phe Lys Phe Tyr Met Pro Lys
        35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
            130

```
<210> SEQ ID NO 5
<211> LENGTH: 399
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 5
```
gcccctacct cctccagcac caagaaaacc cagctgcagc tcgaacatct gctgctggac     60
ctgcagatga tcctgaacgg catcaacaac tacaagaacc ccaagctgac ccggatgctg    120
accgccaagt tctacatgcc caagaaggcc accgagctga acatctgca gtgcctggaa    180 gaggaactga agcccctgga agaagtgctg aacctggccc agtccaagaa cttccacctg    240
aggcctcggg acctgatctc caacatcaac gtgatcgtgc tggaactgaa gggctccgag    300
acaaccttca tgtgcgagta cgccgacgag acagccacca tcgtggaatt tctgaaccgg    360
tggatcacct tctgccagtc catcatctcc accctgacc                          399

```
<210> SEQ ID NO 6
<211> LENGTH: 133
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6
```

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Tyr Met Pro Lys

```
                35                  40                  45
Lys Ala Thr Glu Leu Lys His Leu Gln Cys Leu Glu Glu Leu Lys
 50                  55                  60
Pro Leu Glu Glu Val Leu Asn Leu Ala Gln Ser Lys Asn Phe His Leu
65                  70                  75                  80
Arg Pro Arg Asp Leu Ile Ser Asn Ile Asn Val Ile Val Leu Glu Leu
                85                  90                  95
Lys Gly Ser Glu Thr Thr Phe Met Cys Glu Tyr Ala Asp Glu Thr Ala
                100                 105                 110
Thr Ile Val Glu Phe Leu Asn Arg Trp Ile Thr Phe Cys Gln Ser Ile
                115                 120                 125
Ile Ser Thr Leu Thr
                130

<210> SEQ ID NO 7
<211> LENGTH: 145
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Gly Phe Ser Leu Ala Pro Thr Ser Ser Thr Lys Lys Thr Gln Leu
1               5                   10                  15

Gln Leu Glu His Leu Leu Leu Asp Leu Gln Met Ile Leu Asn Gly Ile
                20                  25                  30

Asn Asn Tyr Lys Asn Pro Lys Leu Thr Ala Met Leu Thr Phe Lys Phe
                35                  40                  45

Tyr Met Pro Lys Lys Ala Thr Glu Leu Lys His Leu Gln Cys Leu Glu
                50                  55                  60

Glu Leu Lys Pro Leu Glu Glu Val Leu Asn Leu Ala Gln Ser Lys
65                  70                  75                  80

Asn Phe His Leu Arg Pro Arg Asp Leu Ile Ser Asn Ile Asn Val Ile
                85                  90                  95

Val Leu Glu Leu Lys Gly Ser Glu Thr Thr Phe Met Cys Glu Tyr Ala
                100                 105                 110

Asp Glu Thr Ala Thr Ile Val Glu Phe Leu Asn Arg Trp Ile Thr Phe
                115                 120                 125

Cys Gln Ser Ile Ile Ser Thr Leu Thr Ser Ser Gly Met Ser Val
                130                 135                 140

Gly
145

<210> SEQ ID NO 8
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Asp Ile Trp Trp Asp Asp Lys Lys Asp Tyr Asn Pro Ser Leu Lys Ser
1               5                   10                  15

<210> SEQ ID NO 9
```

```
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Ser Met Ile Thr Asn Trp Tyr Phe Asp Val
1               5                   10

<210> SEQ ID NO 10
<211> LENGTH: 141
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Ala Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Ser Thr Ser Gly Met Ser Val Gly
    130                 135                 140

<210> SEQ ID NO 11
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Asp Ile Trp Trp Asp Asp Lys Lys Asp Tyr Asn Pro Ser Leu Lys Ser
1               5                   10                  15

<210> SEQ ID NO 12
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12
```

Ser Met Ile Thr Asn Trp Tyr Phe Asp Val
1               5                   10

<210> SEQ ID NO 13
<211> LENGTH: 142
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Gly Phe Ser Leu Ala Pro Thr Ser Ser Thr Lys Lys Thr Gln Leu
1               5                   10                  15

Gln Leu Glu His Leu Leu Leu Asp Leu Gln Met Ile Leu Asn Gly Ile
                20                  25                  30

Asn Asn Tyr Lys Asn Pro Lys Leu Thr Ala Met Leu Thr Phe Lys Phe
            35                  40                  45

Tyr Met Pro Lys Lys Ala Thr Glu Leu Lys His Leu Gln Cys Leu Glu
50                  55                  60

Glu Glu Leu Lys Pro Leu Glu Glu Val Leu Asn Leu Ala Gln Ser Lys
65                  70                  75                  80

Asn Phe His Leu Arg Pro Arg Asp Leu Ile Ser Asn Ile Asn Val Ile
                85                  90                  95

Val Leu Glu Leu Lys Gly Ser Glu Thr Thr Phe Met Cys Glu Tyr Ala
                100                 105                 110

Asp Glu Thr Ala Thr Ile Val Glu Phe Leu Asn Arg Trp Ile Thr Phe
            115                 120                 125

Cys Gln Ser Ile Ile Ser Thr Leu Thr Ser Thr Ser Gly Met
130                 135                 140

<210> SEQ ID NO 14
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Trp Trp Asp Asp Lys
1               5

<210> SEQ ID NO 15
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Ser Met Ile Thr Asn Trp Tyr Phe Asp Val
1               5                   10

<210> SEQ ID NO 16
<211> LENGTH: 143
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 16

Gly Phe Ser Leu Ala Pro Thr Ser Ser Thr Lys Lys Thr Gln Leu
1               5                   10                  15

Gln Leu Glu His Leu Leu Leu Asp Leu Gln Met Ile Leu Asn Gly Ile
            20                  25                  30

Asn Asn Tyr Lys Asn Pro Lys Leu Thr Ala Met Leu Thr Phe Lys Phe
        35                  40                  45

Tyr Met Pro Lys Lys Ala Thr Glu Leu Lys His Leu Gln Cys Leu Glu
    50                  55                  60

Glu Glu Leu Lys Pro Leu Glu Glu Val Leu Asn Leu Ala Gln Ser Lys
65                  70                  75                  80

Asn Phe His Leu Arg Pro Arg Asp Leu Ile Ser Asn Ile Asn Val Ile
                85                  90                  95

Val Leu Glu Leu Lys Gly Ser Glu Thr Thr Phe Met Cys Glu Tyr Ala
            100                 105                 110

Asp Glu Thr Ala Thr Ile Val Glu Phe Leu Asn Arg Trp Ile Thr Phe
        115                 120                 125

Cys Gln Ser Ile Ile Ser Thr Leu Thr Ser Thr Ser Gly Met Ser
    130                 135                 140

<210> SEQ ID NO 17
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 17

Ile Trp Trp Asp Asp Lys Lys
1               5

<210> SEQ ID NO 18
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 18

Ala Arg Ser Met Ile Thr Asn Trp Tyr Phe Asp Val
1               5                   10

<210> SEQ ID NO 19
<211> LENGTH: 253
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 19

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ala Pro Thr
            20                  25                  30

Ser Ser Ser Thr Lys Lys Thr Gln Leu Gln Leu Glu His Leu Leu Leu
            35                  40                  45

Asp Leu Gln Met Ile Leu Asn Gly Ile Asn Asn Tyr Lys Asn Pro Lys
 50                  55                  60

Leu Thr Ala Met Leu Thr Phe Lys Phe Tyr Met Pro Lys Lys Ala Thr
 65                  70                  75                  80

Glu Leu Lys His Leu Gln Cys Leu Glu Glu Leu Lys Pro Leu Glu
                85                  90                  95

Glu Val Leu Asn Leu Ala Gln Ser Lys Asn Phe His Leu Arg Pro Arg
                100                 105                 110

Asp Leu Ile Ser Asn Ile Asn Val Ile Val Leu Glu Leu Lys Gly Ser
            115                 120                 125

Glu Thr Thr Phe Met Cys Glu Tyr Ala Asp Glu Thr Ala Thr Ile Val
            130                 135                 140

Glu Phe Leu Asn Arg Trp Ile Thr Phe Cys Gln Ser Ile Ile Ser Thr
145                 150                 155                 160

Leu Thr Ser Thr Ser Gly Met Ser Val Gly Trp Ile Arg Gln Pro Pro
                165                 170                 175

Gly Lys Ala Leu Glu Trp Leu Ala Asp Ile Trp Asp Asp Lys Lys
            180                 185                 190

Asp Tyr Asn Pro Ser Leu Lys Ser Arg Leu Thr Ile Ser Lys Asp Thr
            195                 200                 205

Ser Lys Asn Gln Val Val Leu Lys Val Thr Asn Met Asp Pro Ala Asp
    210                 215                 220

Thr Ala Thr Tyr Tyr Cys Ala Arg Ser Met Ile Thr Asn Trp Tyr Phe
225                 230                 235                 240

Asp Val Trp Gly Ala Gly Thr Thr Val Thr Val Ser Ser
                245                 250

<210> SEQ ID NO 20
<211> LENGTH: 759
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 20
caagtcacac tgcgtgaaag cggccctgcc ctggtcaagc ccacccagac cctgaccctg      60
acctgcacct tctccggctt cagcctggcc cctacctcct ccagcaccaa gaaaacccag    120
ctgcagctcg aacatctgct gctggacctg cagatgatcc tgaacggcat caacaactac    180
aagaacccca gctgaccgc catgctgacc ttcaagttct acatgcccaa gaaggccacc    240
gagctgaaac atctgcagtg cctggaagag aactgaagc ccctggaaga agtgctgaac    300
ctggcccagt ccaagaactt ccacctgagg cctcgggacc tgatctccaa catcaacgtg    360
atcgtgctgg aactgaaggg ctccgagaca accttcatgt gcgagtacgc cgacgagaca    420
gccaccatcg tggaatttct gaaccggtgg atcaccttct gccagtccat catctccacc    480
ctgacctcca cctccggcat gtccgtgggc tggatccggc agcctcctgg caaggccctg    540
gagtggctgg ccgacatttg gtgggacgac aagaaggact acaaccccag cctgaagtcc    600
cggctgacca tctccaagga cacctccaag aaccaagtgg tgctgaaagt gaccaacatg    660
gaccccgccg acaccgccac ctactactgc gcccggtcca tgatcaccaa ctggtacttc    720
gacgtgtggg gcgctggcac caccgtgacc gtgtcctct                    759

<210> SEQ ID NO 21
<211> LENGTH: 583
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ala Pro Thr
            20                  25                  30

Ser Ser Ser Thr Lys Lys Thr Gln Leu Gln Leu Glu His Leu Leu Leu
        35                  40                  45

Asp Leu Gln Met Ile Leu Asn Gly Ile Asn Asn Tyr Lys Asn Pro Lys
    50                  55                  60

Leu Thr Ala Met Leu Thr Phe Lys Phe Tyr Met Pro Lys Lys Ala Thr
65                  70                  75                  80

Glu Leu Lys His Leu Gln Cys Leu Glu Glu Leu Lys Pro Leu Glu
                85                  90                  95

Glu Val Leu Asn Leu Ala Gln Ser Lys Asn Phe His Leu Arg Pro Arg
            100                 105                 110

Asp Leu Ile Ser Asn Ile Asn Val Ile Val Leu Glu Leu Lys Gly Ser
        115                 120                 125

Glu Thr Thr Phe Met Cys Glu Tyr Ala Asp Glu Thr Ala Thr Ile Val
130                 135                 140

Glu Phe Leu Asn Arg Trp Ile Thr Phe Cys Gln Ser Ile Ile Ser Thr
145                 150                 155                 160

Leu Thr Ser Thr Ser Gly Met Ser Val Gly Trp Ile Arg Gln Pro Pro
                165                 170                 175

Gly Lys Ala Leu Glu Trp Leu Ala Asp Ile Trp Trp Asp Asp Lys Lys
            180                 185                 190

Asp Tyr Asn Pro Ser Leu Lys Ser Arg Leu Thr Ile Ser Lys Asp Thr
        195                 200                 205

Ser Lys Asn Gln Val Val Leu Lys Val Thr Asn Met Asp Pro Ala Asp
    210                 215                 220

Thr Ala Thr Tyr Tyr Cys Ala Arg Ser Met Ile Thr Asn Trp Tyr Phe
225                 230                 235                 240

Asp Val Trp Gly Ala Gly Thr Thr Val Thr Val Ser Ser Ala Ser Thr
                245                 250                 255

Lys Gly Pro Ser Val Phe Pro Leu Ala Pro Ser Ser Lys Ser Thr Ser
            260                 265                 270

Gly Gly Thr Ala Ala Leu Gly Cys Leu Val Lys Asp Tyr Phe Pro Glu
        275                 280                 285

Pro Val Thr Val Ser Trp Asn Ser Gly Ala Leu Thr Ser Gly Val His
    290                 295                 300

Thr Phe Pro Ala Val Leu Gln Ser Ser Gly Leu Tyr Ser Leu Ser Ser
305                 310                 315                 320

Val Val Thr Val Pro Ser Ser Ser Leu Gly Thr Gln Thr Tyr Ile Cys
                325                 330                 335

Asn Val Asn His Lys Pro Ser Asn Thr Lys Val Asp Lys Arg Val Glu
            340                 345                 350

```
Pro Lys Ser Cys Asp Lys Thr His Thr Cys Pro Pro Cys Pro Ala Pro
        355                 360                 365

Glu Leu Leu Gly Gly Pro Ser Val Phe Leu Phe Pro Pro Lys Pro Lys
        370                 375                 380

Asp Thr Leu Met Ile Ser Arg Thr Pro Glu Val Thr Cys Val Val Val
385                 390                 395                 400

Ala Val Ser His Glu Asp Pro Glu Val Lys Phe Asn Trp Tyr Val Asp
                405                 410                 415

Gly Val Glu Val His Asn Ala Lys Thr Lys Pro Arg Glu Glu Gln Tyr
            420                 425                 430

Asn Ser Thr Tyr Arg Val Val Ser Val Leu Thr Val Leu His Gln Asp
        435                 440                 445

Trp Leu Asn Gly Lys Glu Tyr Lys Cys Lys Val Ser Asn Lys Ala Leu
    450                 455                 460

Ala Ala Pro Ile Glu Lys Thr Ile Ser Lys Ala Lys Gly Gln Pro Arg
465                 470                 475                 480

Glu Pro Gln Val Tyr Thr Leu Pro Pro Ser Arg Glu Glu Met Thr Lys
                485                 490                 495

Asn Gln Val Ser Leu Thr Cys Leu Val Lys Gly Phe Tyr Pro Ser Asp
            500                 505                 510

Ile Ala Val Glu Trp Glu Ser Asn Gly Gln Pro Glu Asn Asn Tyr Lys
        515                 520                 525

Thr Thr Pro Pro Val Leu Asp Ser Asp Gly Ser Phe Phe Leu Tyr Ser
    530                 535                 540

Lys Leu Thr Val Asp Lys Ser Arg Trp Gln Gln Gly Asn Val Phe Ser
545                 550                 555                 560

Cys Ser Val Met His Glu Ala Leu His Asn His Tyr Thr Gln Lys Ser
                565                 570                 575

Leu Ser Leu Ser Pro Gly Lys
            580

<210> SEQ ID NO 22
<211> LENGTH: 1749
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 22
caagtcacac tgcgtgaaag cggccctgcc ctggtcaagc ccacccagac cctgaccctg      60
acctgcacct tctccggctt cagcctggcc cctacctcct ccagcaccaa gaaaacccag     120
ctgcagctcg aacatctgct gctggacctg cagatgatcc tgaacggcat caacaactac     180
aagaacccca agctgaccgc catgctgacc ttcaagttct acatgcccaa gaaggccacc     240
gagctgaaaa catctgcagtg cctggaagag gaactgaagc cctggaaga agtgctgaac     300 ctggcccagt ccaagaactt ccacctgagg cctcgggacc tgatctccaa catcaacgtg     360
atcgtgctgg aactgaaggg ctccgagaca accttcatgt gcgagtacgc cgacgagaca     420
gccaccatcg tggaatttct gaaccggtgg atcaccttct gccagtccat catctccacc     480
ctgacctcca cctccggcat gtccgtgggc tggatccggc agcctcctgg caaggccctg     540
gagtggctgg ccgacatttg gtgggacgac aagaaggact acaaccccag cctgaagtcc     600
cggctgacca tctccaagga cacctccaag aaccaagtgg tgctgaaagt gaccaacatg     660
```

-continued

```
gaccccgccg acaccgccac ctactactgc gcccggtcca tgatcaccaa ctggtacttc    720
gacgtgtggg gcgctggcac caccgtgacc gtgtcctctg ctagcaccaa gggcccctcc    780
gtgttccctc tggccccttc cagcaagtct acctccggcg gcacagctgc tctgggctgc    840
ctggtcaagg actacttccc tgagcctgtg acagtgtcct ggaactctgg cgccctgacc    900
tctggcgtgc acaccttccc tgccgtgctg cagtcctccg gcctgtactc cctgtcctcc    960
gtggtcacag tgccttcaag cagcctgggc acccagacct atatctgcaa cgtgaaccac    1020
aagccttcca acaccaaggt ggacaagcgg gtggagccta agtcctgcga caagacccac    1080
acctgtcctc cctgccctgc tcctgaactg ctgggcggcc cttctgtgtt cctgttccct    1140
ccaaagccca aggacaccct gatgatctcc cggacccctg aagtgacctg cgtggtggtg    1200
gccgtgtccc acgaggatcc tgaagtgaag ttcaattggt acgtggacgg cgtggaggtg    1260
cacaacgcca agaccaagcc tcgggaggaa cagtacaact ccacctaccg ggtggtgtcc    1320
gtgctgaccg tgctgcacca ggactggctg aacggcaaag agtacaagtg caaagtctcc    1380
aacaaggccc tggccgcccc tatcgaaaag acaatctcca aggccaaggg ccagcctagg    1440 gaacccagg tgtacaccct gccacccagc cgggaggaaa tgaccaagaa ccaggtgtcc    1500
ctgacctgtc tggtcaaggg cttctaccct tccgatatcg ccgtggagtg ggagtctaac    1560
ggccagcctg agaacaacta caagaccacc cctcctgtgc tggactccga cggctccttc    1620
ttcctgtact ccaaactgac cgtggacaag tcccggtggc agcagggcaa cgtgttctcc    1680
tgctccgtga tgcacgaggc cctgcacaac cactacaccc agaagtccct gtccctgtct    1740
cccggcaag                                                            1749
```

<210> SEQ ID NO 23
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Lys Ala Gln Leu Ser Val Gly Tyr Met His
1               5                   10

<210> SEQ ID NO 24
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Asp Thr Ser Lys Leu Ala Ser
1               5

<210> SEQ ID NO 25
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 25

Phe Gln Gly Ser Gly Tyr Pro Phe Thr
1               5

<210> SEQ ID NO 26
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Lys Ala Gln Leu Ser Val Gly Tyr Met His
1               5                   10

<210> SEQ ID NO 27
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Asp Thr Ser Lys Leu Ala Ser
1               5

<210> SEQ ID NO 28
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Phe Gln Gly Ser Gly Tyr Pro Phe Thr
1               5

<210> SEQ ID NO 29
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Gln Leu Ser Val Gly Tyr
1               5

<210> SEQ ID NO 30
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Asp Thr Ser
1
```

```
<210> SEQ ID NO 31
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Gly Ser Gly Tyr Pro Phe
1               5

<210> SEQ ID NO 32
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Leu Ser Val Gly Tyr
1               5

<210> SEQ ID NO 33
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Asp Thr Ser
1

<210> SEQ ID NO 34
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Phe Gln Gly Ser Gly Tyr Pro Phe Thr
1               5

<210> SEQ ID NO 35
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Asp Ile Gln Met Thr Gln Ser Pro Ser Thr Leu Ser Ala Ser Val Gly
1               5                   10                  15

Asp Arg Val Thr Ile Thr Cys Lys Ala Gln Leu Ser Val Gly Tyr Met
            20                  25                  30
```

His Trp Tyr Gln Gln Lys Pro Gly Lys Ala Pro Lys Leu Leu Ile Tyr
            35                  40                  45

Asp Thr Ser Lys Leu Ala Ser Gly Val Pro Ser Arg Phe Ser Gly Ser
     50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Phe Gln Gly Ser Gly Tyr Pro Phe Thr
                 85                  90                  95

Phe Gly Gly Gly Thr Lys Leu Glu Ile Lys
            100                 105

<210> SEQ ID NO 36
<211> LENGTH: 318
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 36
gacatccaga tgacccagag ccctccacc ctgtccgcct ccgtgggcga cagagtgacc      60
atcacttgca aggcccagct gtccgtgggc tacatgcact ggtatcagca gaagcccggc    120
aaggccccta gctgctgat ctacgacacc tccaagctgg cctccggcgt gccctccaga    180
ttctccggct ctggctccgg caccgagttc accctgacca tctccagcct gcagcccgac    240
gacttcgcca cctactactg ttttcaaggc tccggctacc ccttcacctt cggcggaggc    300
accaagctgg aaatcaag                                                  318

<210> SEQ ID NO 37
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Asp Ile Gln Met Thr Gln Ser Pro Ser Thr Leu Ser Ala Ser Val Gly
 1               5                  10                  15

Asp Arg Val Thr Ile Thr Cys Lys Ala Gln Leu Ser Val Gly Tyr Met
             20                  25                  30

His Trp Tyr Gln Gln Lys Pro Gly Lys Ala Pro Lys Leu Leu Ile Tyr
            35                  40                  45

Asp Thr Ser Lys Leu Ala Ser Gly Val Pro Ser Arg Phe Ser Gly Ser
     50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Phe Gln Gly Ser Gly Tyr Pro Phe Thr
                 85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
         115                 120                 125

Ala Ser Val Val Cys Leu Leu Asn Asn Phe Tyr Pro Arg Glu Ala Lys
     130                 135                 140

Val Gln Trp Lys Val Asp Asn Ala Leu Gln Ser Gly Asn Ser Gln Glu

```
                145                 150                 155                 160
Ser Val Thr Glu Gln Asp Ser Lys Asp Ser Thr Tyr Ser Leu Ser Ser
                    165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
                195                 200                 205

Asn Arg Gly Glu Cys
        210
```

<210> SEQ ID NO 38
<211> LENGTH: 639
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 38

```
gacatccaga tgacccagag cccctccacc ctgtccgcct ccgtgggcga cagagtgacc    60
atcacttgca aggcccagct gtccgtgggc tacatgcact ggtatcagca aaagcccggc   120
aaggccccta agctgctgat ctacgacacc tccaagctgg cctccggcgt gccctccaga   180
ttctccggct ctggctccgg caccgagttc accctgacca tctccagcct gcagcccgac   240
gacttcgcca cctactactg ttttcaaggc tccggctacc ccttcacctt cggcggaggc   300
accaagctgg aaatcaagcg tacggtggcc gctcccagcg tgttcatctt cccccccagc   360
gacgagcagc tgaagagcgg caccgccagc gtggtgtgcc tgctgaacaa cttctacccc   420
cgggaggcca aggtgcagtg gaaggtggac aacgccctgc agagcggcaa cagccaggag   480
agcgtcaccg agcaggacag caaggactcc acctacagcc tgagcagcac cctgaccctg   540
agcaaggccg actacgagaa gcataaggtg tacgcctgcg aggtgacccc ccagggcctg   600
tccagccccg tgaccaagag cttcaacagg ggcgagtgc                          639
```

<210> SEQ ID NO 39
<211> LENGTH: 145
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 39

```
Gly Phe Ser Leu Ala Pro Thr Ser Ser Thr Lys Lys Thr Gln Leu
1               5                   10                  15

Gln Leu Glu His Leu Leu Leu Asp Leu Gln Met Ile Leu Asn Gly Ile
                20                  25                  30

Asn Asn Tyr Lys Asn Pro Lys Leu Thr Arg Met Leu Thr Ala Lys Phe
            35                  40                  45

Tyr Met Pro Lys Lys Ala Thr Glu Leu Lys His Leu Gln Cys Leu Glu
        50                  55                  60

Glu Glu Leu Lys Pro Leu Glu Glu Val Leu Asn Leu Ala Gln Ser Lys
65                  70                  75                  80

Asn Phe His Leu Arg Pro Arg Asp Leu Ile Ser Asn Ile Asn Val Ile
                85                  90                  95

Val Leu Glu Leu Lys Gly Ser Glu Thr Thr Phe Met Cys Glu Tyr Ala
```

```
            100                 105                 110
Asp Glu Thr Ala Thr Ile Val Glu Phe Leu Asn Arg Trp Ile Thr Phe
        115                 120                 125

Cys Gln Ser Ile Ile Ser Thr Leu Thr Ser Thr Ser Gly Met Ser Val
    130                 135                 140

Gly
145

<210> SEQ ID NO 40
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Asp Ile Trp Trp Asp Asp Lys Lys Asp Tyr Asn Pro Ser Leu Lys Ser
1               5                   10                  15

<210> SEQ ID NO 41
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Ser Met Ile Thr Asn Trp Tyr Phe Asp Val
1               5                   10

<210> SEQ ID NO 42
<211> LENGTH: 141
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Ser Thr Ser Gly Met Ser Val Gly
    130                 135                 140
```

```
<210> SEQ ID NO 43
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Asp Ile Trp Trp Asp Asp Lys Lys Asp Tyr Asn Pro Ser Leu Lys Ser
1               5                   10                  15

<210> SEQ ID NO 44
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Ser Met Ile Thr Asn Trp Tyr Phe Asp Val
1               5                   10

<210> SEQ ID NO 45
<211> LENGTH: 142
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

Gly Phe Ser Leu Ala Pro Thr Ser Ser Thr Lys Lys Thr Gln Leu
1               5                   10                  15

Gln Leu Glu His Leu Leu Leu Asp Leu Gln Met Ile Leu Asn Gly Ile
                20                  25                  30

Asn Asn Tyr Lys Asn Pro Lys Leu Thr Arg Met Leu Thr Ala Lys Phe
            35                  40                  45

Tyr Met Pro Lys Lys Ala Thr Glu Leu Lys His Leu Gln Cys Leu Glu
        50                  55                  60

Glu Glu Leu Lys Pro Leu Glu Glu Val Leu Asn Leu Ala Gln Ser Lys
65                  70                  75                  80

Asn Phe His Leu Arg Pro Arg Asp Leu Ile Ser Asn Ile Asn Val Ile
                85                  90                  95

Val Leu Glu Leu Lys Gly Ser Glu Thr Thr Phe Met Cys Glu Tyr Ala
            100                 105                 110

Asp Glu Thr Ala Thr Ile Val Glu Phe Leu Asn Arg Trp Ile Thr Phe
        115                 120                 125

Cys Gln Ser Ile Ile Ser Thr Leu Thr Ser Thr Ser Gly Met
        130                 135                 140

<210> SEQ ID NO 46
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 46

Trp Trp Asp Asp Lys
1               5

<210> SEQ ID NO 47
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Ser Met Ile Thr Asn Trp Tyr Phe Asp Val
1               5                   10

<210> SEQ ID NO 48
<211> LENGTH: 143
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

Gly Phe Ser Leu Ala Pro Thr Ser Ser Thr Lys Lys Thr Gln Leu
1               5                   10                  15

Gln Leu Glu His Leu Leu Leu Asp Leu Gln Met Ile Leu Asn Gly Ile
                20                  25                  30

Asn Asn Tyr Lys Asn Pro Lys Leu Thr Arg Met Leu Thr Ala Lys Phe
            35                  40                  45

Tyr Met Pro Lys Lys Ala Thr Glu Leu Lys His Leu Gln Cys Leu Glu
        50                  55                  60

Glu Glu Leu Lys Pro Leu Glu Glu Val Leu Asn Leu Ala Gln Ser Lys
65                  70                  75                  80

Asn Phe His Leu Arg Pro Arg Asp Leu Ile Ser Asn Ile Asn Val Ile
                85                  90                  95

Val Leu Glu Leu Lys Gly Ser Glu Thr Thr Phe Met Cys Glu Tyr Ala
            100                 105                 110

Asp Glu Thr Ala Thr Ile Val Glu Phe Leu Asn Arg Trp Ile Thr Phe
        115                 120                 125

Cys Gln Ser Ile Ile Ser Thr Leu Thr Ser Thr Ser Gly Met Ser
    130                 135                 140

<210> SEQ ID NO 49
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Ile Trp Trp Asp Asp Lys Lys
1               5

<210> SEQ ID NO 50
<211> LENGTH: 12
<212> TYPE: PRT
```

<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 50

Ala Arg Ser Met Ile Thr Asn Trp Tyr Phe Asp Val
1               5                   10

<210> SEQ ID NO 51
<211> LENGTH: 253
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 51

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ala Pro Thr
                20                  25                  30

Ser Ser Ser Thr Lys Lys Thr Gln Leu Gln Leu Glu His Leu Leu Leu
            35                  40                  45

Asp Leu Gln Met Ile Leu Asn Gly Ile Asn Asn Tyr Lys Asn Pro Lys
    50                  55                  60

Leu Thr Arg Met Leu Thr Ala Lys Phe Tyr Met Pro Lys Lys Ala Thr
65                  70                  75                  80

Glu Leu Lys His Leu Gln Cys Leu Glu Glu Glu Leu Lys Pro Leu Glu
                85                  90                  95

Glu Val Leu Asn Leu Ala Gln Ser Lys Asn Phe His Leu Arg Pro Arg
                100                 105                 110

Asp Leu Ile Ser Asn Ile Asn Val Ile Val Leu Glu Leu Lys Gly Ser
            115                 120                 125

Glu Thr Thr Phe Met Cys Glu Tyr Ala Asp Glu Thr Ala Thr Ile Val
130                 135                 140

Glu Phe Leu Asn Arg Trp Ile Thr Phe Cys Gln Ser Ile Ile Ser Thr
145                 150                 155                 160

Leu Thr Ser Thr Ser Gly Met Ser Val Gly Trp Ile Arg Gln Pro Pro
                165                 170                 175

Gly Lys Ala Leu Glu Trp Leu Ala Asp Ile Trp Trp Asp Asp Lys Lys
            180                 185                 190

Asp Tyr Asn Pro Ser Leu Lys Ser Arg Leu Thr Ile Ser Lys Asp Thr
        195                 200                 205

Ser Lys Asn Gln Val Val Leu Lys Val Thr Asn Met Asp Pro Ala Asp
    210                 215                 220

Thr Ala Thr Tyr Tyr Cys Ala Arg Ser Met Ile Thr Asn Trp Tyr Phe
225                 230                 235                 240

Asp Val Trp Gly Ala Gly Thr Thr Val Thr Val Ser Ser
                245                 250

<210> SEQ ID NO 52
<211> LENGTH: 759
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 52

```
caagtcacac tgcgtgaaag cggccctgcc ctggtcaagc ccacccagac cctgaccctg      60
acctgcacct tctccggctt cagcctggcc cctacctcct ccagcaccaa gaaaacccag     120
ctgcagctcg aacatctgct gctggacctg cagatgatcc tgaacggcat caacaactac     180
aagaacccca gctgacccg gatgctgacc gccaagttct acatgcccaa gaaggccacc     240
gagctgaaac atctgcagtg cctggaagag gaactgaagc ccctggaaga gtgctgaac     300
ctggcccagt ccaagaactt ccacctgagg cctcgggacc tgatctccaa catcaacgtg     360
atcgtgctgg aactgaaggg ctccgagaca accttcatgt gcgagtacgc cgacgagaca     420
gccaccatcg tggaatttct gaaccggtgg atcaccttct gccagtccat catctccacc     480
ctgacctcca cctccggcat gtccgtgggc tggatccggc agcctcctgg caaggccctg     540
gagtggctgg ccgacatttg gtgggacgac aagaaggact acaacccag cctgaagtcc     600
cggctgacca tctccaagga cacctccaag aaccaagtgg tgctgaaagt gaccaacatg     660
gaccccgccg acaccgccac ctactactgc gcccggtcca tgatcaccaa ctggtacttc     720
gacgtgtggg gcgctggcac caccgtgacc gtgtcctct                            759
```

<210> SEQ ID NO 53
<211> LENGTH: 583
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 53

```
Gln Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ala Pro Thr
            20                  25                  30

Ser Ser Ser Thr Lys Lys Thr Gln Leu Gln Leu Glu His Leu Leu Leu
        35                  40                  45

Asp Leu Gln Met Ile Leu Asn Gly Ile Asn Asn Tyr Lys Asn Pro Lys
    50                  55                  60

Leu Thr Arg Met Leu Thr Ala Lys Phe Tyr Met Pro Lys Lys Ala Thr
65                  70                  75                  80

Glu Leu Lys His Leu Gln Cys Leu Glu Glu Glu Leu Lys Pro Leu Glu
                85                  90                  95

Glu Val Leu Asn Leu Ala Gln Ser Lys Asn Phe His Leu Arg Pro Arg
            100                 105                 110

Asp Leu Ile Ser Asn Ile Asn Val Ile Val Leu Glu Leu Lys Gly Ser
        115                 120                 125

Glu Thr Thr Phe Met Cys Glu Tyr Ala Asp Glu Thr Ala Thr Ile Val
    130                 135                 140

Glu Phe Leu Asn Arg Trp Ile Thr Phe Cys Gln Ser Ile Ile Ser Thr
145                 150                 155                 160

Leu Thr Ser Thr Ser Gly Met Ser Val Gly Trp Ile Arg Gln Pro Pro
                165                 170                 175

Gly Lys Ala Leu Glu Trp Leu Ala Asp Ile Trp Trp Asp Asp Lys Lys
            180                 185                 190

Asp Tyr Asn Pro Ser Leu Lys Ser Arg Leu Thr Ile Ser Lys Asp Thr
```

```
                195                 200                 205
Ser Lys Asn Gln Val Val Leu Lys Val Thr Asn Met Asp Pro Ala Asp
210                 215                 220

Thr Ala Thr Tyr Tyr Cys Ala Arg Ser Met Ile Thr Asn Trp Tyr Phe
225                 230                 235                 240

Asp Val Trp Gly Ala Gly Thr Thr Val Thr Val Ser Ser Ala Ser Thr
                245                 250                 255

Lys Gly Pro Ser Val Phe Pro Leu Ala Pro Ser Ser Lys Ser Thr Ser
            260                 265                 270

Gly Gly Thr Ala Ala Leu Gly Cys Leu Val Lys Asp Tyr Phe Pro Glu
        275                 280                 285

Pro Val Thr Val Ser Trp Asn Ser Gly Ala Leu Thr Ser Gly Val His
290                 295                 300

Thr Phe Pro Ala Val Leu Gln Ser Ser Gly Leu Tyr Ser Leu Ser Ser
305                 310                 315                 320

Val Val Thr Val Pro Ser Ser Ser Leu Gly Thr Gln Thr Tyr Ile Cys
                325                 330                 335

Asn Val Asn His Lys Pro Ser Asn Thr Lys Val Asp Lys Arg Val Glu
            340                 345                 350

Pro Lys Ser Cys Asp Lys Thr His Thr Cys Pro Pro Cys Pro Ala Pro
        355                 360                 365

Glu Leu Leu Gly Gly Pro Ser Val Phe Leu Phe Pro Pro Lys Pro Lys
370                 375                 380

Asp Thr Leu Met Ile Ser Arg Thr Pro Glu Val Thr Cys Val Val Val
385                 390                 395                 400

Ala Val Ser His Glu Asp Pro Glu Val Lys Phe Asn Trp Tyr Val Asp
                405                 410                 415

Gly Val Glu Val His Asn Ala Lys Thr Lys Pro Arg Glu Glu Gln Tyr
            420                 425                 430

Asn Ser Thr Tyr Arg Val Val Ser Val Leu Thr Val Leu His Gln Asp
        435                 440                 445

Trp Leu Asn Gly Lys Glu Tyr Lys Cys Lys Val Ser Asn Lys Ala Leu
450                 455                 460

Ala Ala Pro Ile Glu Lys Thr Ile Ser Lys Ala Lys Gly Gln Pro Arg
465                 470                 475                 480

Glu Pro Gln Val Tyr Thr Leu Pro Pro Ser Arg Glu Glu Met Thr Lys
                485                 490                 495

Asn Gln Val Ser Leu Thr Cys Leu Val Lys Gly Phe Tyr Pro Ser Asp
            500                 505                 510

Ile Ala Val Glu Trp Glu Ser Asn Gly Gln Pro Glu Asn Asn Tyr Lys
        515                 520                 525

Thr Thr Pro Pro Val Leu Asp Ser Asp Gly Ser Phe Phe Leu Tyr Ser
530                 535                 540

Lys Leu Thr Val Asp Lys Ser Arg Trp Gln Gln Gly Asn Val Phe Ser
545                 550                 555                 560

Cys Ser Val Met His Glu Ala Leu His Asn His Tyr Thr Gln Lys Ser
                565                 570                 575

Leu Ser Leu Ser Pro Gly Lys
            580

<210> SEQ ID NO 54
<211> LENGTH: 1749
<212> TYPE: DNA
<213> ORGANISM: Artificial Sequence
```

<220> FEATURE:
<221> NAME/KEY: source
<223> OTHER INFORMATION: /note="Description of Artificial Sequence:
      Synthetic polynucleotide"

<400> SEQUENCE: 54

```
caagtcacac tgcgtgaaag cggccctgcc ctggtcaagc ccacccagac cctgaccctg      60
acctgcacct tctccggctt cagcctggcc cctacctcct ccagcaccaa gaaaacccag     120
ctgcagctcg aacatctgct gctggacctg cagatgatcc tgaacggcat caacaactac     180
aagaacccca agctgacccg gatgctgacc gccaagttct acatgcccaa gaaggccacc     240
gagctgaaac atctgcagtg cctggaagag gaactgaagc ccctggaaga agtgctgaac     300
ctggcccagt ccaagaactt ccacctgagg cctcgggacc tgatctccaa catcaacgtg     360
atcgtgctgg aactgaaggg ctccgagaca accttcatgt gcgagtacgc cgacgagaca     420
gccaccatcg tggaatttct gaaccggtgg atcaccttct gccagtccat catctccacc     480
ctgacctcca cctccggcat gtccgtgggc tggatccggc agcctcctgg caaggccctg     540
gagtggctgg ccgacatttg gtgggacgac aagaaggact acaacccag cctgaagtcc      600
cggctgacca tctccaagga cacctccaag aaccaagtgg tgctgaaagt gaccaacatg     660
gaccccgccg acaccgccac ctactactgc gcccggtcca tgatcaccaa ctggtacttc     720
gacgtgtggg gcgctggcac caccgtgacc gtgtcctctg ctagcaccaa gggcccctcc     780
gtgttccctc tggccccttc cagcaagtct acctccggcg gcacagctgc tctgggctgc     840
ctggtcaagg actacttccc tgagcctgtg acagtgtcct ggaactctgg cgccctgacc     900
tctggcgtgc acaccttccc tgccgtgctg cagtcctccg gcctgtactc cctgtcctcc     960
gtggtcacag tgccttcaag cagcctgggc acccagacct atatctgcaa cgtgaaccac    1020
aagccttcca acaccaaggt ggacaagcgg gtggagccta agtcctgcga caagacccac    1080
acctgtcctc cctgccctgc tcctgaactg ctgggcggcc cttctgtgtt cctgttccct    1140
ccaaagccca aggacaccct gatgatctcc cggacccctg aagtgacctg cgtggtggtg    1200
gccgtgtccc acgaggatcc tgaagtgaag ttcaattggt acgtggacgg cgtggaggtg    1260
cacaacgcca agaccaagcc tcgggaggaa cagtacaact ccacctaccg ggtggtgtcc    1320
gtgctgaccg tgctgcacca ggactggctg aacggcaaag agtacaagtg caaagtctcc    1380
aacaaggccc tggccgcccc tatcgaaaag acaatctcca aggccaaggg ccagcctagg    1440
gaacccagg tgtacaccct gccacccagc cgggaggaaa tgaccaagaa ccaggtgtcc     1500
ctgacctgtc tggtcaaggg cttctaccct tccgatatcg ccgtggagtg ggagtctaac    1560
ggccagcctg agaacaacta caagaccacc cctcctgtgc tggactccga cggctccttc    1620
ttcctgtact ccaaactgac cgtggacaag tccggtggc agcagggcaa cgtgttctcc     1680
tgctccgtga tgcacgaggc cctgcacaac cactacaccc agaagtccct gtccctgtct    1740
cccggcaag                                                            1749
```

<210> SEQ ID NO 55
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Lys Ala Gln Leu Ser Val Gly Tyr Met His
1               5                   10

<210> SEQ ID NO 56
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Asp Thr Ser Lys Leu Ala Ser
1               5

<210> SEQ ID NO 57
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Phe Gln Gly Ser Gly Tyr Pro Phe Thr
1               5

<210> SEQ ID NO 58
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Lys Ala Gln Leu Ser Val Gly Tyr Met His
1               5                   10

<210> SEQ ID NO 59
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Asp Thr Ser Lys Leu Ala Ser
1               5

<210> SEQ ID NO 60
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Phe Gln Gly Ser Gly Tyr Pro Phe Thr
1               5

```
<210> SEQ ID NO 61
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Gln Leu Ser Val Gly Tyr
1               5

<210> SEQ ID NO 62
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Asp Thr Ser
1

<210> SEQ ID NO 63
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Gly Ser Gly Tyr Pro Phe
1               5

<210> SEQ ID NO 64
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Leu Ser Val Gly Tyr
1               5

<210> SEQ ID NO 65
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Asp Thr Ser
1

<210> SEQ ID NO 66
<211> LENGTH: 9
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 66

Phe Gln Gly Ser Gly Tyr Pro Phe Thr
1               5

<210> SEQ ID NO 67
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 67

Asp Ile Gln Met Thr Gln Ser Pro Ser Thr Leu Ser Ala Ser Val Gly
1               5                   10                  15

Asp Arg Val Thr Ile Thr Cys Lys Ala Gln Leu Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys
            100                 105

<210> SEQ ID NO 68
<211> LENGTH: 318
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 68
gacatccaga tgacccagag cccctccacc ctgtccgcct ccgtgggcga cagagtgacc    60
atcacttgca aggcccagct gtccgtgggc tacatgcact ggtatcagca aaagcccggc   120
aaggccccta agctgctgat ctacgacacc tccaagctgg cctccggcgt gccctccaga   180
ttctccggct ctggctccgg caccgagttc accctgacca tctccagcct gcagcccgac   240
gacttcgcca cctactactg ttttcaaggc tccggctacc ccttcacctt cggcggaggc   300
accaagctgg aaatcaag                                                 318

<210> SEQ ID NO 69
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 69
```

```
Asp Ile Gln Met Thr Gln Ser Pro Ser Thr Leu Ser Ala Ser Val Gly
  1               5                  10                 15

Asp Arg Val Thr Ile Thr Cys Lys Ala Gln Leu Ser Val Gly Tyr Met
             20                  25                 30

His Trp Tyr Gln Gln Lys Pro Gly Lys Ala Pro Lys Leu Leu Ile Tyr
         35                  40                  45

Asp Thr Ser Lys Leu Ala Ser Gly Val Pro Ser Arg Phe Ser Gly Ser
     50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Phe Gln Gly Ser Gly Tyr Pro Phe Thr
             85                  90                  95

Phe Gly Gly Gly Thr Lys Leu Glu Ile Lys Arg Thr Val Ala Ala Pro
             100                 105                110

Ser Val Phe Ile Phe Pro Pro Ser Asp Glu Gln Leu Lys Ser Gly Thr
             115                 120                 125

Ala Ser Val Val Cys Leu Leu Asn Asn Phe Tyr Pro Arg Glu Ala Lys
         130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
             165                 170                 175

Thr Leu Thr Leu Ser Lys Ala Asp Tyr Glu Lys His Lys Val Tyr Ala
             180                 185                 190

Cys Glu Val Thr His Gln Gly Leu Ser Ser Pro Val Thr Lys Ser Phe
         195                 200                 205

Asn Arg Gly Glu Cys
    210
```

<210> SEQ ID NO 70
<211> LENGTH: 639
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 70

```
gacatccaga tgacccagag cccctccacc ctgtccgcct ccgtgggcga cagagtgacc      60
atcacttgca aggcccagct gtccgtgggc tacatgcact ggtatcagca aaagcccggc    120
aaggccccta agctgctgat ctacgacacc tccaagctgg cctccggcgt gccctccaga    180
ttctccggct ctggctccgg caccgagttc accctgacca tctccagcct gcagcccgac    240
gacttcgcca cctactactg ttttcaaggc tccggctacc ccttcacctt cggcggaggc    300
accaagctgg aaatcaagcg tacggtggcc gctcccagcg tgttcatctt cccccccagc    360
gacgagcagc tgaagagcgg caccgccagc gtggtgtgcc tgctgaacaa cttctacccc    420
cgggaggcca aggtgcagtg gaaggtggac aacgccctgc agagcggcaa cagccaggag    480
agcgtcaccg agcaggacag caaggactcc acctacagcc tgagcagcac cctgaccctg    540
agcaaggccg actacgagaa gcataaggtg tacgcctgcg aggtgaccca ccagggcctg    600
tccagccccg tgaccaagag cttcaacagg ggcgagtgc                            639
```

<210> SEQ ID NO 71
<211> LENGTH: 60

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MISC_FEATURE
<222> LOCATION: (1)..(5)
<223> OTHER INFORMATION: /note="This region may encompass 1-5 residues"
<220> FEATURE:
<221> NAME/KEY: MISC_FEATURE
<222> LOCATION: (7)..(11)
<223> OTHER INFORMATION: /note="This region may encompass 1-5 residues"
<220> FEATURE:
<221> NAME/KEY: MISC_FEATURE
<222> LOCATION: (13)..(17)
<223> OTHER INFORMATION: /note="This region may encompass 1-5 residues"
<220> FEATURE:
<221> NAME/KEY: MISC_FEATURE
<222> LOCATION: (19)..(23)
<223> OTHER INFORMATION: /note="This region may encompass 1-5 residues"
<220> FEATURE:
<221> NAME/KEY: MISC_FEATURE
<222> LOCATION: (25)..(29)
<223> OTHER INFORMATION: /note="This region may encompass 1-5 residues"
<220> FEATURE:
<221> NAME/KEY: MISC_FEATURE
<222> LOCATION: (31)..(35)
<223> OTHER INFORMATION: /note="This region may encompass 1-5 residues"
<220> FEATURE:
<221> NAME/KEY: MISC_FEATURE
<222> LOCATION: (37)..(41)
<223> OTHER INFORMATION: /note="This region may encompass 1-5 residues"
<220> FEATURE:
<221> NAME/KEY: MISC_FEATURE
<222> LOCATION: (43)..(47)
<223> OTHER INFORMATION: /note="This region may encompass 1-5 residues"
<220> FEATURE:
<221> NAME/KEY: MISC_FEATURE
<222> LOCATION: (49)..(53)
<223> OTHER INFORMATION: /note="This region may encompass 1-5 residues"
<220> FEATURE:
<221> NAME/KEY: MISC_FEATURE
<222> LOCATION: (55)..(59)
<223> OTHER INFORMATION: /note="This region may encompass 1-5 residues"
<220> FEATURE:
<221> NAME/KEY: MISC_FEATURE
<222> LOCATION: (1)..(60)
<223> OTHER INFORMATION: /note="This sequence may encompass 0-10
      '(Gly)n-Ser' repeating units where n=1-5"

<400> SEQUENCE: 71

Gly Gly Gly Gly Gly Ser Gly Gly Gly Gly Ser Gly Gly Gly Gly
1               5                   10                  15

Gly Ser Gly Gly Gly Gly Gly Ser Gly Gly Gly Gly Ser Gly Gly
                20                  25                  30

Gly Gly Gly Ser Gly Gly Gly Gly Gly Ser Gly Gly Gly Gly Ser
            35                  40                  45

Gly Gly Gly Gly Gly Ser Gly Gly Gly Gly Gly Ser
        50                  55                  60

<210> SEQ ID NO 72
<211> LENGTH: 60
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MISC_FEATURE
<222> LOCATION: (1)..(5)
<223> OTHER INFORMATION: /note="This region may encompass 1-5 residues"
```

```
<220> FEATURE:
<221> NAME/KEY: MISC_FEATURE
<222> LOCATION: (7)..(11)
<223> OTHER INFORMATION: /note="This region may encompass 1-5 residues"
<220> FEATURE:
<221> NAME/KEY: MISC_FEATURE
<222> LOCATION: (13)..(17)
<223> OTHER INFORMATION: /note="This region may encompass 1-5 residues"
<220> FEATURE:
<221> NAME/KEY: MISC_FEATURE
<222> LOCATION: (19)..(23)
<223> OTHER INFORMATION: /note="This region may encompass 1-5 residues"
<220> FEATURE:
<221> NAME/KEY: MISC_FEATURE
<222> LOCATION: (25)..(29)
<223> OTHER INFORMATION: /note="This region may encompass 1-5 residues"
<220> FEATURE:
<221> NAME/KEY: MISC_FEATURE
<222> LOCATION: (31)..(35)
<223> OTHER INFORMATION: /note="This region may encompass 1-5 residues"
<220> FEATURE:
<221> NAME/KEY: MISC_FEATURE
<222> LOCATION: (37)..(41)
<223> OTHER INFORMATION: /note="This region may encompass 1-5 residues"
<220> FEATURE:
<221> NAME/KEY: MISC_FEATURE
<222> LOCATION: (43)..(47)
<223> OTHER INFORMATION: /note="This region may encompass 1-5 residues"
<220> FEATURE:
<221> NAME/KEY: MISC_FEATURE
<222> LOCATION: (49)..(53)
<223> OTHER INFORMATION: /note="This region may encompass 1-5 residues"
<220> FEATURE:
<221> NAME/KEY: MISC_FEATURE
<222> LOCATION: (55)..(59)
<223> OTHER INFORMATION: /note="This region may encompass 1-5 residues"
<220> FEATURE:
<221> NAME/KEY: MISC_FEATURE
<222> LOCATION: (1)..(60)
<223> OTHER INFORMATION: /note="This sequence may encompass 0-10
      '(Gly)n-Ala' repeating units where n=1-5"

<400> SEQUENCE: 72

Gly Gly Gly Gly Gly Ala Gly Gly Gly Gly Ala Gly Gly Gly Gly
1               5                   10                  15

Gly Ala Gly Gly Gly Gly Gly Ala Gly Gly Gly Gly Ala Gly Gly
            20                  25                  30

Gly Gly Gly Ala Gly Gly Gly Gly Gly Ala Gly Gly Gly Gly Ala
        35                  40                  45

Gly Gly Gly Gly Gly Ala Gly Gly Gly Gly Ala
    50                  55                  60

<210> SEQ ID NO 73
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MISC_FEATURE
<222> LOCATION: (1)..(10)
<223> OTHER INFORMATION: /note="This region may encompass 0-10 residues"
<220> FEATURE:
<221> NAME/KEY: MISC_FEATURE
<222> LOCATION: (12)..(21)
<223> OTHER INFORMATION: /note="This region may encompass 0-10 residues"
<220> FEATURE:
<221> NAME/KEY: MISC_FEATURE
<222> LOCATION: (23)..(32)
<223> OTHER INFORMATION: /note="This region may encompass 0-10 residues"
<220> FEATURE:
<221> NAME/KEY: MISC_FEATURE
```

<222> LOCATION: (34)..(43)
<223> OTHER INFORMATION: /note="This region may encompass 0-10 residues"
<220> FEATURE:
<221> NAME/KEY: MISC_FEATURE
<222> LOCATION: (45)..(54)
<223> OTHER INFORMATION: /note="This region may encompass 0-10 residues"
<220> FEATURE:
<221> NAME/KEY: MISC_FEATURE
<222> LOCATION: (56)..(65)
<223> OTHER INFORMATION: /note="This region may encompass 0-10 residues"
<220> FEATURE:
<221> NAME/KEY: MISC_FEATURE
<222> LOCATION: (67)..(76)
<223> OTHER INFORMATION: /note="This region may encompass 0-10 residues"
<220> FEATURE:
<221> NAME/KEY: MISC_FEATURE
<222> LOCATION: (78)..(87)
<223> OTHER INFORMATION: /note="This region may encompass 0-10 residues"
<220> FEATURE:
<221> NAME/KEY: MISC_FEATURE
<222> LOCATION: (89)..(98)
<223> OTHER INFORMATION: /note="This region may encompass 0-10 residues"
<220> FEATURE:
<221> NAME/KEY: MISC_FEATURE
<222> LOCATION: (100)..(109)
<223> OTHER INFORMATION: /note="This region may encompass 0-10 residues"
<220> FEATURE:
<221> NAME/KEY: MISC_FEATURE
<222> LOCATION: (1)..(110)
<223> OTHER INFORMATION: /note="This sequence may encompass 1-10
      '(Gly)n-Ser' repeating units where n=0-10"

<400> SEQUENCE: 73

Gly Gly Gly Gly Gly Gly Gly Gly Gly Ser Gly Gly Gly Gly Gly
1               5                   10                  15

Gly Gly Gly Gly Ser Gly Gly Gly Gly Gly Gly Gly Gly Gly Gly
            20                  25                  30

Ser Gly Gly Gly Gly Gly Gly Gly Gly Ser Gly Gly Gly Gly
        35                  40                  45

Gly Gly Gly Gly Gly Ser Gly Gly Gly Gly Gly Gly Gly Gly Gly
    50                  55                  60

Gly Ser Gly Gly Gly Gly Gly Gly Gly Gly Ser Gly Gly Gly
65                  70                  75                  80

Gly Gly Gly Gly Gly Gly Gly Ser Gly Gly Gly Gly Gly Gly Gly
                85                  90                  95

Gly Gly Ser Gly Gly Gly Gly Gly Gly Gly Gly Gly Ser
            100                 105                 110

<210> SEQ ID NO 74
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="See specification as filed for detailed
      description of substitutions and preferred embodiments"

<400> SEQUENCE: 74

Gly Gly Gly Gly Ser
1               5

<210> SEQ ID NO 75
<211> LENGTH: 110
<212> TYPE: PRT
<213> ORGANISM: Artificial Sequence -continued

```
<220> FEATURE:
<221> NAME/KEY: source
<223> OTHER INFORMATION: /note="Description of Artificial Sequence:
      Synthetic polypeptide"
<220> FEATURE:
<221> NAME/KEY: MISC_FEATURE
<222> LOCATION: (1)..(10)
<223> OTHER INFORMATION: /note="This region may encompass 0-10 residues"
<220> FEATURE:
<221> NAME/KEY: MISC_FEATURE
<222> LOCATION: (12)..(21)
<223> OTHER INFORMATION: /note="This region may encompass 0-10 residues"
<220> FEATURE:
<221> NAME/KEY: MISC_FEATURE
<222> LOCATION: (23)..(32)
<223> OTHER INFORMATION: /note="This region may encompass 0-10 residues"
<220> FEATURE:
<221> NAME/KEY: MISC_FEATURE
<222> LOCATION: (34)..(43)
<223> OTHER INFORMATION: /note="This region may encompass 0-10 residues"
<220> FEATURE:
<221> NAME/KEY: MISC_FEATURE
<222> LOCATION: (45)..(54)
<223> OTHER INFORMATION: /note="This region may encompass 0-10 residues"
<220> FEATURE:
<221> NAME/KEY: MISC_FEATURE
<222> LOCATION: (56)..(65)
<223> OTHER INFORMATION: /note="This region may encompass 0-10 residues"
<220> FEATURE:
<221> NAME/KEY: MISC_FEATURE
<222> LOCATION: (67)..(76)
<223> OTHER INFORMATION: /note="This region may encompass 0-10 residues"
<220> FEATURE:
<221> NAME/KEY: MISC_FEATURE
<222> LOCATION: (78)..(87)
<223> OTHER INFORMATION: /note="This region may encompass 0-10 residues"
<220> FEATURE:
<221> NAME/KEY: MISC_FEATURE
<222> LOCATION: (89)..(98)
<223> OTHER INFORMATION: /note="This region may encompass 0-10 residues"
<220> FEATURE:
<221> NAME/KEY: MISC_FEATURE
<222> LOCATION: (100)..(109)
<223> OTHER INFORMATION: /note="This region may encompass 0-10 residues"
<220> FEATURE:
<221> NAME/KEY: MISC_FEATURE
<222> LOCATION: (1)..(110)
<223> OTHER INFORMATION: /note="This sequence may encompass 1-10
      '(Gly)n-Ala' repeating units where n=0-10"

<400> SEQUENCE: 75

Gly Gly Gly Gly Gly Gly Gly Gly Gly Ala Gly Gly Gly Gly Gly
1               5                   10                  15

Gly Gly Gly Gly Gly Ala Gly Gly Gly Gly Gly Gly Gly Gly Gly
                20                  25                  30

Ala Gly Gly Gly Gly Gly Gly Gly Gly Ala Gly Gly Gly Gly Gly
            35                  40                  45

Gly Gly Gly Gly Gly Ala Gly Gly Gly Gly Gly Gly Gly Gly Gly
        50                  55                  60

Gly Ala Gly Gly Gly Gly Gly Gly Gly Gly Ala Gly Gly Gly Gly
65                  70                  75                  80

Gly Gly Gly Gly Gly Gly Ala Gly Gly Gly Gly Gly Gly Gly Gly
                85                  90                  95

Gly Gly Ala Gly Gly Gly Gly Gly Gly Gly Gly Gly Ala
            100                 105                 110

<210> SEQ ID NO 76
<211> LENGTH: 5
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="See specification as filed for detailed
      description of substitutions and preferred embodiments"

<400> SEQUENCE: 76

Gly Gly Gly Gly Ala
1               5

<210> SEQ ID NO 77
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 77

Arg Gly Asp Ser
1

<210> SEQ ID NO 78
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 78

His His His His His His
1               5
```

ANTIBODY-IL2 ENGRAFTED PROTEINS AND METHODS OF USE IN THE TREATMENT OF CANCER

CROSS-REFERENCE TO RELATED APPLICATIONS

This application claims the benefit of U.S. Provisional Application No. 62/510,533 filed May 24, 2017, the content of which is hereby incorporated by reference in its entirety.

FIELD

The present invention relates to antibody-cytokine engrafted proteins that bind the interleukin-2 (IL2) low affinity receptor, and methods of cancer treatment.

SEQUENCE LISTING

The instant application contains a Sequence Listing which has been submitted electronically in ASCII format and is hereby incorporated by reference in its entirety. Said ASCII copy, created on Apr. 5, 2018, is named PAT057462-WO-PCT_SL.txt and is 69,489 bytes in size.

BACKGROUND

IL2 was first cloned in 1983 (Taniguchi et al., Nature 1983, 302:305-310, Devos et al., Nucleic Acid Res. 1983, 11(13):4307-4323, Maeda et al., Biochem. Biophys. Res. Comm. 1983, 115:1040-1047). The IL2 protein has a length of 153 amino acids with a signal peptide from amino acids 1-20 and folds into a structure of 4 anti-parallel, amphipathic alpha-helices (Smith K. A., Science 1988, 240:1169-1176).

IL2 mediates its biological effect by signaling through a high affinity or low affinity receptor (Kreig et al., PNAS 2010, 107(26)11906-11911). The high affinity receptor is trimeric, consisting of IL2-Ra (CD25) IL2-R (CD122) and IL2-Ry (CD132). The low affinity receptor is dimeric, consisting only of the IL2-R (CD122) and IL2-Ry (CD132) chains. The low affinity receptor binds IL2, but with 10-100 times less affinity than the trimeric, high affinity receptor, indicating that IL2-Ra (CD25) is important for increase in affinity, but is not a signaling component (Kreig et al., supra). The expression of the IL2 receptors is also distinct. The high affinity IL2 receptor is expressed on activated T cells and CD4+/Foxp3+T regulatory cells (Treg). In contrast, the low affinity IL2 receptor is found on CD8+T effector cells and natural killer cells (NK).

Recombinant IL2 (rhIL2) was initially approved for clinical use in 1992 (Coventry et al., Cancer Mgt Res. 2012 4:215-221). PROLEUKIN® (Aldesleukin) is a modified IL2 that is aglycosylated, lacks an N-terminal alanine and has a serine substituted for cysteine at amino acid 125. PROLEUKIN® was initially indicated as a therapy for malignant melanoma and renal cell carcinoma, but has been used for other cancer types such as colorectal, breast, lung and mesothelioma (Coventry, supra). A study spanning 259 renal cell carcinoma patients from 1986 to 2006, found that 23 patients has a complete response and 30 had a partial response (Klapper et al., Cancer 2008 113(2):293-301). This accounted for an overall objective response rate of 20%, with complete tumor regression in 7% of the patients with renal cell cancer (Klapper et al., supra).

However, IL2 treatment of cancer was not without adverse effects. The 259 patient study noted capillary/vascular leakage, vasodilation and oliguria. There were also Grade 3 and Grade 4 infections, both of catheters and general infection, attributed to neutrophil dysfunction (Klapper et al., supra). PROLEUKIN® literature notes that PROLEUKIN® has been associated with exacerbation of autoimmune diseases and inflammatory disorders such as Crohn's Disease, scleroderma, thyroiditis, inflammatory arthritis, diabetes mellitus, oculo-bulbar myasthenia gravis, crescentic IgA glomerulonephritis, cholecystitis, cerebral vasculitis, Stevens-Johnson syndrome and bullous pemphigoid.

The discovery that Treg cells constitutively expressed the high affinity IL2 receptor and were dependent on IL2 for survival and function indicated why this side effect was seen (D'Cruz et al., Nat. Immuno. 2005, 6:1152-1159). This illustrates the need for IL2 therapeutics with improved pharmacokinetics and with selectivity for activation of CD8+ T cells via the low affinity receptor without activation of Treg cells via the high affinity receptor, as this allows for the treatment of cancer without the unwanted side effects seen with PROLEUKIN®.

DESCRIPTION

The present disclosure provides for IL2 engrafted into the CDR sequences of an antibody having preferred therapeutic profiles over molecules known and used in the clinic. In particular, the provided antibody cytokine engrafted protein compositions increase or maintain CD8+T effector cells while reducing the activity of Treg cells. Additionally, provided compositions convey improved half-life, stability and producibility over recombinant human IL2 formulations such as PROLEUKIN®. The present disclosure thus provides antibody cytokine engrafted proteins that bind to and promote preferred signaling through the IL2 low affinity receptor, with reduced binding to the IL2 high affinity receptor. Provided are antibody-cytokine engrafted proteins comprising (i) an immunoglobulin heavy chain sequence comprising a heavy chain variable region (VH) and (ii) an immunoglobulin light chain sequence comprising a light chain variable region (VL), and wherein an IL2 molecule is engrafted into a complementarity determining region (CDR) of the VH or the VL of the antibody.

Embodiments of the present disclosure provide antibody cytokine engrafted proteins comprising:
(a) a heavy chain variable region (VH), comprising Complementarity Determining Regions (CDR) HCDRI, HCDR2, HCDR3; and
(b) a light chain variable region (VL), comprising LCDRI, LCDR2, LCDR3; and
(c) an Interleukin 2 (IL2) molecule engrafted into a CDR of the VH or the VL.

The antibody cytokine engrafted protein, comprising an IL2 molecule engrafted into a heavy chain CDR.

The antibody cytokine engrafted protein, wherein the IL2 molecule is engrafted into a region selected from complementarity determining region 1 (HCDRI), complementarity determining region 2 (HCDR2) or complementarity determining region 3 (HCDR3).

The antibody cytokine engrafted protein, comprising an IL2 molecule engrafted into HCDRI.

The antibody cytokine engrafted protein, comprising an IL2 molecule engrafted into a light chain CDR.

The antibody cytokine engrafted protein, wherein the IL2 molecule is engrafted into a region selected from complementarity determining region 1 (LCDRI), complementarity determining region 2 (LCDR2) or complementarity determining region 3 (LCDR3).

The antibody cytokine engrafted protein, comprising an IL2 molecule containing a mutation that reduces the affinity of the IL2 molecule to the high affinity IL2 receptor.

The antibody cytokine engrafted protein, where the antibody cytokine engrafted protein stimulates CD8+ T cell effector proliferation greater than recombinant IL2 or PROLEUKIN®.

The antibody cytokine engrafted protein, where the antibody cytokine engrafted protein stimulates Treg cell proliferation less than recombinant IL2 or PROLEUKIN®.

The antibody cytokine engrafted protein, wherein the antibody cytokine engrafted protein stimulates NK cell proliferation greater than recombinant IL2 or PROLEUKIN®.

The antibody cytokine engrafted protein, where the antibody cytokine engrafted protein has a longer half-life than recombinant IL2 or PROLEUKIN®.

The antibody cytokine engrafted protein, wherein the IL2 molecule consists of SEQ ID NO:4.

The antibody cytokine engrafted protein, wherein the IL2 molecule consists of SEQ ID NO:6.

The antibody cytokine engrafted protein, comprising an IgG class antibody heavy chain.

The antibody cytokine engrafted protein, wherein the IgG is selected from IgG1, IgG2, or IgG4.

The antibody cytokine engrafted protein, wherein the binding specificity of the CDRs to a target is reduced by 10%, 20%, 30%, 40%, 50%, 60%, 70%, 80%, 90%, 95%, 98%, 99%, or 100%, by the engrafted IL2 molecule.

The antibody cytokine engrafted protein, wherein the binding specificity of the CDRs to a target is retained by 10%, 20%, 30%, 40%, 50%, 60%, 70%, 80%, 90%, 95%, 98%, 99%, or 100%, in the presence of the engrafted IL2 molecule.

The antibody cytokine engrafted protein, wherein the binding specificity of the CDRs is distinct from the binding specificity of the IL2 molecule.

The antibody cytokine engrafted protein, wherein the binding specificity of the CDRs is to a non-human target.

The antibody cytokine engrafted protein, wherein the non-human antigen is a VITUS.

The antibody cytokine engrafted protein, wherein the virus is respiratory syncytial virus (RSV).

The antibody cytokine engrafted protein, wherein the RSV is selected from RSV subgroup A and RSV subgroup B.

The antibody cytokine engrafted protein, wherein the antibody scaffold portion of the antibody cytokine engrafted protein is humanized or human.

Embodiments of the present disclosure provide antibody cytokine engrafted proteins comprising: (i) a heavy chain variable region that comprises (a) a HCDR1 of SEQ ID NO: 13, (b) a HCDR2 of SEQ ID NO:14, (c) a HCDR3 of SEQ ID NO:15 and a light chain variable region that comprises: (d) a LCDR1 of SEQ ID NO:29, (e) a LCDR2 of SEQ ID NO:30, and (f) a LCDR3 of SEQ ID NO:31; or (ii) a heavy chain variable region that comprises (a) a HCDR1 of SEQ ID NO:45, (b) a HCDR2 of SEQ ID NO:46, (c) a HCDR3 of SEQ ID NO:47; and a light chain variable region that comprises: (d) a LCDR1 of SEQ ID NO:61, (e) a LCDR2 of SEQ ID NO:62, and (f) a LCDR3 of SEQ ID NO:63.

Embodiments of the present disclosure provide antibody cytokine engrafted proteins comprising: (i) a heavy chain variable region (VH) that comprises SEQ ID NO:19, and a light chain variable region (VL) that comprises SEQ ID NO: 35; or (ii) a heavy chain variable region (VH) that comprises SEQ ID NO: 51, and a light chain variable region (VL) that comprises SEQ ID NO: 67.

The antibody cytokine engrafted protein, wherein the antibody comprises a modified Fe region corresponding with reduced effector function.

The antibody cytokine engrafted protein, wherein the modified Fe region comprises a mutation selected from one or more of D265A, P329A, P329G, N297A, L234A, and L235A.

The antibody cytokine engrafted protein, wherein the modified Fe region comprises a combination of mutations selected from one or more of D265A/P329A, D265A/N297A, L234/L235A, P329A/L234A/L235A, and P329G/L234A/L235A.

Embodiments of the present disclosure provide antibody cytokine engrafted proteins comprising a HCDR1 of SEQ ID NO: 13, a HCDR2 of SEQ ID NO:14, a HCDR3 of SEQ ID NO:15, a LCDR1 of SEQ ID NO:29, a LCDR2 of SEQ ID NO:30, a LCDR3 of SEQ ID NO:31, a modified Fe region containing the mutation D265A/P329A, wherein the antibody cytokine engrafted protein stimulates less activation of Treg cells when compared to recombinant IL2 or PROLEUKIN®.

Embodiments of the present disclosure provide antibody cytokine engrafted proteins comprising a HCDR1 of SEQ ID NO: 45, a HCDR2 of SEQ ID NO:46, a HCDR3 of SEQ ID NO:47, a LCDRI of SEQ ID NO:61, a LCDR2 of SEQ ID NO:62, a LCDR3 of SEQ ID NO:63, a modified Fe region containing the mutation D265A/P329A, wherein the antibody cytokine engrafted protein stimulates less activation of Treg cells when compared to recombinant IL2 or PROLEUKIN®.

Embodiments of the present disclosure provide isolated nucleic acids encoding an antibody cytokine engrafted protein comprising: (i) a heavy chain of SEQ ID NO:22 and/or a light chain of SEQ ID NO:38; or (ii) a heavy chain of SEQ ID NO:54 and/or a light chain of SEQ ID NO:70.

Embodiments of the present disclosure provide recombinant host cells suitable for the production of an antibody cytokine engrafted protein, comprising the nucleic acids disclosed herein encoding the heavy and light chain polypeptides of the protein, and optionally, a secretion signal.

The recombinant host cell, which is a mammalian cell line.

The recombinant host cell, wherein the mammalian cell line is a CHO cell line.

Embodiments of the present disclosure provide pharmaceutical compositions comprising the antibody cytokine engrafted protein disclosed herein and one or more pharmaceutically acceptable carrier.

Embodiments of the present disclosure provide methods of treating cancer in an individual in need thereof, comprising administering to the individual a therapeutically effective amount of the antibody cytokine engrafted protein or the pharmaceutical composition disclosed herein.

The method of treating cancer, wherein the cancer is selected from the group consisting of: melanoma, lung cancer, colorectal cancer, prostate cancer, breast cancer and lymphoma.

The method of treating cancer, wherein the antibody cytokine engrafted protein or the pharmaceutical composition is administered in combination with another therapeutic agent.

The method of treating cancer, wherein the therapeutic agent is another antibody cytokine engrafted protein.

The method of treating cancer, wherein the therapeutic agent is an immune checkpoint inhibitor.

The method of treating cancer, wherein the immune checkpoint is selected from the group consisting of: PD-I, PD-LI, PD-L2, TIM3, CTLA-4, LAG-3, CEACAM-1, CEACAM-5, VISTA, BTLA, TIGIT, LAIRI, CD160, 2B4 and TGFR.

Embodiments of the present disclosure provide methods of expanding CD8+T effector cells in a patient in need thereof, comprising administering the antibody cytokine engrafted protein or the pharmaceutical composition disclosed herein to the patient.

The method of expanding CD8+T effector cells, wherein CD8+T effector cells are expanded and Treg cells are not expanded.

The method of expanding CD8+T effector cells, wherein CD8+T effectors are expanded and NK cells are not expanded.

The method of expanding CD8+T effector cells, further comprising administration of an immune checkpoint inhibitor.

The method of expanding CD8+T effector cells, wherein the immune checkpoint is selected from the group consisting of: PD-I, PD-LI, PD-L2, TIM3, CTLA-4, LAG-3, CEACAM-1, CEACAM-5, VISTA, BTLA, TIGIT, LAIRI, CD160, 2B4 and TGFR.

Embodiments of the present disclosure provide uses of an antibody cytokine engrafted protein in the treatment of cancer comprising: (i) a heavy chain variable region that comprises (a) a HCDRI of SEQ ID NO: 13, (b) a HCDR2 of SEQ ID NO:14, (c) a HCDR3 of SEQ ID NO:15 and a light chain variable region that comprises: (d) a LCDRI of SEQ ID NO:29, (e) a LCDR2 of SEQ ID NO:30, and (f) a LCDR3 of SEQ ID NO:31; and (ii) a heavy chain variable region that comprises (a) a HCDRI of SEQ ID NO:45, (b) a HCDR2 of SEQ ID NO:46, (c) a HCDR3 of SEQ ID NO:47; and a light chain variable region that comprises: (d) a LCDRI of SEQ ID NO:61, (e) a LCDR2 of SEQ ID NO:62, and (f) a LCDR3 of SEQ ID NO:63, in the treatment of cancer.

The use of the antibody cytokine engrafted protein in the treatment of cancer wherein the antibody cytokine engrafted protein is administered in combination with another therapeutic agent.

The use of the antibody cytokine engrafted protein wherein the therapeutic agent is an antagonist of an immune checkpoint inhibitor.

The use wherein the antagonist of the immune checkpoint inhibitor is selected from the group consisting of: PD-I, PD-LI, PD-L2, TIM3, CTLA-4, LAG-3, CEACAM-1, CEACAM-5, VISTA, BTLA, TIGIT, LAIRI, CD160, 2B4 and TGFR.

In certain embodiments, the antibody cytokine engrafted protein comprises an IgG class antibody Fe region. In particular embodiments, the immunoglobulin is selected from IgG1, IgG2, or IgG4 subclass Fe region. The antibody, antibody fragment, or antigen binding molecule optionally contains at least one modification that modulates (i.e., increases or decreases) binding of the antibody or antibody fragment to an Fe receptor. The immunoglobulin heavy chain may optionally comprise a modification conferring modified effector function. In particular embodiments the immunoglobulin heavy chain may comprise a mutation conferring reduced effector function selected from any of D265A, P329A, P329G, N297A, D265A/P329A, D265A/N297A, L234/L235A, P329A/L234A/L235A, and P329G/L234A/L235A.

In some embodiments, the antibody cytokine engrafted protein also comprises variations in the IL2 portion of the molecule. The variations can be single amino acid changes, single amino acid deletions, multiple amino acid changes and multiple amino acid deletions. These changes in the IL2 cytokine portion of the molecule can decrease the affinity of the antibody cytokine engrafted protein for the high-affinity IL2 receptor.

Furthermore, the disclosure provides polynucleotides encoding at least a heavy chain and/or a light chain protein of an antibody cytokine engrafted protein as described herein. In another related aspect, host cells are provided that are suitable for the production of an antibody cytokine engrafted protein as described herein. In particular embodiments, host cells comprise nucleic acids encoding a light chain and/or heavy chain polypeptide of the antibody cytokine engrafted protein. In still another aspect, methods for producing antibody cytokine engrafted proteins are provided, comprising culturing provided host cells as described herein under conditions suitable for expression, formation, and secretion of the antibody cytokine engrafted protein and recovering the antibody cytokine engrafted protein from the culture. In a further aspect, the disclosure further provides kits comprising an antibody cytokine engrafted protein, as described herein.

In another related aspect, the disclosure further provides compositions comprising an antibody cytokine engrafted protein, as described herein, and a pharmaceutically acceptable carrier. In some embodiments, the disclosure provides pharmaceutical compositions comprising an antibody cytokine engrafted protein for administering to an individual.

In another aspect, methods of treating cancer in an individual in need thereof, comprising administering to the individual a therapeutically effective amount of an antibody cytokine engrafted protein, as described herein. In a further aspect, an antibody cytokine engrafted protein for use in treatment or prophylaxis of cancer in an individual is provided.

In some embodiments, the patient has a cell proliferation disorder or cancer, for example, melanoma, lung cancer, colorectal cancer, prostate cancer, breast cancer and lymphoma.

DEFINITIONS

An "antibody" refers to a molecule of the immunoglobulin family comprising a tetrameric structural unit. Each tetramer is composed of two identical pairs of polypeptide chains, each pair having one "light" chain (about 25 kD) and one "heavy" chain (about 50-70 kD), connected through a disulfide bond. Recognized immunoglobulin genes include the K, A, a, y, 8, £, and µ constant region genes, as well as the myriad immunoglobulin variable region genes. Light chains are classified as either K or A. Heavy chains are classified as y, a, 8, or £, which in turn define the immunoglobulin classes, IgG, IgM, IgA, IgD, and IgE, respectively. Antibodies can be of any isotype/class (e.g., IgG, IgM, IgA, IgD, and IgE), or any subclass (e.g., IgGI, IgG2, IgG3, IgG4, IgAI, IgA2).

Both the light and heavy chains are divided into regions of structural and functional homology. The terms "constant" and "variable" are used structurally and functionally. The N-terminus of each chain defines a variable (V) region or domain of about 100 to 110 or more amino acids primarily responsible for antigen recognition. The terms variable light chain (VL) and variable heavy chain (Va) refer to these regions of light and heavy chains respectively. The pairing of a Va and VL together forms a single antigen-binding site. In addition to V regions, both heavy chains and light chains contain a constant (C) region or domain. A secreted form of a immunoglobulin C region is made up of three C domains, CHI, CH2, CH3, optionally CH4 (Cµ), and a hinge region. A membrane-bound form of an immunoglobulin C region also has membrane and intracellular domains. Each light chain has a VL at the N-terminus followed by a constant domain (C) at its other end. The constant domains of the light chain (CL) and the heavy chain (CHI, CH2 or CH3) confer important biological properties such as secretion, transplacental mobility, Fe receptor binding, complement binding, and the like. By convention, the numbering of the constant region domains increases as they become more distal from the antigen binding site or amino-terminus of the antibody. The N-terminus is a variable region and at the C-terminus is a constant region; the CH3 and CL domains actually comprise the carboxy-terminal domains of the heavy and light chain, respectively. The VL is aligned with the VH and the CL is aligned with the first constant domain of the heavy chain. As used herein, an "antibody" encompasses conventional antibody structures and variations of antibodies. Thus, within the scope of this concept are antibody cytokine engrafted proteins, full length antibodies, chimeric antibodies, humanized antibodies, human antibodies, and antibody fragments thereof.

Antibodies exist as intact immunoglobulin chains or as a number of well-characterized antibody fragments produced by digestion with various peptidases. The term "antibody fragment," as used herein, refers to one or more portions of an antibody that retains six CDRs. Thus, for example, pepsin digests an antibody below the disulfide linkages in the hinge region to produce F(ab)' 2, a dimer of Fab' which itself is a light chain joined to Va-Cal by a disulfide bond. The F(ab)'2 may be reduced under mild conditions to break the disulfide linkage in the hinge region, thereby converting the F(ab)'2 dimer into an Fab' monomer. The Fab' monomer is essentially a Fab with a portion of the hinge region (Paul, *Fundamental Immunology* 3d ed. (1993)). While various antibody fragments are defined in terms of the digestion of an intact antibody, one of skill will appreciate that such fragments may be synthesized de novo either chemically or by using recombinant DNA methodology. As used herein, an "antibody fragment" refers to one or more portions of an antibody, either produced by the modification of whole antibodies, or those synthesized de nova using recombinant DNA methodologies, that retain binding specificity and functional activity. Examples of antibody fragments include Fv fragments, single chain antibodies (ScFv), Fab, Fab', Fd (Vh and CHI domains), dAb (Vh and an isolated CDR); and multimeric versions of these fragments (e.g., F(ab')2,) with the same binding specificity. Antibody cytokine engrafted proteins can also comprise antibody fragments necessary to achieve the desired binding specificity and activity.

A "Fab" domain as used in the context comprises a heavy chain variable domain, a constant region CHI domain, a light chain variable domain, and a light chain constant region CL domain. The interaction of the domains is stabilized by a disulfide bond between the CHI and CL domains. In some embodiments, the heavy chain domains of the Fab are in the order, from N-terminus to C-terminus, VH-CH and the light chain domains of a Fab are in the order, from N-terminus to C-terminus, VL-CL. In some embodiments, the heavy chain domains of the Fab are in the order, from N-terminus to C-terminus, CH—VH and the light chain domains of the Fab are in the order CL-VL. Although the Fab fragment was historically identified by papain digestion of an intact immunoglobulin, in the context of this disclosure, a "Fab" is typically produced recombinantly by any method. Each Fab fragment is monovalent with respect to antigen binding, i.e., it has a single antigen-binding site.

"Complementarity-determining domains" or "complementary-determining regions" ("CDRs") interchangeably refer to the hypervariable regions of VL and Va. CDRs are the target protein-binding site of antibody chains that harbor specificity for such target protein. There are three CDRs (CDR1-3, numbered sequentially from the N-terminus) in each human VL or Va, constituting about 15-20% of the variable domains. CDRs are structurally complementary to the epitope of the target protein and are thus directly responsible for the binding specificity. The remaining stretches of the VL or Va, the so-called framework regions (FR), exhibit less variation in amino acid sequence (Kuby, Immunology, 4th ed., Chapter 4. W.H. Freeman & Co., New York, 2000).

Positions of CDRs and framework regions can be determined using various well known definitions in the art, e.g., Kabat, Chothia, and AbM (see, e.g., Kabat et al. 1991 Sequences of Proteins of Immunological Interest, Fifth Edition, U.S. Department of Health and Human Services, NIH Publication No. 91-3242, Johnson et al., Nucleic Acids Res., 29:205-206 (2001); Chothia and Lesk, J. Mol. Biol., 196:901-917 (1987); Chothia et al., Nature, 342:877-883 (1989); Chothia et al., J. Mol. Biol., 227:799-817 (1992); Al-Lazikani et al., J. Mol. Biol., 273:927-748 (1997)). Definitions of antigen combining sites are also described in the following: Ruiz et al., Nucleic Acids Res., 28:219-221 (2000); and Lefranc, M. P., Nucleic Acids Res., 29:207-209 (2001); (ImMunoGenTics (IMGT) numbering) Lefranc, M.-P., The Immunologist, 7, 132-136 (1999); Lefranc, M.-P. et al., Dev. Comp. Immunol., 27, 55-77 (2003); MacCallum et al., J. Mol. Biol., 262:732-745 (1996); and Martin et al., Proc. Natl. Acad. Sci. USA, 86:9268-9272 (1989); Martin et al., Methods Enzymol., 203:121-153 (1991); and Rees et al., In Sternberg M. J. E. (ed.), Protein Structure Prediction, Oxford University Press, Oxford, 141-172 (1996).

Under Kabat, CDR amino acid residues in the Va are numbered 31-35 (HCDR1), 50-65 (HCDR2), and 95-102 (HCDR3); and the CDR amino acid residues in the VL are numbered 24-34 (LCDR1), 50-56 (LCDR2), and 89-97 (LCDR3). Under Chothia, CDR amino acids in the Va are numbered 26-32 (HCDR1), 52-56 (HCDR2), and 95-102 (HCDR3); and the amino acid residues in VL are numbered 26-32 (LCDR1), 50-52 (LCDR2), and 91-96 (LCDR3). By combining the CDR definitions of both Kabat and Chothia, the CDRs consist of amino acid residues 26-35 (HCDR1), 50-65 (HCDR2), and 95-102 (HCDR3) in human VH and amino acid residues 24-34 (LCDRI), 50-56 (LCDR2), and 89-97 (LCDR3) in human VL.

An "antibody variable light chain" or an "antibody variable heavy chain" as used herein refers to a polypeptide comprising the VL or Va, respectively. The endogenous VL is encoded by the gene segments V (variable) and J Gunctional), and the endogenous Va by V, D (diversity), and J. Each of VL or Va includes the CDRs as well as the framework regions (FR). The term "variable region" or "V-region" interchangeably refer to a heavy or light chain comprising FR1-CDR1-FR2-CDR2-FR3-CDR3-FR4. AV-region can be naturally occurring, recombinant or synthetic. In this application, antibody light chains and/or antibody heavy chains may, from time to time, be collectively referred to as "antibody chains." As provided and further described herein, an "antibody variable light chain" or an "antibody variable heavy chain" and/or a "variable region" and/or an "antibody chain" optionally comprises a cytokine polypeptide sequence incorporated into a CDR.

The C-terminal portion of an immunoglobulin heavy chain herein, comprising, e.g., CH2 and CH3 domains, is the "Fe" domain. An "Fe region" as used herein refers to the constant region of an antibody excluding the first constant region (CHI) immunoglobulin domain. Fe refers to the last two constant region immunoglobulin domains of IgA, IgD, and IgG, and the last three constant region immunoglobulin domains of IgE and IgM, and the flexible hinge N-terminal to these domains. For IgA and IgM Fe may include the J chain. For IgG, Fe comprises immunoglobulin domains C'{2 and C'{3 and the hinge between Cyl and Cy. It is understood in the art that boundaries of the Fe region may vary, however, the human IgG heavy chain Fe region is usually defined to comprise residues C226 or P230 to its carboxyl-terminus, using the numbering is according to the EU index as in Kabat et al. (1991, NIH Publication 91-3242, National Technical Information Service, Springfield, Va.). "Fe region" may refer to this region in isolation or this region in the context of an antibody or antibody fragment. "Fe region" includes naturally occurring allelic variants of the Fe region, e.g., in the CH2 and CH3 region, including, e.g., modifications that modulate effector function. Fe regions also include variants that don't result in alterations to biological function. For example, one or more amino acids are deleted from the N-terminus or C-terminus of the Fe region of an immunoglobulin without substantial loss of biological function. For example, in certain embodiments a C-terminal lysine is modified replaced or removed. In particular embodiments one or more C-terminal residues in the Fe region is altered or removed. In certain embodiments one or more C-terminal residues in the Fe (e.g., a terminal lysine) is deleted. In certain other embodiments one or more C-terminal residues in the Fe is substituted with an alternate amino acid (e.g., a terminal lysine is replaced). Such variants are selected according to general rules known in the art so as to have minimal effect on activity (see, e.g., Bowie, et al., Science 247:306-1310, 1990). The Fe domain is the portion of the immunoglobulin (Ig) recognized by cell receptors, such as the FcR, and to which the complement-activating protein, C1 q, binds. The lower hinge region, which is encoded in the 5' portion of the CH2 exon, provides flexibility within the antibody for binding to FcR receptors.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, and drug; or (b) the variable region, or a portion thereof, is altered, replaced or exchanged with a variable region having a different or altered antigen specificity.

A "humanized" antibody is an antibody that retains the reactivity (e.g., binding specificity, activity) of a non-human antibody while being less immunogenic in humans. This can be achieved, for instance, by retaining non-human CDR regions and replacing remaining parts of an antibody with human counterparts. See, e.g., Morrison et al., Proc. Natl. Acad. So. USA, 81:6851-6855 (1984); Morrison and Oi, Adv. Immunal., 44:65-92 (1988); Verhoeyen et al., Science, 239: 1534-1536 (1988); Padlan, Malec. Immun., 28:489-498 (1991); Padlan, Malec. Immun., 31(3):169-217 (1994).

A "human antibody" includes antibodies having variable regions in which both the framework and CDR regions are derived from sequences of human origin. Furthermore, if an antibody contains a constant region, the constant region also is derived from such human sequences, e.g., human germline sequences, or mutated versions of human germline sequences or antibody containing consensus framework sequences derived from human framework sequences analysis, for example, as described in Knappik et al., J. Mol. Biol. 296:57-86, 2000). Human antibodies may include amino acid residues not encoded by human sequences (e.g., mutations introduced by random or site-specific mutagenesis in vitro or by somatic mutation in vivo, or a conservative substitution to promote stability or manufacturing).

The term "corresponding human germline sequence" refers to a nucleic acid sequence encoding a human variable region amino acid sequence or subsequence that shares the highest determined amino acid sequence identity with a reference variable region amino acid sequence or subsequence in comparison to all other all other known variable region amino acid sequences encoded by human germline immunoglobulin variable region sequences. A corresponding human germline sequence can also refer to the human variable region amino acid sequence or subsequence with the highest amino acid sequence identity with a reference variable region amino acid sequence or subsequence in comparison to all other evaluated variable region amino acid sequences. A corresponding human germline sequence can be framework regions only, complementary determining regions only, framework and complementary determining regions, a variable segment (as defined above), or other combinations of sequences or sub-sequences that comprise a variable region. Sequence identity can be determined using the methods described herein, for example, aligning two sequences using BLAST, ALIGN, or another alignment algorithm known in the art. The corresponding human germline nucleic acid or amino acid sequence can have at least about 90%, 91%, 92%, 93%, 94%, 95%, 96%, 97%, 98%, 99%, or 100% sequence identity with the reference variable region nucleic acid or amino acid sequence.

The term "valency" as used herein refers to the number of potential target binding sites in a polypeptide. Each target binding site specifically binds one target molecule or a specific site on a target molecule. When a polypeptide comprises more than one target binding site, each target binding site may specifically bind the same or different molecules (e.g., may bind to different molecules, e.g., different antigens, or different epitopes on the same molecule). A conventional antibody, for example, has two binding sites and is bivalent; "trivalent" and "tetravalent" refer to the presence of three binding sites and four binding sites, respectively, in an antibody molecule. The antibody cytokine engrafted proteins can be monovalent (i.e., bind one target molecule), bivalent, or multivalent (i.e., bind more than one target molecule).

The phrase "specifically binds" or "binding specificity" when used in the context of describing the interaction between a target (e.g., a protein) and an antibody cytokine engrafted protein, refers to a binding reaction that is determinative of the presence of the target in a heterogeneous population of proteins and other biologics, e.g., in a biological sample, e.g., a blood, serum, plasma or tissue sample. Thus, under certain designated conditions, an antibody cytokine engrafted protein with a particular binding specificity binds to a particular target at least two times the background and do not substantially bind in a significant amount to other targets present in the sample. In one embodiment, under designated conditions, an antibody cytokine engrafted protein with a particular binding specificity bind to a particular antigen at least ten (10) times the background and do not substantially bind in a significant amount to other targets present in the sample. Specific binding to an antibody cytokine engrafted protein under such conditions can require an antibody cytokine engrafted protein to have been selected for its specificity for a particular target protein. As used herein, specific binding includes antibody cytokine engrafted proteins that selectively bind to human IL2 low affinity receptor and do not include antibody cytokine engrafted proteins that cross-react with, e.g., other cytokine receptor superfamily members. In some embodiments, antibody cytokine engrafted proteins are selected that selectively bind to human IL2 low affinity receptor and cross-react with non-human primate IL2R (e.g., cynomolgus IL2R). In some embodiments, antibody engrafted proteins are selected that selectively bind to human IL2 low affinity receptor and react with an additional target. A variety of formats may be used to select antibody cytokine engrafted proteins that are specifically reactive with a particular target protein. For example, solid-phase ELISA immunoassays are routinely used to select antibodies specifically immunoreactive with a protein (see, e.g., Harlow & Lane, Using Antibodies, A Laboratory Manual (1998), for a description of immunoassay formats and conditions that can be used to determine specific immunoreactivity). Typically a specific or selective binding reaction will produce a signal at least twice over the background signal and more typically at least than 10 to 100 times over the background.

The term "equilibrium dissociation constant (Ko, M)" refers to the dissociation rate constant (kct, time$^{-1}$) divided by the association rate constant (ka, time-1, M$^{-1}$) Equilibrium dissociation constants can be measured using any known method in the art. The antibody cytokine engrafted proteins generally will have an equilibrium dissociation constant of less than about 10-$^{7}$ or 10-$^{8}$ M, for example, less than about 10-$^{9}$ M or 10-$^{10}$ M, in some embodiments, less than about 10-$^{11}$ M, 10-$^{12}$ M or 10-$^{13}$ M.

As used herein, the term "epitope" or "binding region" refers to a domain in the antigen protein that is responsible for the specific binding between the antibody CDRs and the antigen protein.

As used herein, the term "receptor-cytokine binding region" refers to a domain in the engrafted cytokine portion of the antibody cytokine engrafted protein that is responsible for the specific binding between the engrafted cytokine and its receptor (e.g. the IL2 low affinity receptor). There is at least one such receptor-cytokine binding region present in each antibody cytokine engrafted protein, and each of the binding regions may be identical or different from the others.

The term "agonist" interchangeably refers to an antibody capable of activating a receptor to induce a full or partial receptor-mediated response. For example, an agonist of the IL2 low affinity receptor binds to the IL2 low affinity receptor and induces IL2-mediated intracellular signaling, cell activation and/or proliferation of CD8+T effector cells and NK cells. The antibody cytokine engrafted protein agonist stimulates signaling through the IL low affinity receptor similarly in some respects to the native IL2 ligand. The binding of IL2 to IL2 low affinity receptor induces Jak1 and Jak2 activation which results in STATS phosphorylation. In some embodiments, an antibody cytokine engrafted protein agonist can be identified by its ability to bind IL2 low affinity receptor and induce STATS phosphorylation, and/or proliferation of CD8+T effector cells or NK cells.

The term "IL2" or "interleukin 2" or "interleukin-2" or "IL-2", interchangeably, refer to an alpha helical cytokine family member wherein the native protein functions in the regulation and maintenance of inflammatory processes. A property of IL2 is that the N and C-termini are close to each other in space, which make the IL2 cytokine protein suitable for antibody grafting. IL2 comprising residues 21-153 of full length native human is utilized in the context of the agonist antibody cytokine engrafted proteins. The human IL2 as disclosed herein has over its full length at least about 90%, 91%, 92%, 93%, 94%, 95%, 96%, 97%, 9S %, 99%, or 100% sequence identity with the amino acid SEQ ID NO:2, and retains preferential agonist activity of the antibody cytokine engrafted proteins as described herein and has been published as GenBank Accession No: NP_000577. SEQ ID NO:1 is the human IL2 cDNA sequence. The human IL2 nucleic acid encoding for the IL2 protein as disclosed herein has over its full length at least about 90%, 91%, 92%, 93%, 94%, 95%, 96%, 97%, 9S %, 99%, or 100% sequence identity with the nucleic acid sequence of SEQ ID NO:1, and was published under GenBank Accession No: NM_000556.

The term "antibody cytokine engrafted protein" or "antibody cytokine graft" or "engrafted" means that at least one cytokine is incorporated directly within a CDR of the antibody, interrupting the sequence of the CDR. The cytokine can be incorporated within HCDR1, HCDR2, HCDR3, LCDR1, LCDR2 or LCDR3. The cytokine can be incorporated within HCDR1, HCDR2, HCDR3, LCDR1, LCDR2 or LCDR3 and incorporated toward the N-terminal sequence of the CDR or toward the C-terminal sequence of the CDR. The cytokine incorporated within a CDR can disrupt the specific binding of the antibody portion to the original target protein or the antibody cytokine engrafted protein can retain its specific binding to its target protein. Exemplary cytokines include, but are not limited to; IL-1a, IL-1 IL-2, IL-3, IL-4, IL-5, IL-6, IL-7, IL-8, IL-12, IFN-a, IFN-, IFN-y, GM-CSF, MIP-1a, MIP-1, TGF-, TNF-α, and TNF-. It is also possible to engraft a cytokine into a specific CDR of one "arm" of the antibody and to engraft another, different cytokine into a CDR of the other "arm" of the antibody. For example, engrafting IL2 into the HCDRI of one "arm" of the antibody and engrafting IL-7 into the LCDRI of the other "arm" of the antibody cytokine engrafted protein, can create a dual function antibody cytokine engrafted protein.

The term "isolated," when applied to a nucleic acid or protein, denotes that the nucleic acid or protein is essentially free of other cellular components with which it is associated in the natural state. It is preferably in a homogeneous state. It can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. In particular, an isolated gene is separated from open reading frames that flank the gene and encode a protein other than the gene of interest. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., *J. Biol. Chem.* 260:2605-2608 (1985); and Rossolini et al., *Mal. Cell. Probes* 8:91-98 (1994)).

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and 0-phosphoserine. Amino acid analogs refer to compounds that have the same basic chemical structure as a naturally occurring amino acid, i.e., an a-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG, and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles. The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (e.g., a polypeptide), which does not comprise additions or deletions, for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same sequences. Two sequences are "substantially identical" if two sequences have a specified percentage of amino acid residues or nucleotides that are the same (i.e., at least 85%, 90%, 91%, 92%, 93%, 94%, 95%, 96%, 97%, 98%, 99% or 100% sequence identity over a specified region, or, when not specified, over the entire sequence of a reference sequence), when compared and aligned for maximum correspondence over a comparison window, or designated region as measured using one of the following sequence comparison algorithms or by manual alignment and visual inspection. The disclosure provides polypeptides or polynucleotides that are substantially identical to the polypeptides or polynucleotides, respectively, exemplified herein (e.g., the variable regions exemplified in any one of SEQ ID NO:19, SEQ ID NO:35, SEQ ID NO:51, or SEQ ID NO:67. The identity exists over a region that is at least about 15, 25 or 50 nucleotides in length, or more preferably over a region that is 100 to 500 or 1000 or more nucleotides in length, or over the full length of the reference sequence. With respect to amino acid sequences, identity or substantial identity can exist over a region that is at least 5, 10, 15 or 20 amino acids in length, optionally at least about 25, 30, 35, 40, 50, 75 or 100 amino acids in length, optionally at least about 150, 200 or 250 amino acids in length, or over the full length of the reference sequence. With respect to shorter amino acid sequences, e.g., amino acid sequences of 20 or fewer amino acids, substantial identity exists when one or two amino acid residues are conservatively substituted, according to the conservative substitutions defined herein.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mal. Biol.* 48:443, by the search for similarity method of Pearson and Lipman (1988) *Proc. Nat'l. Acad. Sci. USA* 85:2444, by computerized implementations of these algorithms (GAP, BESTFIT, PASTA, and TFASTA in the Wisconsin Genetics Software Package, Genetics Computer Group, 575 Science Dr., Madison, WI), or by manual alignment and visual inspection (see, e.g., Ausubel et al., *Current Protocols in Molecular Biology* (1995 supplement)).

Two examples of algorithms that are suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mal. Biol.* 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "link," when used in the context of describing how the binding regions are connected within an antibody cytokine engrafted protein of this invention, encompasses all possible means for physically joining the regions. The multitude of binding regions are frequently joined by chemical bonds such as a covalent bond (e.g., a peptide bond or a disulfide bond) or a non-covalent bond, which can be either a direct bond (i.e., without a linker between two binding regions) or indirect bond (i.e., with the aid of at least one linker molecule between two or more binding regions).

The terms "subject," "patient," and "individual" interchangeably refer to a mammal, for example, a human or a non-human primate mammal. The mammal can also be a laboratory mammal, e.g., mouse, rat, rabbit, hamster. In some embodiments, the mammal can be an agricultural mammal (e.g., equine, ovine, bovine, porcine, camelid) or domestic mammal (e.g., canine, feline).

As used herein, the terms "treat," "treating," or "treatment" of any disease or disorder refer in one embodiment, to ameliorating the disease or disorder (i.e., slowing or arresting or reducing the development of the disease or at least one of the clinical symptoms thereof). In another embodiment, "treat," "treating," or "treatment" refers to alleviating or ameliorating at least one physical parameter including those which may not be discernible by the patient. In yet another embodiment, "treat," "treating," or "treatment" refers to modulating the disease or disorder, either physically, (e.g., stabilization of a discernible symptom), physiologically, (e.g., stabilization of a physical parameter), or both. In yet another embodiment, "treat," "treating," or "treatment" refers to preventing or delaying the onset or development or progression of a disease or disorder.

The term "therapeutically acceptable amount" or "therapeutically effective dose" interchangeably refer to an amount sufficient to effect the desired result (i.e., a reduction in inflammation, inhibition of pain, prevention of inflammation, inhibition or prevention of inflammatory response). In some embodiments, a therapeutically acceptable amount does not induce or cause undesirable side effects. A therapeutically acceptable amount can be determined by first administering a low dose, and then incrementally increasing that dose until the desired effect is achieved. A "prophylactically effective dosage," and a "therapeutically effective dosage," of an IL2 antibody cytokine engrafted protein can prevent the onset of, or result in a decrease in severity of, respectively, disease symptoms, including symptoms associated with cancer and cancer treatment.

The term "co-administer" refers to the simultaneous presence of two (or more) active agents in an individual. Active agents that are co-administered can be concurrently or sequentially delivered.

As used herein, the phrase "consisting essentially of" refers to the genera or species of active pharmaceutical agents included in a method or composition, as well as any inactive carrier or excipients for the intended purpose of the methods or compositions. In some embodiments, the phrase "consisting essentially of" expressly excludes the inclusion of one or more additional active agents other than an IL2 antibody cytokine engrafted protein. In some embodiments, the phrase "consisting essentially of" expressly excludes the inclusion of more additional active agents other than an IL2 antibody cytokine engrafted protein and a second co-administered agent.

The terms "a," "an," and "the" include plural referents, unless the context clearly indicates otherwise.

BRIEF DESCRIPTION OF THE DRAWINGS

FIG. 1 is a table summarizing exemplary the IL2 antibody cytokine engrafted proteins and their activities on CD8+T effector cells.

FIG. 4B shows a table depicting the increased activity of IgG.IL2R67A.HI and IgGIL2F71A.H1 on CD8+T effectors in NOD mice.

FIG. 7 shows a graph with values monitoring pSTAT5 activity in a panel of human cells comparing IgG.IL2R67A.HI and IgG.IL2F71A.H1 with PROLEUKIN®.

ANTIBODY CYTOKINE ENGRAFTED PROTEINS TARGETING THE IL2 LOW AFFINITY RECEPTOR

Figure 2:
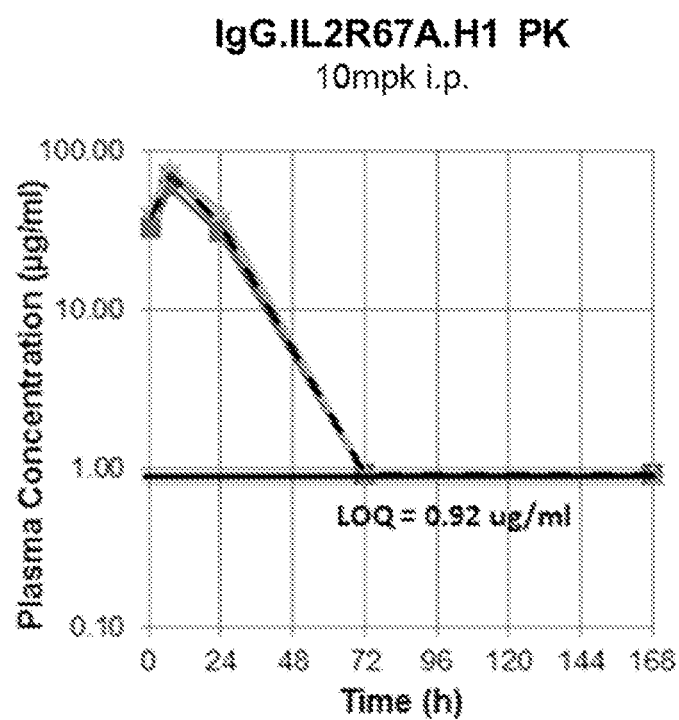
FIG. 2 shows that IgG.IL2R67A.HI has a greater half-life than that of PROLEUKIN®. IgG.IL2R67A.HI has a half-life of 12-14 hours as shown in the graph, while PROLEUKIN® has a T1/2 of less than 4 hours and cannot be shown on the graph.

Provided herein are protein constructs comprising an IL2 molecule engrafted to into the complementarity determining region (CDR) of an antibody. The antibody cytokine engrafted proteins of the present disclosure show suitable properties to be used in human patients, for example, they retain immunostimulatory activity similar to that of native or recombinant human IL2. However, the negative effects are diminished. For example, there is less stimulation of Treg cells. Other activities and characteristics are also demonstrated throughout the specification. Thus, provided are antibody cytokine engrafted proteins having an improved therapeutic profile over previously known IL2 and modified IL2 therapeutic agents such as PROLEUKIN®, and methods of use of the provided antibody cytokine engrafted proteins in cancer treatment.

Accordingly, the present disclosure provides antibody cytokine engrafted proteins that are agonists of the IL2 low affinity receptor, with selective activity profiles. Provided antibody cytokine engrafted proteins comprise an immunoglobulin heavy chain sequence and an immunoglobulin light chain sequence. Each immunoglobulin heavy chain sequence comprises a heavy chain variable region (VH) and a heavy chain constant region (CH), wherein the heavy chain constant region consists of CHI, CH2, and CH3 constant regions. Each immunoglobulin light chain sequence comprises a light chain variable region (VL) and a light chain constant region (CL). In each antibody cytokine engrafted protein an IL2 molecule is incorporated into a complementarity determining region (CDR) of the VH or VL.

In some embodiments, the antibody cytokine engrafted protein comprises an IL2 molecule incorporated into a heavy chain CDR. In certain embodiments the IL2 molecule is incorporated into heavy chain complementarity determining region 1 (HCDR1). In certain embodiments the IL2 molecule is incorporated into heavy chain complementarity determining region 2 (HCDR2). In certain embodiments the IL2 molecule is incorporated into heavy chain complementarity determining region 3 (HCDR3).

In some embodiments, the antibody cytokine engrafted protein comprises an IL2 molecule incorporated into a light chain CDR. In certain embodiments the IL2 molecule is incorporated into light chain complementarity determining region 1 (LCDRI). In certain embodiments the IL2 molecule is incorporated into light chain complementarity determining region 2 (LCDR2). In certain embodiments the IL2 molecule is incorporated into light chain complementarity determining region 3 (LCDR3).

In some embodiments, the antibody cytokine engrafted comprises an IL2 sequence incorporated into a CDR, whereby the IL2 sequence is inserted into the CDR sequence. The insertion can be at or near the N-terminal region of the CDR, in the middle region of the CDR or at or near the C-terminal region of the CDR. In other embodiments, the antibody cytokine engrafted comprises an IL2 molecule incorporated into a CDR, whereby the IL2 sequence does not frameshift the CDR sequence. In other embodiments, the antibody cytokine engrafted comprises an IL2 molecule incorporated into a CDR, whereby the IL2 sequence replaces all or part of a CDR sequence. A replacement can be the N-terminal region of the CDR, in the middle region of the CDR or at or near the C-terminal region the CDR. A replacement can be as few as one or two amino acids of a CDR sequence, or the entire CDR sequence.

In some embodiments an IL2 molecule is engrafted directly into a CDR without a peptide linker, with no additional amino acids between the CDR sequence and the IL2 sequence.

In some embodiments antibody cytokine engrafted proteins comprise immunoglobulin heavy chains of an IgG class antibody heavy chain. In certain embodiments an IgG heavy chain is any one of an IgG1, an IgG2 or an IgG4 subclass.

In some embodiments antibody cytokine engrafted proteins comprise heavy and light chain immunoglobulin sequences selected from a known, clinically utilized immunoglobulin sequence. In certain embodiments antibody cytokine engrafted proteins comprise heavy and light chain immunoglobulin sequences which are humanized sequences. In other certain embodiments antibody cytokine engrafted proteins comprise heavy and light chain immunoglobulin sequences which are human sequences.

In some embodiments antibody cytokine engrafted proteins comprise heavy and light chain immunoglobulin sequences selected from germline immunoglobulin sequences.

In some embodiments antibody cytokine engrafted proteins comprise heavy and light chain immunoglobulin sequences having binding specificity of the immunoglobulin variable domains to a target distinct from the binding specificity of the IL2 molecule. In some embodiments the binding specificity of the immunoglobulin variable domain to its target is retained by 10%, 20%, 30%, 40%, 50%, 60%, 70%, 80%, 90%, 95%, 98%, 99%, or 100%, in the presence of the engrafted cytokine. In certain embodiments the retained binding specificity is to a non-human target. In certain embodiments the retained binding specificity it to a virus, for example, RSV. In other embodiments the binding specificity is to a human target having therapeutic utility in conjunction with an IL2 therapy. In certain embodiments, targeting the binding specificity of the immunoglobulin conveys additional therapeutic benefit to the IL2 component. In certain embodiments the binding specificity of the immunoglobulin to its target conveys synergistic activity with IL2.

In still other embodiments, the binding specificity of the immunoglobulin is reduced by 10%, 20%, 30%, 40%, 50%, 60%, 70%, 80%, 90%, 95%, 98%, 99%, or 100%, by the engrafting of the IL2 molecule.

Provided antibody cytokine engrafted proteins comprise an IL2 molecule engrafted into a complementarity determining region (CDR) of the VH or VL. In some embodiments, the IL2 sequence has at least 85%, 89%, 90%, 91%, 92%, 93%, 94%, 95%, 96%, 97%, 98%, 99% or 100% sequence identity to the amino acid sequence of SEQ ID NO:4. In some embodiments, the IL2 molecule comprises the sequence of SEQ ID NO:4. In some embodiments, the IL2 molecule consists of the sequence of SEQ ID NO:4.

Provided antibody cytokine engrafted proteins comprise an IL2 molecule engrafted into a complementarity determining region (CDR) of the VH or VL. In some embodiments, the IL2 sequence has at least 85%, 89%, 90%, 91%, 92%, 93%, 94%, 95%, 96%, 97%, 98%, 99% or 100% sequence identity to the amino acid sequence of SEQ ID NO:6. In some embodiments, the IL2 molecule comprises the sequence of SEQ ID NO:6. In some embodiments, the IL2 molecule consists of the sequence of SEQ ID NO:6.

In some embodiments, the antibody cytokine engrafted protein confers pro immunomodulatory properties superior to human IL2, recombinant human IL2, PROLEUKIN® or IL2 fused to an Fe. The antibody cytokine engrafted protein confers increased activity on CD8+T effector cells while providing reduced Treg activity as compared to human IL2, recombinant human IL2, PROLEUKIN® or IL2 fused to an Fe.

In some embodiments, the antibody cytokine engrafted proteins comprise a modified immunoglobulin IgG having a modified Fe conferring modified effector function. In certain embodiments the modified Fe region comprises a mutation selected from one or more of D265A, P329A, P329G, N297A, L234A, and L235A. In particular embodiments the immunoglobulin heavy chain may comprise a mutation or combination of mutations conferring reduced effector function selected from any of D265A, P329A, P329G, N297A, D265A/P329A, D265A/N297A, L234/L235A, P329A/L234A/L235A, and P329G/L234A/L235A.

In some embodiments, the antibody cytokine engrafted proteins comprise (i) a heavy chain variable region having at least 85%, 89%, 90%, 91%, 92%, 93%, 94%, 95%, 96%, 97%, 98%, 99%, or 100% amino acid sequence identity to a heavy chain variable region of SEQ ID NO:19 and (ii) a light chain variable region having at least 85%, 89%, 90%, 91%, 92%, 93%, 94%, 95%, 96%, 97%, 98%, 99%, or 100% amino acid sequence identity to a light chain variable region of SEQ ID NO:35. The immunoglobulin chain is an IgG class selected from IgG1, IgG2, or IgG4. In certain embodiments the immunoglobulin optionally comprises a mutation or combination of mutations conferring reduced effector function selected from any of D265A, P329A, P329G, N297A, D265A/P329A, D265A/N297A, L234/L235A, P329A/L234A/L235A, and P329G/L234A/L235A.

In some embodiments, the antibody cytokine engrafted proteins comprise (i) a heavy chain variable region having at least 85%, 89%, 90%, 91%, 92%, 93%, 94%, 95%, 96%, 97%, 98%, 99%, or 100% amino acid sequence identity to a heavy chain variable region of SEQ ID NO:51 and (ii) a light chain variable region having at least 85%, 89%, 90%, 91%, 92%, 93%, 94%, 95%, 96%, 97%, 98%, 99%, or 100% amino acid sequence identity to a light chain variable region of SEQ ID NO:67. The immunoglobulin chain is an IgG class selected from IgG1, IgG2, or IgG4. In certain embodiments the immunoglobulin optionally comprises a mutation or combination of mutations conferring reduced effector function selected from any of D265A, P329A, P329G, N297A, D265A/P329A, D265A/N297A, L234/L235A, P329A/L234A/L235A, and P329G/L234A/L235A.

Engineered and Modified Antibody Cytokine Engrafted Proteins

In certain aspects, antibody cytokine engrafted constructs are generated by engrafting an IL2 sequence into a CDR region of an immunoglobulin scaffold. Both heavy and light chain immunoglobulin chains are produced to generate final antibody engrafted proteins. Antibody cytokine engrafted proteins confer preferred therapeutic activity on CD8+T effector cells, and the antibody cytokine engrafted proteins have reduced Treg activity as compared with native or recombinant human IL2 (rhIL2 or PROLEUKIN®) or IL2 fused to an Fe.

To engineer antibody cytokine engrafted proteins, IL2 sequences containing specific muteins (SEQ ID NO:4 or SEQ ID NO:6), are inserted into a CDR loop of an immunoglobulin chain scaffold protein. Engrafted constructs can be prepared using any of a variety of known immunoglobulin sequences which have been utilized in clinical settings, known immunoglobulin sequences which are in current discovery and/or clinical development, human germline antibody sequences, as well as sequences of novel antibody immunoglobulin chains. Constructs are produced using standard molecular biology methodology utilizing recombinant DNA encoding relevant sequences. Sequences of IL2 in an exemplary scaffold, referred to as GFTX3b, are depicted in TABLE 2. Insertion points were selected to be the mid-point of the loop based on available structural or homology model data, however, insertion points can be adjusted toward the Nor C-terminal end of the CDRloop.

Thus the present disclosure provides antibodies or fragments thereof that specifically bind to the low affinity IL2 receptor comprising an IL2 protein recombinantly inserted into a heterologous antibody protein or polypeptide to generate engrafted proteins. In particular, the disclosure provides engrafted proteins comprising an antibody or antigen-binding fragment of an antibody described herein or any other relevant scaffold antibody polypeptide (e.g., a full antibody immunoglobulin protein, a Fab fragment, Fe fragment, Fv fragment, F(ab)2 fragment, a VH domain, a VH CDR, a VL domain, a VL CDR, etc.) and a heterologous cytokine protein, polypeptide, or peptide, e.g., IL2. Methods for fusing or conjugating proteins, polypeptides, or peptides to an antibody or an antibody fragment are known in the art. See, e.g., U.S. Pat. Nos. 5,336,603, 5,622,929, 5,359,046, 5,349,053, and 5,112,946; European Patent Nos. EP 307,434 and EP 367,166; International Publication Nos. WO 96/04388 and WO 91/06570; Ashkenazi et al., 1991, Proc. Natl. Acad. Sci. USA 88: 10535-10539; Zheng et at, 1995, J. Immunol. 154:5590-5600; and Vil et al., 1992, Proc. Natl. Acad. Sci. USA 89:11337-11341. Additionally, antibody cytokine engrafted proteins may be generated through the techniques of gene-shuffling, motif-shuffling, exon-shuffling, and/or codon-shuffling (collectively referred to as "DNA shuffling"). DNA shuffling may be employed to prepare engrafted protein constructs and/or to alter the activities of antibodies or fragments thereof (e.g., antibodies or fragments thereof with higher affinities and lower dissociation rates). See, generally, U.S. Pat. Nos. 5,811,238, 5,830,721, 5,834,252, and 5,837,458; Patten et al., 1997, Curr. Opinion Biotechnol. 8:724-33; Harayama, 1998, Trends Biotechnol. 16(2):76-82; Hansson, et al., 1999, J. Mol. Biol. 287:265-76; and Lorenzo and Blasco, 1998, Biotechniques 24(2):308-313. Antibodies or fragments thereof, or the encoded antibodies or fragments thereof, may be altered by being subjected to random mutagenesis by error-prone PCR, random nucleotide insertion or other methods prior to recombination. A polynucleotide encoding an antibody or fragment thereof that specifically binds to an antigen protein of interest may be recombined with one or more components, motifs, sections, parts, domains, fragments, etc. of one or more heterologous cytokine molecules, e.g., IL2, for preparation of antibody cytokine engrafted proteins as provided herein.

An antibody Fab contains six CDR loops, 3 in the light chain (CDRL1, CDRL2, CDRL3) and 3 in the heavy chain (CDRH1, CDRH2, CDRH3) which can serve as potential insertion sites for a cytokine protein. Structural and functional considerations are taken into account in order to determine which CDR loop(s) to insert the cytokine. As a CDR loop size and conformation vary greatly across different antibodies, the optimal CDR for insertion can be determined empirically for each particular antibody/protein combination. Additionally, since a cytokine protein will be inserted into a CDR loop, this can put additional constraints on the structure of the cytokine protein as discussed in Example 1.

CDRs of immunoglobulin chains are determined by well-known numbering systems known in the art, including those described herein. For example, CDRs have been identified and defined by (1) using the numbering system described in Kabat et al. (1991), "Sequences of Proteins of Immunological Interest," 5th Ed. Public Health Service, National Institutes of Health, Bethesda, MD ("Kabat" numbering scheme), NIH publication No. 91-3242; and (2) Chothia, see Al-Lazikani et al., (1997) "Standard conformations for the canonical structures of immunoglobulins," J. Mol. Biol. 273:927-948. For identified CDR amino acid sequences less than 20 amino acids in length, one or two conservative amino acid residue substitutions can be tolerated while still retaining the desired specific binding and/or agonist activity.

An antibody cytokine engrafted protein further can be prepared using an antibody having one or more of the CDRs and/or VH and/or VL sequences shown herein (e.g., TABLE 2) as starting material to engineer a modified antibody cytokine engrafted protein, which may have altered properties from the starting antibody engrafted protein. Alternatively any known antibody sequences may be utilized as a scaffold to engineer modified antibody cytokine engrafted protein. For example, any known, clinically utilized antibody may be utilized as a starting materials scaffold for preparation of antibody engrafted protein. Known antibodies and corresponding immunoglobulin sequences include, e.g., palivizumab, alirocumab, mepolizumab, necitumumab, nivolumab, dinutuximab, secukinumab, evolocumab, blinatumomab, pembrolizumab, ramucirumab vedolizumab, siltuximab, obinutuzumab, trastuzumab, raxibacumab, pertuzumab, belimumab, ipilimumab, denosumab, tocilizumab, ofatumumab, canakinumab, golimumab, ustekinumab, certolizumab, catumaxomab, eculizumab, ranibizumab, panitumumab, natalizumab, bevacizumab, cetuximab, efalizumab, omalizumab, tositumomab, ibritumomab tiuxetan, adalimumab, alemtuzumab, gemtuzumab, infliximab, basiliximab, daclizumab, rituximab, abciximab, muromonab, or modifications thereof. Known antibodies and immunoglobulin sequences also include germline antibody sequences. Framework sequences can be obtained from public DNA databases or published references that include germline antibody gene sequences. For example, germline DNA sequences for human heavy and light chain variable region genes can be found in the "VBase" human germline sequence database, as well as in Kabat, E. A., et al., 1991 Sequences of Proteins of Immunological Interest, Fifth Edition, U.S. Department of Health and Human Services, NIH Publication No. 91-3242; Tomlinson, I. M., et al., 1992 J. fol. Biol. 227:776-798; and Cox, J. P. L. et al., 1994 Eur. J Immunol. 24:827-836. In still other examples, antibody and corresponding immunoglobulin sequences from other known entities which can be in early discovery and/or drug development can be similarly adapted as starting material to engineer a modified antibody cytokine engrafted protein.

A wide variety of antibody/immunoglobulin frameworks or scaffolds can be employed so long as the resulting polypeptide includes at least one binding region which accommodates incorporation of a cytokine (e.g., IL2). Such frameworks or scaffolds include the 5 main idiotypes of human immunoglobulins, or fragments thereof, and include immunoglobulins of other animal species, preferably having humanized and/or human aspects. Novel antibodies, frameworks, scaffolds and fragments continue to be discovered and developed by those skilled in the art.

Antibodies can be generated using methods that are known in the art. For preparation of monoclonal antibodies, any technique known in the art can be used (see, e.g., Kohler & Milstein, *Nature* 256:495-497 (1975); Kozbor et al., *Immunology Today* 4:72 (1983); Cole et al., Monoclonal Antibodies and Cancer Therapy, pp. 77-96. Alan R. Liss, Inc. 1985). Techniques for the production of single chain antibodies (U.S. Pat. No. 4,946,778) can be adapted to produce antibodies for use in antibody cytokine engrafted proteins. Also, transgenic mice, or other organisms such as other mammals, can be used to express and identify primatized or humanized or human antibodies. Alternatively, phage display technology can be used to identify antibodies and heteromeric Fab fragments that specifically bind to selected antigens for use in antibody cytokine engrafted proteins (see, e.g., McCafferty et al., supra; Marks et al., *Biotechnology*, 10:779-783, (1992)).

Methods for primatizing or humanizing non-human antibodies are well known in the art. Generally, a primatized or humanized antibody has one or more amino acid residues introduced into it from a source which is non-primate or non-human. Such non-primate or non-human amino acid residues are often referred to as import residues, which are typically taken from an import variable domain. Humanization can be essentially performed following the method of Winter and co-workers (see, e.g., Jones et al., *Nature* 321: 522-525 (1986); Riechmann et al., *Nature* 332:323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, primatized or humanized antibodies are typically primate or human antibodies in which some complementary determining region ("CDR") residues and possibly some framework ("FR") residues are substituted by residues from analogous sites in an originating species (e.g., rodent antibodies) to confer binding specificity.

Alternatively or additionally, an in vivo method for replacing a nonhuman antibody variable region with a human variable region in an antibody while maintaining the same or providing better binding characteristics relative to that of the nonhuman antibody may be utilized to convert non-human antibodies into engineered human antibodies. See, e.g., U.S. Patent Publication No. 20050008625, U.S. Patent Publication No. 2005/0255552. Alternatively, human V segment libraries can be generated by sequential cassette replacement in which only part of the reference antibody V segment is initially replaced by a library of human sequences; and identified human "cassettes" supporting binding in the context of residual reference antibody amino acid sequences are then recombined in a second library screen to generate completely human V segments (see, U.S. Patent Publication No. 2006/0134098).

Various antibodies or antigen-binding fragments for use in preparation of antibody cytokine engrafted proteins can be produced by enzymatic or chemical modification of the intact antibodies, or synthesized de novo using recombinant DNA methodologies (e.g., single chain Fv), or identified using phage display libraries (see, e.g., McCafferty et al., *Nature* 348:552-554, 1990). For example, minibodies can be generated using methods described in the art, e.g., Vaughan and Sollazzo, Comb. Chem. High Throughput Screen 4:417-30 2001. Bispecific antibodies can be produced by a variety of methods including engrafted of hybridomas or linking of Fab' fragments. See, e.g., Songsivilai & Lachmann, Clin. Exp. Immunol. 79:315-321 (1990); Kostelny et al., J. Immunol. 148, 1547-1553 (1992). Single chain antibodies can be identified using phage display libraries or ribosome display libraries, gene shuffled libraries. Such libraries can be constructed from synthetic, semi-synthetic or native and immunocompetent sources. Selected immunoglobulin sequences may thus be utilized in preparation of antibody cytokine engrafted protein constructs as provided herein.

Antibodies, antigen-binding molecules or antibody cytokine engrafted molecules of use in the present disclosure further include bispecific antibodies. A bispecific or bifunctional antibody is an artificial hybrid antibody having two different heavy/light chain pairs and two different binding sites. Other antigen-binding fragments or antibody portions include bivalent scFv (diabody), bispecific scFv antibodies where the antibody molecule recognizes two different epitopes, single binding domains (dAbs), and minibodies. Selected immunoglobulin sequences may thus be utilized in preparation of antibody cytokine engrafted protein constructs as provided herein.

Antigen-binding fragments of antibodies e.g., a Fab fragment, scFv, can be used as building blocks to construct antibody cytokine engrafted proteins, and may optionally include multivalent formats. In some embodiments, such multivalent molecules comprise a constant region of an antibody (e.g., Fc).

Antibody cytokine engrafted proteins can be engineered by modifying one or more residues within one or both variable regions (i.e., VH and/or VL) of an antibody, for example, within one or more CDR regions, and such adapted VH and/or VL region sequences are utilized for engrafting a cytokine or for preparation of cytokine engrafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. CDR sequences are responsible for most antibody-antigen interactions, it is possible to express recombinant antibodies that mimic the properties of a specific antibody by constructing expression vectors that include CDR sequences from a specific antibody grafted onto framework sequences from a different antibody with different properties (see, e.g., Riechmann, L. et al., 1998 Nature 332:323-327; Jones, P. et al., 1986 Nature 321:522-525; Queen, C. et al., 1989 Proc. Natl. Acad., U.S.A. 86:10029-10033; U.S. Pat. No. 5,225,539 to Winter, and U.S. Pat. Nos. 5,530,101; 5,585,089; 5,693,762 and 6,180,370 to Queen et at). In certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al).

In some aspects mutation of amino acid residues within the VH and/or VL CDR1, CDR2, and/or CDR3 regions to thereby improve one or more binding properties (e.g., affinity) of the antibody of interest, known as "affinity maturation," may be beneficial, e.g., to optimize antigen binding of an antibody in conjunction with the context of the cytokine engrafted protein. Site-directed mutagenesis or PCR-mediated mutagenesis can be performed to introduce the mutation(s) and the effect on antibody binding, or other functional property of interest, can be evaluated in in vitro or in vivo assays as described herein and/or alternative or additional assays known in the art. Conservative modifications can be introduced. The mutations may be amino acid substitutions, additions or deletions. Moreover, typically no more than one, two, three, four or five residues within a CDR region are altered.

Engineered antibodies or antibody fragments include those in which modifications have been made to framework residues within VH and/or VL, e.g. to improve the properties of the antibody. In some embodiments such framework modifications are made to decrease immunogenicity of the antibody. For example, one approach is to change one or more framework residues to the corresponding germline sequence. More specifically, an antibody that has undergone somatic mutation may contain framework residues that differ from germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis. Additional framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043 by Can et al.

Constant regions of the antibodies or antibody fragments utilized for preparation of the antibody cytokine engrafted protein can be any type or subtype, as appropriate, and can be selected to be from the species of the subject to be treated by the present methods (e.g., human, non-human primate or other mammal, for example, agricultural mammal (e.g., equine, ovine, bovine, porcine, camelid), domestic mammal (e.g., canine, feline) or rodent (e.g., rat, mouse, hamster, rabbit). In some embodiments antibodies utilized in antibody cytokine engrafted proteins are engineered to generate humanized or HUMANEERED® antibodies. In some embodiments antibodies utilized in antibody cytokine engrafted proteins are human antibodies. In some embodiments, antibody constant region isotype is IgG, for example, IgG1, IgG2, IgG3, IgG4. In certain embodiments the constant region isotype is IgG1. In some embodiments, antibody cytokine engrafted proteins comprise an IgG. In some embodiments, antibody cytokine engrafted proteins comprise an IgG1 Fe. In some embodiments, antibody cytokine engrafted proteins comprise an IgG2 Fe.

In addition or alternative to modifications made within framework or CDR regions, antibodies or antibody fragments utilized in preparation of antibody cytokine engrafted proteins may be engineered to include modifications within an Fe region, typically to alter one or more functional properties of the antibody, such as, e.g., serum half-life, complement fixation, Fe receptor binding, and/or antigen-dependent cellular cytotoxicity. Furthermore, an antibody, antibody fragment thereof, or antibody cytokine engrafted protein can be chemically modified (e.g., one or more chemical moieties can be attached to the antibody) or be modified to alter its glycosylation, again to alter one or more functional properties of the antibody cytokine engrafted protein.

In one embodiment, a hinge region of CHI is modified such that the number of cysteine residues in the hinge region is altered, e.g., increased or decreased. For example, by the approach is described further in U.S. Pat. No. 5,677,425 by Bodmer et al. wherein the number of cysteine residues in the hinge region of CHI is altered to, for example, facilitate assembly of the light and heavy chains or to increase or decrease the stability of the antibody cytokine engrafted protein. In another embodiment, an Fe hinge region of an antibody is mutated to alter the biological half-life of the antibody cytokine engrafted protein. More specifically, one or more amino acid mutations are introduced into the CH2-CH3 domain interface region of the Fe-hinge fragment such that the antibody cytokine engrafted protein has impaired Staphylococcal protein A (SpA) binding relative to native Fe-hinge domain SpA binding. This approach is described in further detail in U.S. Pat. No. 6,165,745 by Ward et al.

The present disclosure provides for antibody cytokine engrafted proteins that specifically bind to the IL2 low affinity receptor which have an extended half-life in vivo. In another embodiment, an antibody cytokine engrafted protein is modified to increase its biological half-life. Various approaches are possible. Antibody cytokine engrafted proteins having an increased half-life in vivo can also be generated introducing one or more amino acid modifications (i.e., substitutions, insertions or deletions) into an IgG constant domain, or FcRn binding fragment thereof (preferably a Fe or hinge Fe domain fragment). For example, one or more of the following mutations can be introduced: T252L, T254S, T256F, as described in U.S. Pat. No. 6,277,375 to Ward. See, e.g., International Publication No. WO 98/23289; International Publication No. WO 97/34631; and U.S. Pat. No. 6,277,375. Alternatively, to increase the biological half-life, the antibody cytokine engrafted protein is altered within the CHI or CL region to contain a salvage receptor binding epitope taken from two loops of a CH2 domain of an Fe region of an IgG, as described in U.S. Pat. Nos. 5,869,046 and 6,121,022 by Presta et al. In yet other embodiments, the Fe region is altered by replacing at least one amino acid residue with a different amino acid residue to alter the effector functions of the antibody cytokine engrafted protein. For example, one or more amino acids can be replaced with a different amino acid residue such that the antibody cytokine engrafted protein has an altered affinity for an effector ligand but retains antigen-binding ability of the parent antibody. The effector ligand to which affinity is altered can be, for example, an Fe receptor (FcR) or the Cl component of complement. This approach is described in further detail in U.S. Pat. Nos. 5,624,821 and 5,648,260, both by Winter et al.

In another embodiment, one or more amino acids selected from amino acid residues can be replaced with a different amino acid residue such that the antibody cytokine engrafted protein has altered C1q binding and/or reduced or abolished complement dependent cytotoxicity (CDC). This approach is described in further detail in U.S. Pat. No. 6,194,551 by Idusogie et al.

Antibody cytokine engrafted proteins containing such mutations mediate reduced or no antibody-dependent cellular cytotoxicity (ADCC) or complement-dependent cytotoxicity (CDC). In some embodiments, amino acid residues L234 and L235 of the IgG1 constant region are substituted to Ala234 and Ala235. In some embodiments, amino acid residue N267 of the IgG1 constant region is substituted to Ala267.

In another embodiment, one or more amino acid residues are altered to thereby alter the ability of the antibody cytokine engrafted protein to fix complement. This approach is described further in PCT Publication WO 94/29351 by Bodmer et al.

In yet another embodiment, an Fe region is modified to increase the ability of the antibody to mediate antibody dependent cellular cytotoxicity (ADCC) and/or to increase the affinity of the antibody cytokine engrafted protein for an Fcy receptor by modifying one or more amino acids. This approach is described further in PCT Publication WO 00/42072 by Presta. Moreover, binding sites on human IgG1 for FcyR1, FcyRII, FcyRIII and FcRn have been mapped and variants with improved binding have been described (see Shields, R. L. et al, 2001 J. Biol. Chen. 276:6591-6604).

In still another embodiment, glycosylation of an antibody cytokine engrafted protein is modified. For example, an aglycosylated antibody cytokine engrafted protein can be made (i.e., the antibody cytokine engrafted protein lacks glycosylation). Glycosylation can be altered to, for example, increase the affinity of the antibody for "antigen." Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation can increase the affinity of the antibody for antigen. Such an approach is described in further detail in U.S. Pat. Nos. 5,714,350 and 6,350,861 by Co et al.

Additionally or alternatively, an antibody cytokine engrafted protein can be made that has an altered type of glycosylation, such as a hypofucosylated antibody cytokine engrafted protein having reduced amounts of fucosyl residues or an antibody having increased bisecting GlcNac structures. Such altered glycosylation patterns have been demonstrated to increase the antibody dependent cellular cytotoxicity (ADCC) ability of antibodies. Such carbohydrate modifications can be accomplished by, for example, expressing the antibody cytokine engrafted protein in a host cell with altered glycosylation machinery. Cells with altered glycosylation machinery have been described in the art and can be used as host cells in which to express recombinant antibody cytokine engrafted proteins to thereby produce an antibody cytokine engrafted protein with altered glycosylation. For example, EP 1,176,195 by Hang et al. describes a cell line with a functionally disrupted FUT8 gene, which encodes a fucosyl transferase, such that antibody cytokine engrafted proteins expressed in such a cell line exhibit hypofucosylation. PCT Publication WO 03/035835 by Presta describes a variant CHO cell line, Lec13 cells, with reduced ability to attach fucose to Asn(297)-linked carbohydrates, also resulting in hypofucosylation of antibody cytokine engrafted proteins expressed in that host cell (see also Shields, R. L. et al., 2002 J. Biol. Chem. 277:26733-26740). PCT Publication WO 99/54342 by Umana et al. describes cell lines engineered to express glycoprotein-modifying glycosyl transferases (e.g., beta (1,4)-N acetyl-glucosaminyltransferase III (GnTIII)) such that antibody cytokine engrafted proteins expressed in the engineered cell lines exhibit increased bisecting GlcNac structures which results in increased ADCC activity of the antibodies (see also Umana et al., 1999 Nat. Biotech. 17:176-180).

In some embodiments, one or more domains, or regions, of an antibody cytokine engrafted protein are connected via a linker, for example, a peptide linker, such as those that are well known in the art (see e.g., Holliger, P., et al. (1993) Proc. Natl. Acad. Sci. USA 90:6444-6448; Poljak, R J., et al. (1994) Structure 2:1121-1123). A peptide linker may vary in length, e.g., a linker can be 1-100 amino acids in length, typically a linker is from five to 50 amino acids in length, e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length.

In some embodiments IL2 is engrafted into the CDR sequence optionally with one or more peptide linker sequences. In certain embodiments one or more peptide linkers is independently selected from a (Glyu-Ser)m sequence (SEQ ID NO: 71), a (Glyu-Ala)m sequence (SEQ ID NO: 72), or any combination of a (Glyn-Ser)m/(Glyn-Ala)m sequence (SEQ ID NOS: 71-72), wherein each n is independently an integer from 1 to 5 and each mis independently an integer from Oto 10. Examples of linkers include, but are not limited to, glycine-based linkers or gly/ser linkers G/S such as (GmS)n wherein n is a positive integer equal to 1, 2, 3, 4, 5, 6, 7, 8, 9, or 10 and mis an integer equal to 0, 1, 2, 3, 4, 5, 6, 7, 8, 9, or 10 (SEQ ID NO: 73). In certain embodiments one or more linkers include G4S (SEQ ID NO: 74) repeats, e.g., the Gly-Ser linker (G4S)n wherein n is a positive integer equal to or greater than 1 (SEQ ID NO: 74). For example, n=1, n=2, n=3. n=4, n=5 and n=6, n=7, n=8, n=9 and n=10. In some embodiments, Ser can be replaced with Ala e.g., linkers G/A such as (GmA)n wherein n is a positive integer equal to 1, 2, 3, 4, 5, 6, 7, 8, 9, or 10 and mis an integer equal to 0, 1, 2, 3, 4, 5, 6, 7, 8, 9, or 10 (SEQ ID NO: 75). In certain embodiments one or more linkers include G4A (SEQ ID NO: 76) repeats, (G4A)n wherein n is a positive integer equal to or greater than 1 (SEQ ID NO: 76). For example, n=1, n=2, n=3. n=4, n=5 and n=6, n=7, n=8, n=9 and n=10. In some embodiments, the linker includes multiple repeats of linkers. In other embodiments, a linker includes combinations and multiples of G4S (SEQ ID NO: 74) and G4A (SEQ ID NO: 76).

Other examples of linkers include those based on flexible linker sequences that occur naturally in antibodies to minimize immunogenicity arising from linkers and junctions. For example, there is a natural flexible linkage between the variable domain and a CHI constant domain in antibody molecular structure. This natural linkage comprises approximately 10-12 amino acid residues, contributed by 4-6 residues from C-terminus of V domain and 4-6 residues from the N-terminus of the CHI domain. Antibody cytokine engrafted proteins can, e.g., employ linkers incorporating terminal 5-6 amino acid residues, or 11-12 amino acid residues, of CHI as a linker. The N-terminal residues of the CHI domain, particularly the first 5-6 amino acid residues, adopt a loop conformation without strong secondary structure, and, therefore, can act as a flexible linker. The N-terminal residues of the CHI domain are a natural extension of the variable domains, as they are part of the lg sequences, and, therefore, minimize to a large extent any immunogenicity potentially arising from the linkers and junctions. In some embodiments a linker sequence includes a modified peptide sequence based on a hinge sequence.

Moreover, the antibody cytokine engrafted proteins can include marker sequences, such as a peptide to facilitate purification of antibody cytokine engrafted proteins. In preferred embodiments, a marker amino acid sequence is a hexa-histidine peptide (SEQ ID NO: 78), such as the tag provided in a pQE vector (QIAGEN, Inc., 9259 Eton Avenue, Chatsworth, CA, 91311), among others, many of which are commercially available. As described in Gentz et al., 1989, Proc. Natl. Acad. Sci. USA 86:821-824, for instance, hexa-histidine (SEQ ID NO: 78) provides for convenient purification of the engrafted protein. Other peptide tags useful for purification include, but are not limited to, the hemagglutinin ("HA") tag, which corresponds to an epitope derived from the influenza hemagglutinin protein (Wilson et al., 1984, Cell 37:767), and the "flag" tag.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Assays for Antibody Cytokine Engrafted Protein Activity

Assays for identifying antibody cytokine engrafted proteins are known in the art and described herein. Agonist antibody cytokine engrafted proteins bind to the IL2 low affinity receptor and promote, induce, stimulate intracellular signaling resulting in CD8+T effector cell proliferation as well as other immunostimulatory effects.

Binding of the antibody cytokine engrafted proteins to the IL2 low affinity receptor can be determined using any method known in the art. For example, binding to the IL2 low affinity receptor can be determined using known techniques, including without limitation ELISA, Western blots, surface plasmon resonance (SPR) (e.g., BIAcore), and flow cytometry.

Intracellular signaling through the IL2 low affinity receptor can be measured using any method known in the art. For example, activation of the IL2 low affinity receptor by IL2 promotes STAT5 activation and signaling. Methods for measuring STAT5 activation are standard in the art (e.g., phosphorylation status of STAT5 protein, reporter gene assays, downstream signaling assays, etc.). Activation through the IL2 low affinity receptor expands CD8+T effector cells, so the absolute numbers of CD8+T effector cells can be assayed for or the ratio of CD8+T effector cells to Tregs can be assayed for. Methods for measuring proliferation of cells are standard in the art (e.g., $^3$H-thymidine incorporation assays, CFSE labelling). Methods for measuring cytokine production are well known in the art (e.g., ELISA assays, ELISpot assays). In performing in vitro assays, test cells or culture supernatant from test cells contacted with antibody cytokine engrafted proteins can be compared to control cells or culture supernatants from control cells that have not been contacted with an antibody cytokine engrafted protein and/or those that have been contacted with recombinant human IL2 (e.g. PROLEUKIN®) or an IL2-Fc fusion molecule.

The activity of the antibody cytokine engrafted proteins can also be measured ex vivo and/or in vivo. In some aspects, methods for measuring STAT5 activation across various cell types ex vivo from animals treated with antibody cytokine engrafted proteins as compared to untreated control animals and/or animals similarly treated with PROLEUKIN® may be used to show differential activity of the agonist antibody engrafted proteins across cell types. Preferred agonist antibody cytokine engrafted proteins have the ability to activate and expand CD8+T effector cells. For example, in vivo activation and expansion of CD S T effector cells can be measured using any method known in the art, e.g., by flow cytometry. Preferred agonist antibody cytokine engrafted proteins can be therapeutically useful in preventing, reducing, alleviating or the treatment of cancer, for example: melanoma, lung cancer, colorectal cancer, prostate cancer, breast cancer and lymphoma. The efficacy of the antibody cytokine engrafted proteins can be determined by administering a therapeutically effective amount of the antibody cytokine engrafted protein to a subject and comparing the subject before and after administration of the antibody cytokine engrafted protein. Efficacy of the antibody cytokine engrafted proteins can also be determined by administering a therapeutically effective amount of an antibody cytokine engrafted protein to a test subject and comparing the test subject to a control subject who has not been administered the antibody and/or comparison to a subject similarly treated with PROLEUKIN®.

Polynucleotides Encoding Antibody Cytokine Engrafted Proteins

In another aspect, isolated nucleic acids encoding heavy and light chain proteins of the antibody cytokine engrafted proteins are provided. Antibody cytokine engrafted proteins can be produced by any means known in the art, including but not limited to, recombinant expression, chemical synthesis, and enzymatic digestion of antibody tetramers. Recombinant expression can be from any appropriate host cells known in the art, for example, mammalian host cells, bacterial host cells, yeast host cells, insect host cells, etc.

Provided herein are polynucleotides that encode the variable regions exemplified in any one of SEQ ID NO:20, SEQ ID NO:36, SEQ ID NO:52 and SEQ ID NO:68.

The disclosure thus provides polynucleotides encoding the light and/or heavy chain polypeptides of the antibody cytokine engrafted proteins described herein, e.g., polynucleotides encoding light or heavy chain variable regions or segments comprising the complementary determining regions as described herein. In some embodiments, the polynucleotide encoding the heavy chain variable regions comprises a sequence having at least 85%, 89%, 90%, 91%, 92%, 93%, 94%, 95%, 96%, 97%, 98%, 99%, or 100% nucleic acid sequence identity with a polynucleotide selected from the group consisting of SEQ ID NO:20, and SEQ ID NO:52. In some embodiments, the polynucleotide encoding the light chain variable regions comprises a sequence having at least 85%, 89%, 90%, 91%, 92%, 93%, 94%, 95%, 96%, 97%, 98%, 99%, or 100% nucleic acid sequence identity with a polynucleotide selected from the group consisting of SEQ ID NO:36, and SEQ ID NO:68.

In some embodiments, the polynucleotide encoding the heavy chain has at least 85%, 89%, 90%, 91%, 92%, 93%, 94%, 95%, 96%, 97%, 98%, 99%, or 100% nucleic acid sequence identity with a polynucleotide of SEQ ID NO:22. In some embodiments, the polynucleotide encoding the light chain has at least 85%, 89%, 90%, 91%, 92%, 93%, 94%, 95%, 96%, 97%, 98%, 99%, or 100% nucleic acid sequence identity with a polynucleotide of SEQ ID NO:38.

In some embodiments, the polynucleotide encoding the heavy chain has at least 85%, 89%, 90%, 91%, 92%, 93%, 94%, 95%, 96%, 97%, 98%, 99%, or 100% nucleic acid sequence identity with a polynucleotide of SEQ ID NO:54. In some embodiments, the polynucleotide encoding the light chain has at least 85%, 89%, 90%, 91%, 92%, 93%, 94%, 95%, 96%, 97%, 98%, 99%, or 100% nucleic acid sequence identity with a polynucleotide selected of SEQ ID NO:70.

Polynucleotides can encode only the variable region sequence of an antibody cytokine engrafted protein. They can also encode both a variable region and a constant region of the antibody cytokine engrafted protein. Some of the polynucleotide sequences encode a polypeptide that comprises variable regions of both the heavy chain and the light chain of one of the antibody cytokine engrafted proteins. Some other polynucleotides encode two polypeptide segments that respectively are substantially identical to the variable regions of the heavy chain and the light chain of one of the antibody cytokine engrafted proteins.

In certain embodiments polynucleotides or nucleic acids comprise DNA. In other embodiments polynucleotides or nucleic acids comprise RNA, which may be single stranded or double stranded.

In some embodiments a recombinant host cell comprising the nucleic acids encoding one or more immunoglobulin protein chain of an antibody cytokine engrafted protein, and optionally, secretion signals is provided. In certain embodiments a recombinant host cell comprises a vector encoding one immunoglobulin protein chain and secretion signals. In other certain embodiments a recombinant host cell comprises one or more vectors encoding two immunoglobulin protein chains of the antibody cytokine engrafted protein and secretion signals. In some embodiments a recombinant host cell comprises a single vector encoding two immunoglobulin protein chains of the antibody cytokine engrafted protein and secretion signals. In some embodiments a recombinant host cell comprises two vectors, one encoding a heavy chain immunoglobulin protein chain, and another encoding a light chain immunoglobulin protein chain of the antibody cytokine engrafted protein, with each including secretion signals. A recombinant host cell may be a prokaryotic or eukaryotic cell. In some embodiments the host cell is a eukaryotic cell line. In some embodiments, the host cell is a mammalian cell line. In some embodiments, the host cell line is a CHO cell line for antibody production.

Additionally provided are methods for producing the antibody cytokine engrafted proteins. In some embodiments the method comprises the steps of (i) culturing a host cell comprising one or more vectors encoding immunoglobulin protein chains of an antibody cytokine engrafted protein under conditions suitable for expression, formation, and secretion of the antibody cytokine engrafted protein and (ii) recovering the antibody cytokine engrafted protein.

The polynucleotide sequences can be produced by de novo solid-phase DNA synthesis or by PCR mutagenesis of an existing sequence (e.g., sequences as described herein) encoding a polypeptide chain of an antibody cytokine engrafted protein. Direct chemical synthesis of nucleic acids can be accomplished by methods known in the art, such as the phosphotriester method of Narang et al., Meth. Enzymol. 68:90, 1979; the phosphodiester method of Brown et al., Meth. Enzymol. 68:109, 1979; the diethylphosphoramidite method of Beaucage et al., Tetra. Lett., 22:1859, 1981; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, NY, 1992; PCR Protocols: A Guide to Methods and Applications, Innis et al. (Ed.), Academic Press, San Diego, C A, 1990; Mattila et al., Nucleic Acids Res. 19:967, 1991; and Eckert et al., PCR Methods and Applications 1:17, 1991.

Also provided in the disclosure are expression vectors and host cells for producing the antibody cytokine engrafted proteins described above. Various expression vectors can be employed to express polynucleotides encoding the immunoglobulin polypeptide chains, or fragments, of the antibody cytokine engrafted proteins. Both viral-based and nonviral expression vectors can be used to produce the immunoglobulin proteins in a mammalian host cell. Nonviral vectors and systems include plasmids, episomal vectors, typically with an expression cassette for expressing a protein or RNA, and human artificial chromosomes (see, e.g., Harrington et al., Nat. Genet. 15:345, 1997). For example, nonviral vectors useful for expression of the antibody cytokine engrafted protein polynucleotides and polypeptides in mammalian (e.g., human) cells include pThioHis A, B & C, pcDNA3.1/His, pEBVHis A, B & C (Invitrogen, San Diego, CA), MPSV vectors, and numerous other vectors known in the art for expressing other proteins. Useful viral vectors include vectors based on retroviruses, adenoviruses, adeno-associated viruses, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68:143, 1992.

The choice of expression vector depends on the intended host cells in which the vector is to be expressed. Typically, the expression vectors contain a promoter and other regulatory sequences (e.g., enhancers) that are operably linked to the polynucleotides encoding an immunoglobulin protein of the antibody cytokine engrafted protein. In some embodiments, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under noninducing conditions without biasing the population for coding sequences whose expression products are better tolerated by the host cells. In addition to promoters, other regulatory elements may also be required or desired for efficient expression of an immunoglobulin chain or fragment of the antibody cytokine engrafted proteins. These elements typically include an ATG initiation codon and adjacent ribosome binding site or other sequences. In addition, the efficiency of expression may be enhanced by the inclusion of enhancers appropriate to the cell system in use (see, e.g., Scharf et al., Results Probl. Cell Differ. 20:125, 1994; and Bittner et al., Meth. Enzymol., 153:516, 1987). For example, the SV40 enhancer or CMV enhancer may be used to increase expression in mammalian host cells.

Expression vectors can also provide a secretion signal sequence position to form an antibody cytokine engrafted protein that exported out of the cell and into the culture medium. In certain aspects, the inserted immunoglobulin sequences of the antibody cytokine engrafted proteins are linked to a signal sequences before inclusion in the vector. Vectors to be used to receive sequences encoding immunoglobulin light and heavy chain variable domains sometimes also encode constant regions or parts thereof. Such vectors allow expression of the variable regions as engrafted proteins with the constant regions thereby leading to production of intact antibody cytokine engrafted proteins or fragments thereof. Typically, such constant regions are human.

Host cells for harboring and expressing the antibody cytokine engrafted protein chains can be either prokaryotic or eukaryotic. *E. coli* is one prokaryotic host useful for cloning and expressing the polynucleotides of the present disclosure. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express antibody cytokine engrafted protein polypeptides. Insect cells in combination with baculovirus vectors can also be used.

In some preferred embodiments, mammalian host cells are used to express and produce the antibody cytokine engrafted protein polypeptides. For example, they can be either a mammalian cell line containing an exogenous expression vector. These include any normal mortal or normal or abnormal immortal animal or human cell. For example, a number of suitable host cell lines capable of secreting intact immunoglobulins have been developed, including the CHO cell lines, various Cos cell lines, HeLa cells, myeloma cell lines, transformed B-cells and hybridomas. The use of mammalian tissue cell culture to express polypeptides is discussed generally in, e.g., Winnacker, From Genes to Clones, VCH Publishers, N.Y., N.Y., 1987. Expression vectors for mammalian host cells can include expression control sequences, such as an origin of replication, a promoter, and an enhancer (see, e.g., Queen et al., Immunol. Rev. 89:49-68, 1986), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP pollll promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts (see generally Sambrook et al., supra). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, engrafted to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express antibody cytokine engrafted protein immunoglobulin chains can be prepared using expression vectors which contain viral origins of replication or endogenous expression elements and a selectable marker gene. Following introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type.

Compositions Comprising Antibody Cytokine Engrafted Proteins

Provided are pharmaceutical compositions comprising an antibody cytokine engrafted protein formulated together with a pharmaceutically acceptable carrier. Optionally, pharmaceutical compositions additionally contain other therapeutic agents that are suitable for treating or preventing a given disorder. Pharmaceutically acceptable carriers enhance or stabilize the composition, or facilitate preparation of the composition. Pharmaceutically acceptable carriers include solvents, dispersion media, coatings, antibacterial and antifungal agents, isotonic and absorption delaying agents, and the like that are physiologically compatible.

A pharmaceutical composition of the present disclosure can be administered by a variety of methods known in the art. Route and/or mode of administration vary depending upon the desired results. It is preferred that administration be by parenteral administration (e.g., selected from any of intravenous, intramuscular, intraperitoneal, intrathecal, intraarterial, or subcutaneous), or administered proximal to the site of the target. A pharmaceutically acceptable carrier is suitable for administration by any one or more of intravenous, intramuscular, intraperitoneal, intrathecal, intraarterial, subcutaneous, intranasal, inhalational, spinal or epidermal administration (e.g., by injection). Depending on the route of administration, active compound, e.g., antibody cytokine engrafted protein, may be coated in a material to protect the compound from the action of acids and other natural conditions that may inactivate the compound. In some embodiments the pharmaceutical composition is formulated for intravenous administration. In some embodiments the pharmaceutical composition is formulation for subcutaneous administration.

An antibody cytokine engrafted protein, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

In some embodiments, a pharmaceutical composition is sterile and fluid. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin. In certain embodiments compositions can be prepared for storage in a lyophilized form using appropriate excipients (e.g., sucrose).

Pharmaceutical compositions can be prepared in accordance with methods well known and routinely practiced in the art. Pharmaceutically acceptable carriers are determined in part by the particular composition being administered, as well as by the particular method used to administer the composition. Accordingly, there is a wide variety of suitable formulations of pharmaceutical compositions. Applicable methods for formulating an antibody cytokine engrafted protein and determining appropriate dosing and scheduling can be found, for example, in *Remington: The Science and Practice of Pharmacy,* 21$^{r1}$ Ed., University of the Sciences in Philadelphia, Eds., Lippincott Williams & Wilkins (2005); and in *Martindale: The Complete Drug Reference,* Sweetman, 2005, London: Pharmaceutical Press., and in Martindale, *Martindale: The Extra Pharmacopoeia,* 31st Edition., 1996, Amer Pharmaceutical Assn, and Sustained and Controlled Release Drug Delivery Systems, J. R. Robinson, ed., Marcel Dekker, Inc., New York, 1978. Pharmaceutical compositions are preferably manufactured under GMP conditions. Typically, a therapeutically effective dose or efficacious dose of an antibody cytokine engrafted protein is employed in the pharmaceutical compositions. An antibody cytokine engrafted protein is formulated into pharmaceutically acceptable dosage form by conventional methods known to those of skill in the art. Dosage regimens are adjusted to provide the desired response (e.g., a therapeutic response). In determining a therapeutically or prophylactically effective dose, a low dose can be administered and then incrementally increased until a desired response is achieved with minimal or no undesired side effects. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Actual dosage levels of active ingredients in the pharmaceutical compositions can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors.

Articles of Manufacture/Kits

In some aspects an antibody cytokine engrafted protein is provided in an article of manufacture (i.e., a kit). A provided antibody cytokine engrafted protein is generally in a vial or a container. Thus, an article of manufacture comprises a container and a label or package insert, on or associated with the container. Suitable containers include, for example, a bottle, vial, syringe, solution bag, etc. As appropriate, the antibody cytokine engrafted protein can be in liquid or dried (e.g., lyophilized) form. The container holds a composition which, by itself or combined with another composition, is effective for preparing a composition for treating, preventing and/or ameliorating cancer. The label or package insert indicates the composition is used for treating, preventing and/or ameliorating cancer. Articles of manufacture (kits) comprising an antibody cytokine engrafted protein, as described herein, optionally contain one or more additional agent. In some embodiments, an article of manufacture (kit) contains antibody cytokine engrafted protein and a pharmaceutically acceptable diluent. In some embodiments an antibody cytokine engrafted protein is provided in an article of manufacture (kit) with one or more additional active agent in the same formulation (e.g., as mixtures). In some embodiments an antibody cytokine engrafted protein is provided in an article of manufacture (kit) with a second or third agent in separate formulations (e.g., in separate containers). In certain embodiments an article of manufacture (kit) contains aliquots of the antibody cytokine engrafted protein wherein the aliquot provides for one or more doses. In some embodiments aliquots for multiple administrations are provided, wherein doses are uniform or varied. In particular embodiments varied dosing regimens are escalating or decreasing, as appropriate. In some embodiments dosages of an antibody cytokine engrafted protein and a second agent are independently uniform or independently varying. In certain embodiments, an article of manufacture (kit) comprises an additional agent such as an anti-cancer agent or immune checkpoint molecule. Selection of one or more additional agent will depend on the dosage, delivery, and disease condition to be treated.

Methods of Treatment and Use of Compositions for Treatment of Cancer

Conditions Subject to Treatment or Prevention

Antibody cytokine engrafted proteins find use in treatment, amelioration or prophylaxis of cancer. In one aspect, the disclosure provides methods of treatment of cancer in an individual in need thereof, comprising administering to the individual a therapeutically effective amount of an antibody cytokine engrafted protein, as described herein. In some embodiment an antibody cytokine engrafted protein is provided for use as a therapeutic agent in the treatment or prophylaxis of cancer in an individual. In a further aspect, the disclosure provides a composition comprising such an antibody cytokine engrafted protein for use in treating or ameliorating cancer in an individual in need thereof.

Conditions subject to treatment include various cancer indications. For therapeutic purposes, an individual was diagnosed with cancer. For preventative or prophylactic purposes, an individual may be in remission from cancer or may anticipate future onset. In some embodiments, the patient has cancer, is suspected of having cancer, or is in remission from cancer. Cancers subject to treatment with an antibody cytokine engrafted protein usually derive benefit from activation of IL2 low affinity receptor signaling, as described herein. Cancer indications subject to treatment include without limitation: melanoma, lung cancer, colorectal cancer, prostate cancer, breast cancer and lymphoma Administration of Antibody Cytokine Engrafted Proteins A physician or veterinarian can start doses of an antibody cytokine engrafted protein employed in the pharmaceutical composition at levels lower than that required to achieve the desired therapeutic effect and gradually increase the dosage until the desired effect is achieved. In general, effective doses of the compositions vary depending upon many different factors, including the specific disease or condition to be treated, means of administration, target site, physiological state of the patient, whether a patient is human or an animal, other medications administered, and whether treatment is prophylactic or therapeutic. Treatment dosages typically require titration to optimize safety and efficacy. For administration with an antibody cytokine engrafted protein, dosage ranges from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. Dosing can be daily, weekly, bi-weekly, monthly, or more or less often, as needed or desired. An exemplary treatment regime entails administration once weekly, once per every two weeks or once a month or once every 3 to 6 months.

The antibody cytokine engrafted protein can be administered in single or divided doses. An antibody cytokine engrafted protein is usually administered on multiple occasions. Intervals between single dosages can be weekly, bi-weekly, monthly or yearly, as needed or desired. Intervals can also be irregular as indicated by measuring blood levels of antibody cytokine engrafted protein in the patient. In some methods, dosage is adjusted to achieve a plasma antibody cytokine engrafted protein concentration of 1-1000 µg/ml and in some methods 25-300 µg/ml. Alternatively, antibody cytokine engrafted protein can be administered as a sustained release formulation, in which case less frequent administration is required. Dosage and frequency vary depending on the half-life of the antibody cytokine engrafted protein in the patient. In general, antibody engrafted proteins show longer half-life than that of native IL2 or recombinant cytokines such as PROLEUKIN®. Dosage and frequency of administration can vary depending on whether treatment is prophylactic or therapeutic. In general for prophylactic applications, a relatively low dosage is administered at relatively infrequent intervals over a long period of time. Some patients continue to receive treatment for the duration of their lives. In general for therapeutic applications, a relatively high dosage in relatively short intervals is sometimes required until progression of the disease is reduced or terminated, and preferably until the patient shows partial or complete amelioration of symptoms of disease. Thereafter, a patient may be administered a prophylactic regime.

Co Administration with a Second Agent

The term "combination therapy" refers to the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients. Alternatively, such administration encompasses co-administration in multiple, or in separate containers (e.g., capsules, powders, and liquids) for each active ingredient. Powders and/or liquids may be reconstituted or diluted to a desired dose prior to administration. In addition, such administration also encompasses use of each type of therapeutic agent in a sequential manner, either at approximately the same time or at different times. In either case, the treatment regimen will provide beneficial effects of the drug combination in treating the conditions or disorders described herein.

The combination therapy can provide "synergy" and prove "synergistic", i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

In one aspect, the present disclosure provides a method of treating cancer by administering to a subject in need thereof an antibody cytokine engrafted protein in combination with one or more tyrosine kinase inhibitors, including but not limited to, EGFR inhibitors, Her2 inhibitors, Her3 inhibitors, IGFR inhibitors, and Met inhibitors.

For example, tyrosine kinase inhibitors include but are not limited to, Erlotinib hydrochloride (TARCEVA®); Linifanib (N-[4-(3-amino-IH-indazol-4-yl)phenyl]-N'-(2-fluoro-5-methylphenyl)urea, also known as ABT 869, available from Genentech); Sunitinib malate (SUTENT®); Bosutinib (4-[(2,4-dichloro-5-methoxyphenyl)amino]-6-methoxy-7-[3-(4-methylpiperazin-1-yl)propoxylquinoline-3-carbonitrile, also known as SKI-606, and described in U.S. Pat. No. 6,780,996); Dasatinib(SPRYCEL®; Pazopanib (VOTRIENT®); Sorafenib (NEXAVAR®); Zactima (ZD6474); nilotinib (TASIGNA®); Regorafenib (STIVARGA®) and Imatinib or Imatinib mesylate (GILVEC® and GLEEVEC®).

Epidermal growth factor receptor (EGFR) inhibitors include but are not limited to, Erlotinib hydrochloride (TARCEVA® STIVARGA®), Gefitnib (LRESSA®); N-[4-[(3-Chloro-4-fluorophenyl)amino]-7-[[(3"S")-tetrahydro-3-furanyl]oxy]-6-quinazolinyl]-4(dimethylamino)-2-butenamide, TOVOK®); Vandetanib (CAPRELSA®); Lapatinib (TYKERB®); (3R,4R)-4-Amino-1-((4-((3-methoxyphenyl)amino)pyrrolo[2,1-f][1,2,4]triazin-5-yl) methyl)piperidin-3-ol (BMS690514); Canertinib dihydrochloride (CI-1033); 6-[4-[(4-Ethyl-1-piperazinyl)methyl] phenyl]-N-[(IR)-1-phenylethyl]-7H-Pyrrolo[2,3-d] pyrimidin-4-amine (AEE788, CAS 497839-62-0); Mubritinib (TAK165); Pelitinib (EKB569); Afatinib (BIBW2992); Neratinib (HKI-272); N-[4-[[1-[(3-Fluorophenyl)methyl]-IH-indazol-5-yl]amino]-5-methylpyrrolo[2, 1-f][1,2,4]triazin-6-yl]-carbamic acid, (3S)-3-morpholinyl-methyl ester (BMS599626); N-(3,4-Dichloro-2-fluorophenyl)-6-methoxy-7-[[(3aa,5,6aa)-octahydro-2-methylcyclopenta[c]pyrrol-5-yl]methoxy]-4-quinazolinamine (XL647, CAS 781613-23-8); and 4-[4-[[(1R)-1-Phenylethyl]amino]-7H-pyrrolo[2,3-d]pyrimidin-6-yl]-phenol (PK1166, CAS 187724-61-4).

EGFR antibodies include but are not limited to, Cetuximab (Erbitux®); Panitumumab (VECTIBIX); Matuzumab (EMD-72000); Nimotuzumab (hR3); Zalutumumab; TheraCIM h-R3; MDX0447 (CAS 339151-96-1); and ch806 (mAb-806, CAS 946414-09-1).

Human Epidermal Growth Factor Receptor 2 (HER2 receptor) (also known as Neu, ErbB-2, CD340, or p185) inhibitors include but are not limited to, Trastuzumab (HERCEPTIN®); Pertuzumab (OMNITARG®); Neratinib (HKI-272, (2E)-N-[4[[3-chloro-4-[(pyridin-2-yl)methoxy]phenyl] amino]-3-cyano-7-ethoxyquinolin-6-yl]-4-(dimethylamino) but-2-enamide, and described PCT Publication No. WO 05/028443); Lapatin ib or Lapatinib ditosylate (TYKERB®); (3R,4R)-4-amino-1-((4-((3-methoxyphenyl)amino) pyrrolo[2, 1-f][1,2,4]triazin-5-yl)methyl)piperidin-3-ol (BMS690514); (2E)-N44-[(3-Chloro-4-fluorophenyl) amino]-7-[[(3S)-tetrahydro-3-furanyl]oxyl-6-quinazolinyl]-4-(dimethylamino)-2-butenamide (BIBW-2992, CAS 850140-72-6); N-[4-[[1-[(3-Fluorophenyl)methyl]-IH-indazol-5-yl]amino]-5-methylpyrrolo[2,1-f][1,2,4]triazin-6-yl]-carbamic acid, (3S)-3-morpholinylmethyl ester (BMS 599626, CAS 714971-09-2); Canertinib dihydrochloride (PD183805 or CI-1033); and N-(3,4-Dichloro-2-fluorophenyl)-6-methoxy-7-[[(3aa,5,6aa)-octahydro-2-methylcyclopenta[c]pyrrol-5-yl]methoxy]-4-quinazolinamine (XL647, CAS 781613-23-8).

HERS inhibitors include but are not limited to, LJM716, MM-121, AMG-888, RG7116, REGN-1400, AV-203, MP-RM-I, MM-111, and MEHD-7945A.

MET inhibitors include but are not limited to, Cabozantinib (XL184, CAS 849217-68-1); Foretinib (GSK1363089, formerly XL880, CAS 849217-64-7); Tivantinib (ARQI 97, CAS 1000873-98-2); 1-(2-Hydroxy-2-methylpropyl)-N-(5-(7-methoxyquinolin-4-yloxy)pyridin-2-yl)-5-methyl-3-oxo-2-phenyl-2,3-dihydro-IH-pyrazole-4-carboxamide (AMG 458); Cryzotinib (XALKORI®, PF-02341066); (3Z)-5-(2, 3-Dihydro-1H-indol-1-ylsulfonyl)-3-({3,5-dimethyl-4-[(4-methylpiperazin-1-yl)carbonyl]-1H-pyrrol-2-yl}methylene)-1,3-dihydro-2H-indol-2-one (SU1 1271); (3Z)-N-(3-Chlorophenyl)-3-({3,5-dimethyl-4-[(4-methylpiperazin-1-yl)carbonyl]-1H-pyrrol-2-yl}methylene)-N-methyl-2-oxoindoline-5-sulfonamide (SU1 1274); (3Z)-N-(3-Chlorophenyl)-3-{[3,5-dimethyl-4-(3-morpholin-4-ylpropyl)-1H-pyrrol-2-yl]methylene}-N-methyl-2-oxoindoline-5-sulfonamide (SU1 1606); 6-[Difluoro[6-(1-methyl-1H-pyrazol-4-yl)-1,2,4-triazolo[4,3-b]pyridazin-3-yl]methyl]-quinoline (JNJ38877605, CAS 943540-75-8);

2-[4-[1-(Quinolin-6-ylmethyl)-1H-[1,2,3]triazolo[4,5-b]pyrazin-6-yl]-1H-pyrazol-1-yl]ethanol (PF04217903, CAS 956905-27-4); N-((2R)-1,4-Dioxan-2-ylmethyl)-N-methyl-N'-[3-(1-methyl-1H-pyrazol-4-yl)-5-oxo-5H-benzo[4,5]cyclohepta[1,2-b]pyridin-7-yl]sulfamide (MK2461, CAS 917879-39-1); 6-[[6-(1-Methyl-1H-pyrazol-4-yl)-1,2,4-triazolo[4,3-b]pyridazin-3-yl]thio]-quinoline (SGX523, CAS 1022150-57-7); and (3Z)-5-[[(2,6-Dichlorophenyl)methyl]sulfonyl]-3-[[3,5-dimethyl-4-[R2R)-2-(1-pyrrolidinylmethyl)-1-pyrrolidinyl]carbonyl]-1H-pyrrol-2-yl]methylene]-1,3-dihydro-2H-indol-2-one (PHA665752, CAS 477575-56-7).

IGF1R inhibitors include but are not limited to, BMS-754807, XL-228, OSI-906, GSK0904529A, A-928605, AXL1717, KW-2450, MK0646, AMG479, IMCA12, MED1-573, and BI836845. See e.g., Yee, JNCI, 104; 975 (2012) for review.

In another aspect, the present disclosure provides a method of treating cancer by administering to a subject in need thereof an antibody cytokine engrafted protein in combination with one or more FGF downstream signaling pathway inhibitors, including but not limited to, MEK inhibitors, Braf inhibitors, PI3K/Akt inhibitors, SHP2 inhibitors, and also mTor inhibitors.

For example, mitogen-activated protein kinase (MEK) inhibitors include but are not limited to, XL-518 (also known as GDC-0973, Cas No. 1029872-29-4, available from ACC Corp.); 2-[(2-Chloro-4-iodophenyl)amino]-N-(cyclopropylmethoxy)-3,4-difluoro-benzamide (also known as CI-1040 or PD184352 and described in PCT Publication No. WO2000035436); N-[(2R)-2,3-Dihydroxypropoxy]-3,4-difluoro-2-[(2-fluoro-4-iodophenyl)amino]-benzamide (also known as PD0325901 and described in PCT Publication No. WO2002006213); 2,3-Bis[amino[(2-aminophenyl)thio]methylene]-butanedinitrile (also known as U0126 and described in U.S. Pat. No. 2,779,780); N-[3,4-Difluoro-2-[(2-fluoro-4-iodophenyl)amino]-6-methoxyphenyl]-1-[(2R)-2,3-dihydroxypropyl]-cyclopropanesulfonamide (also known as RDEA119 or BAY869766 and described in PCT Publication No. WO2007014011); (3S,4R,5Z,8S,9S,11E)-14-(Ethylamino)-8,9,16-trihydroxy-3,4-dimethyl-3,4,9,19-tetrahydro-1H-2-benzoxacyclotetradecine-1,7(8H)-dione] (also known as E6201 and described in PCT Publication No. WO2003076424); 2'-Amino-3'-methoxyflavone (also known as PD98059 available from Biaffin GmbH & Co., KG, Germany); Vemurafenib (PLX-4032, CAS 918504-65-1); (R)-3-(2,3-Dihydroxypropyl)-6-fluoro-5-(2-fluoro-4-iodophenylamino)-8-methylpyrido[2,3-d]pyrimidine-4,7(3H,8H)-dione (TAK-733, CAS 1035555-63-5); Pimasertib (AS-703026, CAS 1204531-26-9); and Trametinib dimethyl sulfoxide (GSK-1120212, CAS 1204531-25-80).

Phosphoinositide 3-kinase (PI3K) inhibitors include but are not limited to, 4-[2-(1H-Indazol-4-yl)-6-[[4-(methylsulfonyl)piperazin-1-yl]methyl]thieno[3,2-d]pyrimidin-4-yl]morpholine (also known as GDC 0941 and described in PCT Publication Nos. WO 09/036082 and WO 09/055730); 2-Methyl-2-[4-[3-methyl-2-oxo-8-(quinolin-3-yl)-2,3-dihydroimidazo[4,5-c]quinolin-1-yl]phenyl]propionitrile (also known as BEZ 235 or NVP-BEZ 235, and described in PCT Publication No. WO 06/122806); 4-(trifluoromethyl)-5-(2,6-dimorpholinopyrimidin-4-yl)pyridin-2-amine (also known as BKM120 or NVP-BKM120, and described in PCT Publication No. WO2007/084786); Tozasertib (VX680 or MK-0457, CAS 639089-54-6); (5Z)-5-[[4-(4-Pyridinyl)-6-quinolinyl]methylene]-2,4-thiazolidinedione (GSK1059615, CAS 958852-01-2); (1E,4S,4aR,5R,6aS,9aR)-5-(Acetyloxy)-1-[(di-2-propenylamino)methylene]-4,4a,5,6,6a,8,9,9a-octahydro-11-hydroxy-4-(methoxymethyl)-4a,6a-dimethyl-cyclopenta[5,6]naphtho[1,2-c]pyran-2,7,10 (1H)-trione (PX866, CAS 502632-66-8); and 8-Phenyl-2-(morpholin-4-yl)-chromen-4-one (LY294002, CAS 154447-36-6).

mTor inhibitors include but are not limited to, Temsirolimus (Torisel®); Ridaforolimus (formally known as deferolimus, (1R,2R,4S)-4-[(2R)-2 [(1R,9S,12S, 15R,16E,18R, 19R,21R, 23S,24E,26E,28Z,30S,32S,35R)-1,18-dihydroxy-19,30-dimethoxy-15, 17, 21, 23, 29, 35-hexamethyl-2, 3, 10, 14, 20-pentaoxo-1 1,36-dioxa-4-azatricyclo[30.3.1.04,9], hexatriaconta-16,24,26,28-tetraen-12-yl]propyl]-2-methoxycyclohexyl dimethylphosphinate, also known as AP23573 and MK8669, and described in PCT Publication No. WO 03/064383); Everolimus (AFINITOR® or RAD001); Rapamycin (AY22989, Sirolimus®); Simapimod (CAS 164301-51-3); (5-12,4-Bis[(3S)-3-methylmorpholin-4-yl]pyrido[2,3-cl]pyrimidin-7-yl]-2-methoxyphenyl)methanol (AZD8055); 2-Amino-8-[trans-4-(2-hydroxyethoxy)cyclohexyl]-6-(6-methoxy-3-pyridinyl)-4-methyl-pyrido[2,3-d]pyrimidin-7(8H)-one (PF04691502, CAS 1013101-36-4); and N2-[1,4-dioxo-4-[[4-(4-oxo-8-phenyl-4H-1-benzopyran-2-yl)morpholinium-4-yl]methoxy]butyl]-L-arginylglycyl-L-a-aspartylL-serine-("L-arginylglycyl-L-a-aspartylL-serine-" disclosed as SEQ ID NO: 77), inner salt (SF1126, CAS 936487-67-1).

In yet another aspect, the present disclosure provides a method of treating cancer by administering to a subject in need thereof an antibody cytokine engrafted protein in combination with one or more pro-apoptotics, including but not limited to, IAP inhibitors, Bcl2 inhibitors, MC11 inhibitors, Trail agents, Chk inhibitors.

For examples, IAP inhibitors include but are not limited to, NVP-LCL161, GDC-0917, AEG-35156, AT406, and TL32711. Other examples of IAP inhibitors include but are not limited to those disclosed in WO04/005284, WO 04/007529, WOOS/097791, WO 05/069894, WO 05/069888, WO 05/094818, US2006/0014700, US2006/0025347, WO 06/069063, WO 06/010118, WO 06/017295, and WO08/134679.

BCL-2 inhibitors include but are not limited to, 4-[4-[[2-(4-Chlorophenyl)-5,5-dimethyl-1-cyclohexen-1-yl]methyl]-1-piperazinyl]-N-[[4-[[(IR)-3-(4-morpholinyl)-1-[(phenylthio)methyl]propyl]amino]-3-[(trifluoromethyl)sulfonyl]phenyl]sulfonyl]benzamide (also known as ABT-263 and described in PCT Publication No. WO 09/155386); Tetrocarcin A; Antimycin; Gossypol ((-)BL-193); Obatoclax; Ethyl-2-amino-6-cyclopentyl-4-(1-cyano-2-ethoxy-2-oxoethyl)-4Hchromone-3-carboxylate (HA14-1); Oblimersen (G3139, GENASENSE®); Bak BH3 peptide; (-)-Gossypol acetic acid (AT-101); 4-[4-[(4'-Chloro[1, 1'-biphenyl]-2-yl)methyl]-1-piperazinyl]-N-[[4-[[(IR)-3-(dimethylamino)-1-[(phenylthio)methyl]propyl]amino]-3-nitrophenyl]sulfonyl]-benzamide (ABT-737, CAS 852808-04-9); and Navitoclax (ABT-263, CAS 923564-51-6).

Proapoptotic receptor agonists (PARAs) including DR4 (TRAILR1) and DRS (TRAILR2), including but are not limited to, Dulanermin (AMG-951, RhApo2L/TRAIL); Mapatumumab (HRS-ETR1, CAS 658052-09-6); Lexatumumab (HGS-ETR2, CAS 845816-02-6); Apomab (Apomab®); Conatumumab (AMG655, CAS 896731-82-1); and Tigatuzumab (CS1008, CAS 946415-34-5, available from Daiichi Sankyo).

Checkpoint Kinase (CHK) inhibitors include but are not limited to, 7-Hydroxystaurosporine (UCN-01); 6-Bromo-3-(1-methyl-1H-pyrazol-4-yl)-5-(3R)-3-piperidinyl-pyrazolo

[1,5-a]pyrimidin-7-amine (SCH900776, CAS 891494-63-6); 5-(3-Fluorophenyl)-3-ureidothiophene-2-carboxylic acid N-[(S)-piperidin-3-yl]amide (AZD7762, CAS 860352-01-8); 4-[((3S)-1-Azabicyclo[2.2.2]oct-3-yl)amino]-3-(1H-benzimidazol-2-yl)-6-chloroquinolin-2(1H)-one (CHIR 124, CAS 405168-58-3); 7-Aminodactinomycin (7-AAD), Isogranulatimide, debromohymenialdisine; N-[5-Bromo-4-methyl-2-[(2S)-2-morpholinylmethoxy]-phenyl]-N'-(5-methyl-2-pyrazinyl)urea (LY2603618, CAS 911222-45-2); Sulforaphane (CAS 4478-93-7, 4-Methylsulfinylbutyl isothiocyanate); 9,10,11,12-Tetrahydro-9,12-epoxy-IH-diindolo[1,2,3-Jg:3',2', 1'-kl]pyrrolo[3,4-i][1,6]benzodiazocine-1,3(2H)-dione (SB-218078, CAS 135897-06-2); and TAT-S216A (Sha et al., Mol. Cancer. Ther 2007; 6(1):147-153), and CBP501.

In one aspect, the present disclosure provides a method of treating cancer by administering to a subject in need thereof an antibody cytokine engrafted protein in combination with one or more FGFR inhibitors. For example, FGFR inhibitors include but are not limited to, Brivanib alaninate (BMS-582664, (S)-((R)-1-(4-(4-Fluoro-2-methyl-1H-indol-5-yloxy)-5-methylpyrrolo[2,1-j][1,2,4]triazin-6-yloxy)propan-2-yl)2-aminopropanoate); Vargatef (BIBFI 120, CAS 928326-83-4); Dovitinib dilactic acid (TKI258, CAS 852433-84-2); 342,6-Dichloro-3,5-dimethoxy-phenyl)-1-{6-[4-(4-ethyl-piperazin-1-yl)-phenylamino]-pyrimidin-4-yl}-1-methyl-urea (BGJ398, CAS 872511-34-7); Danusertib (PHA-739358); and (PD173074, CAS 219580-11-7). In a specific aspect, the present disclosure provides a method of treating cancer by administering to a subject in need thereof an antibody drug conjugate in combination with an FGFR2 inhibitor, such as 3-(2,6-dichloro-3,5-dimethoxyphenyl)-1-(6((4-(4-ethylpiperazin-1-yl)phenyl)amino)pyrimidin-4-yl)-1-methylurea (also known as BGJ-398); or 4-amino-5-fluoro-3-(5-(4-methylpiperazinl-yl)-1H-benzo[d]imidazole-2-yl)quinolin-2(1H)-one (also known as dovitinib or TKI-258).

AZD4547 (Gavine et al., 2012, Cancer Research 72, 2045-56, N-[5-[2-(3,5-Dimethoxyphenyl)ethyl]-2H-pyrazol-3-yl]-4-(3R,5S)-diemthylpiperazin-1-yl)benzamide), Ponatinib (AP24534; Gozgit et al., 2012, Mol Cancer Ther., 11; 690-99; 3-[2-(imidazo[1,2-b]pyridazin-3-yl)ethynyl]-4-methyl-N-{4[(4-methylpiperazin-1-yl)methyl]-3-(trifluoromethyl)phenyl}benzamide, CAS 943319-70-8).

The antibody cytokine engrafted proteins can also be administered in combination with an immune checkpoint inhibitor. In one embodiment, the antibody cytokine engrafted proteins can be administered in combination with an inhibitor of an immune checkpoint molecule chosen from one or more of PD-I, PD-LI, PD-L2, TIM3, CTLA-4, LAG-3, CEACAM-1, CEACAM-5, VISTA, BTLA, TIGIT, LAIRI, CD160, 2B4 or TGFR In one embodiment, the immune checkpoint inhibitor is an anti-PD-I antibody, wherein the anti-PD-I antibody is chosen from Nivolumab, Pembrolizumab or Pidilizumab. In some embodiments, the anti-PD-I antibody molecule is Nivolumab. Alternative names for Nivolumab include MDX-1106, MDX-1106-04, ONO-4538, or BMS-936558. In some embodiments, the anti-PD-1 antibody is Nivolumab (CAS Registry Number: 946414-94-4). Nivolumab is a fully human IgG4 monoclonal antibody which specifically blocks PDI. Nivolumab (clone 5C4) and other human monoclonal antibodies that specifically bind to PDI are disclosed in U.S. Pat. No. 8,008,449 and WO2006/121168.

In some embodiments, the anti-PD-I antibody is Pembrolizumab. Pembrolizumab (also referred to as Lambrolizumab, MK-3475, MK03475, SCH-900475 or KEYTRUDA®; Merck) is a humanized IgG4 monoclonal antibody that binds to PD-I. Pembrolizumab and other humanized anti-PD-I antibodies are disclosed in Hamid, 0. et al. (2013) New England Journal of Medicine 369 (2): 134-44, U.S. Pat. No. 8,354,509 and WO2009/114335.

In some embodiments, the anti-PD-I antibody is Pidilizumab. Pidilizumab (CT-011; Cure Tech) is a humanized IgG1k monoclonal antibody that binds to PDI. Pidilizumab and other humanized anti-PD-I monoclonal antibodies are disclosed in WO2009/101611.

Other anti-PDI antibodies include AMP 514 (Amplimmune) and, e.g., anti-PDI antibodies disclosed in U.S. Pat. No. 8,609,089, US 2010/028330, and/or US 2012/0114649 and US2016/0108123.

In some embodiments, the antibody cytokine engrafted proteins can be administered with the anti-Tim3 antibody disclosed in US2015/0218274. In other embodiments, the antibody cytokine engrafted proteins can be administered with the anti-PD-L1 antibody disclosed in US2016/0108123, DURVALUMAB® (MEDI4736), ATEZOLIZUMAB® (MPDL3280A) or AVELUMAB®.

EXAMPLES

Example 1: Creation of IL2 Antibody Cytokine Engrafted Proteins

Antibody cytokine engrafted proteins were generated by engineering an IL2 sequence into CDR regions of various immunoglobulin scaffolds, then both heavy and light chain immunoglobulin chains were used to generate final antibody cytokine proteins. Antibody cytokine engrafted proteins confer preferred therapeutic properties of IL2; however, antibody cytokine engrafted proteins have reduced undesired effects, such as increased Treg cell activity, as compared with rhIL2.

To create antibody cytokine engrafted proteins, IL2 sequences containing muteins (SEQ ID NO:4 or 6) were inserted into CDR loops of an immunoglobulin chain scaffold. Antibody cytokine engrafted proteins were prepared using a variety of known immunoglobulin sequences which have been utilized in clinical settings as well as germline antibody sequences. Sequences of IL2 in an exemplary scaffold, referred to as GFTX3b, are depicted in TABLE 2. Insertion points were selected to be the mid-point of the loop based on available structural or homology model data. Antibody cytokine engrafted proteins were produced using standard molecular biology methodology utilizing recombinant DNA encoding the relevant sequences.

The selection of which CDR is chosen for cytokine engraftment was chosen on the parameters of: the required biology, biophysical properties and a favorable development profile. Modeling software was only partially useful in predicting which CDR and which location within the CDR will provide the desired parameters, so therefore all six possible antibody cytokine grafts were made and then evaluated in biological assays. If the required biological activity is achieved, then the biophysical properties such as structural resolution as to how the antibody cytokine engrafted molecule interacts with the respective cytokine receptor are resolved.

For the IL2 antibody cytokine engrafted molecules, the structure of the antibody candidate considered for cytokine engrafting was initially solved. From this structure, it was noted that the paratope was at the extreme N-terminus of the antibody "arm" and that a cytokine engrafted into this location would present the cytokine to its respective receptor. Because of the grafting technology, each antibody IL2 engrafted protein is constrained by a CDR loop of different length, sequence and structural environments. As such, IL2 was engrafted into all six CDRs, corresponding to LCDR-1, LCDR-2, LCDR-3 and HCDR-1, HCDR-2 and HCDR-3. From the table in FIG. 1, it is apparent that the antibody cytokine engrafted proteins differ in their activities, including that IL2 engrafted into the light chain of CDR2 (IgG.IL2.L2) did not express. It was also observed that IL2 antibody cytokine grafts with altered Fc function (e.g. Fc silent) had a better profile.

HCDR-1 was chosen because it had the best combination of properties (biophysical and biological) and the IL2 point mutations that were included enhanced the desired biological properties. For the selection of the insertion point, the structural center of the CDR loop was chosen as this would provide the most space on either side (of linear size 3.8A× the number of residues) and without being bound by any one theory, this provided a stable molecule by allowing the IL2 to more readily fold independently. As the structure of the grafting scaffold GFTX3b was already known, so the structural center of each CDR was also known. This coincided with the center of the CDR loop sequence as defined using the Chothia numbering format. As mentioned previously, the insertion point of the IL-2 grafts were shifted away from the center and toward either the Nor C terminal portion of the CDR loop. However, shifting IL2 within the CDR loop did not make a significant difference in biological activity.

In summary, the insertion point in each CDR was chosen on a structural basis, with the hypothesis that grafting into the CDR would provide some level of steric hindrance to individual subunits of the IL2 receptor. The final selection of which CDR graft was best for a particular cytokine was based on desired biology and biophysical properties. The nature of the cytokine receptor, the cytokine/receptor interactions and the mechanism of signaling also played a role and this was done by comparing each individual antibody cytokine molecule for their respective properties.

TABLE 1

| | | |
|---|---|---|
| SEQ ID NO: 1 | IL2 wild type DNA | AGTTCCCTATCACTCTCTTTAATCACTACTCACAGTAA<br>CCTCAACTCCTGCCACAATGTACAGGATGCAACTCCTG<br>TCTTGCATTGCACTAAGTCTTGCACTTGTCACAAACAG<br>TGCACCTACTTCAAGTTCTACAAAGAAAACACAGCTAC<br>AACTGGAGCATTTACTGCTGGATTTACAGATGATTTTG<br>AATGGAATTAATAATTACAAGAATCCCAAACTCACCAG<br>GATGCTCACATTTAAGTTTTACATGCCCAAGAAGGCCA<br>CAGAACTGAAACATCTTCAGTGTCTAGAAGAAGAACTC<br>AAACCTCTGGAGGAAGTGCTAAATTTAGCTCAAAGCAA<br>AAACTTTCACTTAAGACCCAGGGACTTAATCAGCAATA<br>TCAACGTAATAGTTCTGGAACTAAAGGGATCTGAAACA<br>ACATTCATGTGTGAATATGCTGATGAGACAGCAACCAT<br>TGTAGAATTTCTGAACAGATGGATTACCTTTTGTCAAA<br>GCATCATCTCAACACTGACTTGATAATTAAGTGCTTCC<br>CACTTAAAACATATCAGGCCTTCTATTTATTTAAATAT<br>TTAAATTTTATATTTATTGTTGAATGTATGGTTTGCTA<br>CCTATTGTAACTATTATTCTTAATCTTAAAACTATAAA<br>TATGGATCTTTTATGATTCTTTTTGTAAGCCCTAGGGG<br>CTCTAAAATGGTTTCACTTATTTATCCCAAAATATTTA<br>TTATTATGTTGAATGTTAAATATAGTATCTATGTAGAT<br>TGGTTAGTAAAACTATTTAATAAATTTGATAAATATAA<br>AAAAAAAAAAAAAAAAAAAAAAAA |
| SEQ ID NO: 2 | IL2 Protein | MYRMQLLSCIALSLALVTNSAPTSSSTKKTQLQLEHLL<br>LDLQMILNGINNYKNPKLTRMLTFKFYMPKKATELKHL<br>QCLEEELKPLEEVLNLAQSKNFHLRPRDLISNINVIVL<br>ELKGSETTFMCEYADETATIVEFLNRWITFCQSIISTL<br>T |
| SEQ ID NO: 3 | IL2 mutein DNA | CAAGTCACACTGCGTGAAAGCGGCCCTGCCCTGGTCAA<br>GCCCACCCAGACCCTGACCCTGACCTGCACCTTCTCCG<br>GCTTCAGCCTGGCCCCTACCTCCTCCAGCACCAAGAAA<br>ACCCAGCTGCAGCTCGAACATCTGCTGCTGGACCTGCA<br>GATGATCCTGAACGGCATCAACAACTACAAGAACCCCA<br>AGCTGACCCGGATGCTGACCGCCAAGTTCTACATGCCC<br>AAGAAGGCCACCGAGCTGAAACATCTGCAGTGCCTGGA<br>AGAGGAACTGAAGCCCCTGGAAGAAGTGCTGAACCTGG<br>CCCAGTCCAAGAACTTCCACCTGAGGCCTCGGGACCTG<br>ATCTCCAACATCAACGTGATCGTGCTGGAACTGAAGGG<br>CTCCGAGACAACCTTCATGTGCGAGTACGCCGACGAGA<br>CAGCCACCATCGTGGAATTTCTGAACCGGTGGATCACC<br>TTCTGCCAGTCCATCATCTCCACCCTGACCTCCACCTC<br>CGGCATGTCCGTGGGCTGGATCCGGCAGCCTCCTGGCA<br>AGGCCCTGGAGTGGCTGGCCGACATTTGGTGGGACGAC<br>AAGAAGGACTACAACCCCAGCCTGAAGTCCCGGCTGAC<br>CATCTCCAAGGACACCTCCAAGAACCAAGTGGTGCTGA<br>AAGTGACCAACATGGACCCCGCCGACACCGCCACCTAC<br>TACTGCGCCCGGTCCATGATCACCAACTGGTACTTCGA<br>CGTGTGGGGCGCTGGCACCACCGTGACCGTGTCCTCT |
| SEQ ID NO: 4 | IL2 mutein protein, the mutein amino acid is bolded and underlined | APTSSSTKKTQLQLEHLLLDLQMILNGINNYKNPKLTA<br>MLTFKFYMPKKATELKHLQCLEEELKPLEEVLNLAQSK<br>NFHLRPRDLISNINVIVLELKGSETTFMCEYADETATI<br>VEFLNRWITFCQSIISTLT |

TABLE 1 -continued

| SEQ ID NO: 5 | IL2 mutein DNA | GCCCCTACCTCCTCCAGCACCAAGAAAACCCAGCTGCAGCTCGAACATCTGCTGCTGGACCTGCAGATGATCCTGAACGGCATCAACAACTACAAGAACCCCAAGCTGACCCGAATGCTGACCGCCAAGTTCTACATGCCCAAGAAGGCCACCGAGCTGAAACATCTGCAGTGCCTGGAAGAGGAACTGAAGCCCCTGGAAGAAGTGCTGAACCTGGCCCAGTCCAAGAACTTCCACCTGAGGCCTCGGGACCTGATCTCCAACATCAACGTGATCGTGCTGGAACTGAAGGGCTCCGAGACAACCTTCATGTGCGAGTACGCCGACGAGACAGCCACCATCGTGGAATTTCTGAACCGGTGGATCACCTTCTGCCAGTCCATCATCTCCACCCTGACC |
| --- | --- | --- |
| SEQ ID NO: 6 | IL2 mutein protein, the mutein amino acid is bolded and underlined | APTSSSTKKTQLQLEHLLLDLQMILNGINNYKNPKLTRMLTAKFYMPKKATELKHLQCLEEELKPLEEVLNLAQSKNFHLRPRDLISNINVIVLELKGSETTFMCEYADETATIVEFLNRWITFCQSIISTLT |

TABLE 2

IgG.IL2R67A.H1

| SEQ ID NO: 7 (Combined) | HCDR1 | GFSLAPTSSSTKKTQLQLEHLLLDLQMILNGINNYKNPKLTAMLTFKFYMPKKATELKHLQCLEEELKPLEEVLNLAQSKNFHLRPRDLISNINVIVLELKGSETTFMCEYADETATIVEFLNRWITFCQSIISTLTSTSGMSVG |
| --- | --- | --- |
| SEQ ID NO: 8 (Combined) | HCDR2 | DIWWDDKKDYNPSLKS |
| SEQ ID NO: 9 (Combined) | HCDR3 | SMITNWYFDV |
| SEQ ID NO: 10 (Kabat) | HCDR1 | APTSSSTKKTQLQLEHLLLDLQMILNGINNYKNPKLTAMLTFKFYMPKKATELKHLQCLEEELKPLEEVINLAQSKNFHLRPRDLISNINVIVIELKGSETTFMCEYADETATIVEFLNRWITFCQSIISTLTSTSGMSVG |
| SEQ ID NO: 11 (Kabat) | HCDR2 | DIWWDDKKDYNPSLKS |
| SEQ ID NO: 12 (Kabat) | HCDR3 | SMITNWYFDV |
| SEQ ID NO: 13 (Chothia) | HCDR1 | GFSLAPTSSSTKKTQLQLEHLLLDLQMILNGINNYKNPKLTAMLTFKFYMPKKATELKHLQCLEEELKPLEEVLNLAQSKNFHLRPRDLISNINVIVLELKGSETTFMCEYADETATIVEFLNRWITFCQSIISTLTSTSGM |
| SEQ ID NO: 14 (Chothia) | HCDR2 | WWDDK |
| SEQ ID NO: 15 (Chothia) | HCDR3 | SMITNWYFDV |
| SEQ ID NO: 16 (IMGT) | HCDR1 | GFSLAPTSSSTKKTQLQLEHLLLDLQMILNGINNYKNPKLTAMLTFKFYMPKKATELKHLQCLEEELKPLEEVLNLAQSKNFHLRPRDLISNINVIVLELKGSETTFMCEYADETATIVEFLNRWITFCQSIISTLTSTSGMS |
| SEQ ID NO: 17 (IMGT) | HCDR2 | IWWDDKK |
| SEQ ID NO: 18 (IMGT) | HCDR3 | ARSMITNWYFDV |
| SEQ ID NO: 19 | VH | QVTLRESGPALVKPTQTLTLTCTFSGFSLAPTSSSTKKTQLQLEHLLLDLQMILNGINNYKNPKLTAMITFKFYMPKKATELKHLQCLEEELKPLEEVINLAQSKNFHLRPRDLISNINVIVIELKGSETTFMCEYADETATIVEFLNRWITFCQSIISTLTSTSGMSVGWIRQPPGKALEWLADIWWDDKKDYNPSLKSRLTISKDTSKNQVVLKVTNMDPADTATYYCARSMITNWYFDVWGAGTTVTVSS |
| SEQ ID NO: 20 | DNA VH | CAAGTCACACTGCGTGAAAGCGGCCCTGCCCTGGTCAAGCCCACCCAGACCCTGACCCTGACCTGCACCTTCTCCGGCTTCAGCCTGGCCCCTACCTCCTCCAGCACCAAGAAAACCCAGCTGCAGCTCGAACATCTGCTGCTGGACCTGCAGATGATCCTGAACGGCATCAACAACTACAAGAACCCCAAGCTGACCGCCATGCTGACCTTCAAGTTCTACATGCCCAAGAAGGCCACCGAGCTGAAACATCTGCAGTGCCTGGAAGAGGAACTGAAGCCCCTGGAAGAAGTGCTGAACCTGGCCCAGTCCAAGAACTTCCACCTGAGGCCTCGGGACCTGATCTCCAACATCAACGTGATCGTGCTGGAACTGAAGGGCTCCGAGACAACCTTCATGTGCGAGTACGCCGACGAGACAGCCACCATCGTGGAATTTCTGAACCGGTGGATCACCTTCTGCCAGTCCATCATCTCCACCCTGACCTCCACCTCCGGCATGTCCGTGGGCTGGATCCGGCAGCCTCCTGGCAAGGCCCTGGAGTGGCTGGCCGACATTTGGTGGGACGACAAGAAGGACTACAACCCCAGCCTGAAGTCCCGGCTGACCATCTCCAAGGACACCTCCAAGAACCAAGTGGTGCTGAAAGTGACCAACATGGACCCCGCCGACACCGCCACCTACTACTGCGCCCGGTCCATGATCACCAACTGGTACTTCGA |

TABLE 2 -continued

| SEQ ID NO: 21 | Heavy Chain | CGTGTGGGCGCTGGCACCACCGTGACCGTGTCCTCT<br>QVTLRESGPALVKPTQTLTLTCTFSGFSLAPTSSSTKK<br>TQLQLEHLLLDLQMILNGINNYKNPKLTAMITFKFYMP<br>KKATELKHLQCLEEELKPLEEVINLAQSKNFHLRPRDL<br>ISNINVIVIELKGSETTFMCEYADETATIVEFLNRWIT<br>FCQSIISTLTSTSGMSVGWIRQPPGKALEWLADIWWDD<br>KKDYNPSLKSRLTISKDTSKNQVVLKVTNMDPADTATY<br>YCARSMITNWYFDVWGAGTTVTVSSASTKGPSVFPLAP<br>SSKSTSGGTAALGCLVKDYFPEPVTVSWNSGALTSGVH<br>TFPAVLQSSGLYSLSSVVTVPSSSLGTQTYICNVNHKP<br>SNTKVDKRVEPKSCDKTHTCPPCPAPELLGGPSVFLFP<br>PKPKDTLMISRTPEVTCVVVAVSHEDPEVKFNWYVDGV<br>EVHNAKTKPREEQYNSTYRVVSVLTVLHQDWLNGKEYK<br>CKVSNKALAAPIEKTISKAKGQPREPQVYTLPPSREEM<br>TKNQVSLTCLVKGFYPSDIAVEWESNGQPENNYKTTPP<br>VLDSDGSFFLYSKLTVDKSRWQQGNVFSCSVMHEALHN<br>HYTQKSLSLSPGK |
| --- | --- | --- |
| SEQ ID NO: 22 | DNA Heavy Chain | CAAGTCACACTGCGTGAAAGCGGCCCTGCCCTGGTCAA<br>GCCCACCCAGACCCTGACCCTGACCTGCACCTTCTCCG<br>GCTTCAGCCTGGCCCCTACCTCCTCCAGCACCAAGAAA<br>ACCCAGCTGCAGCTCGAACATCTGCTGCTGGACCTGCA<br>GATGATCCTGAACGGCATCAACAACTACAAGAACCCCA<br>AGCTGACCGCCATGCTGACCTTCAAGTTCTACATGCCC<br>AAGAAGGCCACCGAGCTGAAACATCTGCAGTGCCTGGA<br>AGAGGAACTGAAGCCCCTGGAAGAAGTGCTGAACCTGG<br>CCCAGTCCAAGAACTTCCACCTGAGGCCTCGGGACCTG<br>ATCTCCAACATCAACGTGATCGTGCTGGAACTGAAGGG<br>CTCCGAGACAACCTTCATGTGCGAGTACGCCGACGAGA<br>CAGCCACCATCGTGGAATTTCTGAACCGGTGGATCACC<br>TTCTGCCAGTCCATCATCTCCACCCTGACCTCCACCTC<br>CGGCATGTCCGTGGGCTGGATCCGGCAGCCTCCTGGCA<br>AGGCCCTGGAGTGGCTGGCCGACATTTGGTGGGACGAC<br>AAGAAGGACTACAACCCCAGCCTGAAGTCCCGGCTGAC<br>CATCTCCAAGGACACCTCCAAGAACCAAGTGGTGCTGA<br>AAGTGACCAACATGGACCCCGCCGACACCGCCACCTAC<br>TACTGCGCCCGGTCCATGATCACCAACTGGTACTTCGA<br>CGTGTGGGGCGCTGGCACCACCGTGACCGTGTCCTCTG<br>CTAGCACCAAGGGCCCTCCGTGTTCCCTCTGGCCCCT<br>TCCAGCAAGTCTACCTCCGGCGGCACAGCTGCTCTGGG<br>CTGCCTGGTCAAGGACTACTTCCCTGAGCCTGTGACAG<br>TGTCCTGGAACTCTGGCGCCCTGACCTCTGGCGTGCAC<br>ACCTTCCCTGCCGTGCTGCAGTCCTCCGGCCTGTACTC<br>CCTGTCCTCCGTGGTCACAGTGCCTTCAAGCAGCCTGG<br>GCACCCAGACCTATATCTGCAACGTGAACCACAAGCCT<br>TCCAACACCAAGGTGGACAAGCGGGTGGAGCCTAAGTC<br>CTGCGACAAGACCCACACCTGTCCTCCCTGCCCTGCTC<br>CTGAACTGCTGGGCGGCCCTTCTGTGTTCCTGTTCCCT<br>CCAAAGCCCAAGGACACCCTGATGATCTCCCGGACCCC<br>TGAAGTGACCTGCGTGGTGGTGGCCGTGTCCCACGAGG<br>ATCCTGAAGTGAAGTTCAATTGGTACGTGGACGGCGTG<br>GAGGTGCACAACGCCAAGACCAAGCCTCGGGAGGAACA<br>GTACAACTCCACCTACCGGGTGGTGTCCGTGCTGACCG<br>TGCTGCACCAGGACTGGCTGAACGGCAAAGAGTACAAG<br>TGCAAAGTCTCCAACAAGGCCCTGGCCGCCCCTATCGA<br>AAAGACAATCTCCAAGGCCAAGGGCCAGCCTAGGGAAC<br>CCCAGGTGTACACCCTGCCACCCAGCCGGGAGGAAATG<br>ACCAAGAACCAGGTGTCCCTGACCTGTCTGGTCAAGGG<br>CTTCTACCCTTCCGATATCGCCGTGGAGTGGGAGTCTA<br>ACGGCCAGCCTGAGAACAACTACAAGACCACCCCTCCT<br>GTGCTGGACTCCGACGGCTCCTTCTTCCTGTACTCCAA<br>ACTGACCGTGGACAAGTCCCGGTGGCAGCAGGGCAACG<br>TGTTCTCCTGCTCCGTGATGCACGAGGCCCTGCACAAC<br>CACTACACCCAGAAGTCCCTGTCCCTGTCCCCGGCAA<br>G |
| SEQ ID NO: 23 (Combined) | LCDR1 | KAQLSVGYMH |
| SEQ ID NO: 24 (Combined) | LCDR2 | DTSKLAS |
| SEQ ID NO: 25 (Combined) | LCDR3 | FQGSGYPFT |
| SEQ ID NO: 26 (Kabat) | LCDR1 | KAQLSVGYMH |
| SEQ ID NO: 27 (Kabat) | LCDR2 | DTSKLAS |
| SEQ ID NO: 28 (Kabat) | LCDR3 | FQGSGYPFT |
| SEQ ID NO: 29 (Chothia) | LCDR1 | QLSVGY |
| SEQ ID NO: 30 (Chothia) | LCDR2 | DTS |
| SEQ ID NO: 31 (Chothia) | LCDR3 | GSGYPF |
| SEQ ID NO: 32 (IMGT) | LCDR1 | LSVGY |

TABLE 2 -continued

| SEQ ID NO: 33 (IMGT) | LCDR2 | DTS |
|---|---|---|
| SEQ ID NO: 34 (IMGT) | LCDR3 | FQGSGYPFT |
| SEQ ID NO: 35 | VL | DIQMTQSPSTLSASVGDRVTITCKAQLSVGYMHWYQQK<br>PGKAPKLLIYDTSKLASGVPSRFSGSGSGTEFTLTISS<br>LQPDDFATYYCFQGSGYPFTEGGGTKLEIK |
| SEQ ID NO: 36 | DNA VL | GACATCCAGATGACCCAGAGCCCCTCCACCCTGTCCGC<br>CTCCGTGGGCGACAGAGTGACCATCACTTGCAAGGCCC<br>AGCTGTCCGTGGGCTACATGCACTGGTATCAGCAGAAG<br>CCCGGCAAGGCCCCTAAGCTGCTGATCTACGACACCTC<br>CAAGCTGGCCTCCGGCGTGCCCTCCAGATTCTCCGGCT<br>CTGGCTCCGGCACCGAGTTCACCCTGACCATCTCCAGC<br>CTGCAGCCCGACGACTTCGCCACCTACTACTGTTTTCA<br>AGGCTCCGGCTACCCCTTCACCTTCGGCGGAGGCACCA<br>AGCTGGAAATCAAG |
| SEQ ID NO: 37 | Light<br>Chain | DIQMTQSPSTLSASVGDRVTITCKAQLSVGYMHWYQQK<br>PGKAPKLLIYDTSKLASGVPSRFSGSGSGTEFTLTISS<br>LQPDDFATYYCFQGSGYPFTEGGGTKLEIKRTVAAPSV<br>FIFPPSDEQLKSGTASVVCLLNNFYPREAKVQWKVDNA<br>LQSGNSQESVTEQDSKDSTYSLSSTLTLSKADYEKHKV<br>YACEVTHQGLSSPVTKSFNRGEC |
| SEQ ID NO: 38 | DNA<br>Light<br>Chain | GACATCCAGATGACCCAGAGCCCCTCCACCCTGTCCGC<br>CTCCGTGGGCGACAGAGTGACCATCACTTGCAAGGCCC<br>AGCTGTCCGTGGGCTACATGCACTGGTATCAGCAGAAG<br>CCCGGCAAGGCCCCTAAGCTGCTGATCTACGACACCTC<br>CAAGCTGGCCTCCGGCGTGCCCTCCAGATTCTCCGGCT<br>CTGGCTCCGGCACCGAGTTCACCCTGACCATCTCCAGC<br>CTGCAGCCCGACGACTTCGCCACCTACTACTGTTTTCA<br>AGGCTCCGGCTACCCCTTCACCTTCGGCGGAGGCACCA<br>AGCTGGAAATCAAGCGTACGGTGGCCGCTCCCAGCGTG<br>TTCATCTTCCCCCCCAGCGACGAGCAGCTGAAGAGCGG<br>CACCGCCAGCGTGGTGTGCCTGCTGAACAACTTCTACC<br>CCCGGGAGGCCAAGGTGCAGTGGAAGGTGGACAACGCC<br>CTGCAGAGCGGCAACAGCCAGGAGAGCGTCACCGAGCA<br>GGACAGCAAGGACTCCACCTACAGCCTGAGCAGCACCC<br>TGACCCTGAGCAAGGCCGACTACGAGAAGCATAAGGTG<br>TACGCCTGCGAGGTGACCCACCAGGGCCTGTCCAGCCC<br>CGT GACCAAGAGCTTCAACAGGGGCGAGTGC |

IgG.IL2F71A.H1

| SEQ ID NO: 39<br>(Combined) | HCDR1 | GFSLAPTSSSTKKTQLQLEHLLLDLQMILNGINNYKNP<br>KLTRMLTAKFYMPKKATELKHLQCLEEELKPLEEVLNL<br>AQSKNFHLRPRDLISNINVIVLELKGSETTFMCEYADE<br>TATIVEFLNRWITFCQSIISTLTSTSGMSVG |
|---|---|---|
| SEQ ID NO: 40<br>(Combined) | HCDR2 | DIWWDDKKDYNPSLKS |
| SEQ ID NO: 41<br>(Combined) | HCDR3 | SMITNWYFDV |
| SEQ ID NO: 42 (Kabat) | HCDR1 | APTSSSTKKTQLQLEHLLLDLQMILNGINNYKNPKLTR<br>MLTAKFYMPKKATELKHLQCLEEELKPLEEVINLAQSK<br>NFHLRPRDLISNINVIVIELKGSETTFMCEYADETATI<br>VEFLNRWITFCQSIISTLTSTSGMSVG |
| SEQ ID NO: 43 (Kabat) | HCDR2 | DIWWDDKKDYNPSLKS |
| SEQ ID NO: 44 (Kabat) | HCDR3 | SMITNWYFDV |
| SEQ ID NO: 45<br>(Chothia) | HCDR1 | GFSLAPTSSSTKKTQLQLEHLLLDLQMILNGINNYKNP<br>KLTRMLTAKFYMPKKATELKHLQCLEEELKPLEEVLNL<br>AQSKNFHLRPRDLISNINVIVLELKGSETTFMCEYADE<br>TATIVEFLNRWITFCQSIISTLTSTSGM |
| SEQ ID NO: 46<br>(Chothia) | HCDR2 | WWDDK |
| SEQ ID NO: 47<br>(Chothia) | HCDR3 | SMITNWYFDV |
| SEQ ID NO: 48 (IMGT) | HCDR1 | GFSLAPTSSSTKKTQLQLEHLLLDLQMILNGINNYKNP<br>KLTRMLTAKFYMPKKATELKHLQCLEEELKPLEEVLNL<br>AQSKNFHLRPRDLISNINVIVLELKGSETTFMCEYADE<br>TATIVEFLNRWITFCQSIISTLTSTSGMS |
| SEQ ID NO: 49 (IMGT) | HCDR2 | IWWDDKK |
| SEQ ID NO: 50 (IMGT) | HCDR3 | ARSMITNWYFDV |
| SEQ ID NO: 51 | VH | QVTLRESGPALVKPTQTLTLTCTFSGFSLAPTSSSTKK<br>TQLQLEHLLLDLQMILNGINNYKNPKLTRMLTAKFYMP<br>KKATELKHLQCLEEELKPLEEVINLAQSKNFHLRPRDL<br>ISNINVIVIELKGSETTFMCEYADETATIVEFLNRWIT<br>FCQSIISTLTSTSGMSVGWIRQPPGKALEWLADIWWDD<br>KKDYNPSLKSRLTISKDTSKNQVVLKVTNMDPADTATY<br>YCARSMITNWYFDVWGAGTTVTVSS |
| SEQ ID NO: 52 | DNA VH | CAAGTCACACTGCGTGAAAGCGGCCCTGCCCTGGTCAA<br>GCCCACCCAGACCCTGACCCTGACCTGCACCTTCTCCG<br>GCTTCAGCCTGGCCCCTACCTCCTCCAGCACCAAGAAA<br>ACCCAGCTGCAGCTCGAACATCTGCTGCTGGACCTGCA<br>GATGATCCTGAACGGCATCAACAACTACAAGAACCCCA |

TABLE 2-continued

| | | |
|---|---|---|
| | | AGCTGACCCGGATGCTGACCGCCAAGTTCTACATGCCC<br>AAGAAGGCCACCGAGCTGAAACATCTGCAGTGCCTGGA<br>AGAGGAACTGAAGCCCCTGGAAGAAGTGCTGAACCTGG<br>CCCAGTCCAAGAACTTCCACCTGAGGCCTCGGGACCTG<br>ATCTCCAACATCAACGTGATCGTGCTGGAACTGAAGGG<br>CTCCGAGACAACCTTCATGTGCGAGTACGCCGACGAGA<br>CAGCCACCATCGTGGAATTTCTGAACCGGTGGATCACC<br>TTCTGCCAGTCCATCATCTCCACCCTGACCTCCACCTC<br>CGGCATGTCCGTGGGCTGGATCCGGCAGCCTCCTGGCA<br>AGGCCCTGGAGTGGCTGGCCGACATTTGGTGGGACGAC<br>AAGAAGGACTACAACCCCAGCCTGAAGTCCCGGCTGAC<br>CATCTCCAAGGACACCTCCAAGAACCAAGTGGTGCTGA<br>AAGTGACCAACATGGACCCCGCCGACACCGCCACCTAC<br>TACTGCGCCCGGTCCATGATCACCAACTGGTACTTCGA<br>CGTGTGGGGCGCTGGCACCACCGTGACCGTGTCCTCT |
| SEQ ID NO: 53 | Heavy<br>Chain | QVTLRESGPALVKPTQTLTLTCTFSGFSLAPTSSSTKK<br>TQLQLEHLLLDLQMILNGINNYKNPKLTRMLTAKFYMP<br>KKATELKHLQCLEEELKPLEEVINLAQSKNFHLRPRDL<br>ISNINVIVIELKGSETTFMCEYADETATIVEFLNRWIT<br>FCQSIISTLTSTSGMSVGWIRQPPGKALEWLADIWWDD<br>KKDYNPSLKSRLTISKDTSKNQVVLKVTNMDPADTATY<br>YCARSMITNWYFDVWGAGTTVTVSSASTKGPSVFPLAP<br>SSKSTSGGTAALGCLVKDYFPEPVTVSWNSGALTSGVH<br>TFPAVLQSSGLYSLSSVVTVPSSSLGTQTYICNVNHKP<br>SNTKVDKRVEPKSCDKTHTCPPCPAPELLGGPSVFLFP<br>PKPKDTLMISRTPEVTCVVVAVSHEDPEVKFNWYVDGV<br>EVHNAKTKPREEQYNSTYRVVSVLTVLHQDWLNGKEYK<br>CKVSNKALAAPIEKTISKAKGQPREPQVYTLPPSREEM<br>TKNQVSLTCLVKGFYPSDIAVEWESNGQPENNYKTTPP<br>VLDSDGSFFLYSKLTVDKSRWQQGNVFSCSVMHEALHN<br>HYTQKSLSLSPGK |
| SEQ ID NO: 54 | DNA<br>Heavy<br>Chain | CAAGTCACACTGCGTGAAAGCGGCCCTGCCCTGGTCAA<br>GCCCACCCAGACCCTGACCCTGACCTGCACCTTCTCCG<br>GCTTCAGCCTGGCCCCTACCTCCTCCAGCACCAAGAAA<br>ACCCAGCTGCAGCTCGAACATCTGCTGCTGGACCTGCA<br>GATGATCCTGAACGGCATCAACAACTACAAGAACCCCA<br>AGCTGACCCGGATGCTGACCGCCAAGTTCTACATGCCC<br>AAGAAGGCCACCGAGCTGAAACATCTGCAGTGCCTGGA<br>AGAGGAACTGAAGCCCCTGGAAGAAGTGCTGAACCTGG<br>CCCAGTCCAAGAACTTCCACCTGAGGCCTCGGGACCTG<br>ATCTCCAACATCAACGTGATCGTGCTGGAACTGAAGGG<br>CTCCGAGACAACCTTCATGTGCGAGTACGCCGACGAGA<br>CAGCCACCATCGTGGAATTTCTGAACCGGTGGATCACC<br>TTCTGCCAGTCCATCATCTCCACCCTGACCTCCACCTC<br>CGGCATGTCCGTGGGCTGGATCCGGCAGCCTCCTGGCA<br>AGGCCCTGGAGTGGCTGGCCGACATTTGGTGGGACGAC<br>AAGAAGGACTACAACCCCAGCCTGAAGTCCCGGCTGAC<br>CATCTCCAAGGACACCTCCAAGAACCAAGTGGTGCTGA<br>AAGTGACCAACATGGACCCCGCCGACACCGCCACCTAC<br>TACTGCGCCCGGTCCATGATCACCAACTGGTACTTCGA<br>CGTGTGGGGCGCTGGCACCACCGTGACCGTGTCCTCTG<br>CTAGCACCAAGGGCCCCTCCGTGTTCCCTCTGGCCCCT<br>TCCAGCAAGTCTACCTCCGGCGGCACAGCTGCTCTGGG<br>CTGCCTGGTCAAGGACTACTTCCCTGAGCCTGTGACAG<br>TGTCCTGGAACTCTGGCGCCCTGACCTCTGGCGTGCAC<br>ACCTTCCCTGCCGTGCTGCAGTCCTCCGGCCTGTACTC<br>CCTGTCCTCCGTGGTCACAGTGCCTTCAAGCAGCCTGG<br>GCACCCAGACCTATATCTGCAACGTGAACCACAAGCCT<br>TCCAACACCAAGGTGGACAAGCGGGTGGAGCCTAAGTC<br>CTGCGACAAGACCCACACCTGTCCTCCCTGCCCTGCTC<br>CTGAACTGCTGGGCGGCCCTTCTGTGTTCCTGTTCCCT<br>CCAAAGCCCAAGGACACCCTGATGATCTCCCGGACCCC<br>TGAAGTGACCTGCGTGGTGGTGGCCGTGTCCCACGAGG<br>ATCCTGAAGTGAAGTTCAATTGGTACGTGGACGGCGTG<br>GAGGTGCACAACGCCAAGACCAAGCCTCGGGAGGAACA<br>GTACAACTCCACCTACCGGGTGGTGTCCGTGCTGACCG<br>TGCTGCACCAGGACTGGCTGAACGGCAAAGAGTACAAG<br>TGCAAAGTCTCCAACAAGGCCCTGGCCGCCCCTATCGA<br>AAAGACAATCTCCAAGGCCAAGGGCCAGCCTAGGGAAC<br>CCCAGGTGTACACCCTGCCACCCAGCCGGGAGGAAATG<br>ACCAAGAACCAGGTGTCCCTGACCTGTCTGGTCAAGGG<br>CTTCTACCCTTCCGATATCGCCGTGGAGTGGGAGTCTA<br>ACGGCCAGCCTGAGAACAACTACAAGACCACCCCTCCT<br>GTGCTGGACTCCGACGGCTCCTTCTTCCTGTACTCCAA<br>ACTGACCGTGGACAAGTCCCGGTGGCAGCAGGGCAACG<br>TGTTCTCCTGCTCCGTGATGCACGAGGCCCTGCACAAC<br>CACTACACCCAGAAGTCCCTGTCCCTGTCTCCCGGCAA<br>G |
| SEQ ID NO: 55<br>(Combined) | LCDR1 | KAQLSVGYMH |

TABLE 2 -continued

| SEQ ID NO: 56 (Combined) | | LCDR2 | DTSKLAS |
|---|---|---|---|
| SEQ ID NO: 57 (Combined) | | LCDR3 | FQGSGYPFT |
| SEQ ID NO: 58 | (Kabat) | LCDR1 | KAQLSVGYMH |
| SEQ ID NO: 59 | (Kabat) | LCDR2 | DTSKLAS |
| SEQ ID NO: 60 | (Kabat) | LCDR3 | FQGSGYPFT |
| SEQ ID NO: 61 (Chothia) | | LCDR1 | QLSVGY |
| SEQ ID NO: 62 (Chothia) | | LCDR2 | DTS |
| SEQ ID NO: 63 (Chothia) | | LCDR3 | GSGYPF |
| SEQ ID NO: 64 | (IMGT) | LCDR1 | LSVGY |
| SEQ ID NO: 65 | (IMGT) | LCDR2 | DTS |
| SEQ ID NO: 66 | (IMGT) | LCDR3 | FQGSGYPFT |
| SEQ ID NO: 67 | | VL | DIQMTQSPSTLSASVGDRVTITCKAQLSVGYMHWYQQK PGKAPKLLIYDTSKLASGVPSRFSGSGSGTEFTLTISS LQPDDFATYYCFQGSGYPFTFGGGTKLEIK |
| SEQ ID NO: 68 | | DNA VL | GACATCCAGATGACCCAGAGCCCCTCCACCCTGTCCGC CTCCGTGGGCGACAGAGTGACCATCACTTGCAAGGCCC AGCTGTCCGTGGGCTACATGCACTGGTATCAGCAGAAG CCCGGCAAGGCCCCTAAGCTGCTGATCTACGACACCTC CAAGCTGGCCTCCGGCGTGCCCTCCAGATTCTCCGGCT CTGGCTCCGGCACCGAGTTCACCCTGACCATCTCCAGC CTGCAGCCCGACGACTTCGCCACCTACTACTGTTTTCA AGGCTCCGGCTACCCCTTCACCTTCGGCGGAGGCACCA AGCTGGAAATCAAG |
| SEQ ID NO: 69 | | Light Chain | DIQMTQSPSTLSASVGDRVTITCKAQLSVGYMHWYQQK PGKAPKLLIYDTSKLASGVPSRFSGSGSGTEFTLTISS LQPDDFATYYCFQGSGYPFTFGGGTKLEIKRTVAAPSV FIFPPSDEQLKSGTASVVCLLNNFYPREAKVQWKVDNA LQSGNSQESVTEQDSKDSTYSLSSTLTLSKADYEKHKV YACEVTHQGLSSPVTKSFNRGEC |
| SEQ ID NO: 70 | | DNA Light Chain | GACATCCAGATGACCCAGAGCCCCTCCACCCTGTCCGC CTCCGTGGGCGACAGAGTGACCATCACTTGCAAGGCCC AGCTGTCCGTGGGCTACATGCACTGGTATCAGCAGAAG CCCGGCAAGGCCCCTAAGCTGCTGATCTACGACACCTC CAAGCTGGCCTCCGGCGTGCCCTCCAGATTCTCCGGCT CTGGCTCCGGCACCGAGTTCACCCTGACCATCTCCAGC CTGCAGCCCGACGACTTCGCCACCTACTACTGTTTTCA AGGCTCCGGCTACCCCTTCACCTTCGGCGGAGGCACCA AGCTGGAAATCAAGCGTACGGTGGCCGCTCCCAGCGTG TTCATCTTCCCCCCCAGCGACGAGCAGCTGAAGAGCGG CACCGCCAGCGTGGTGTGCCTGCTGAACAACTTCTACC CCCGGGAGGCCAAGGTGCAGTGGAAGGTGGACAACGCC CTGCAGAGCGGCAACAGCCAGGAGAGCGTCACCGAGCA GGACAGCAAGGACTCCACCTACAGCCTGAGCAGCACCC TGACCCTGAGCAAGGCCGACTACGAGAAGCATAAGGTG TACGCCTGCGAGGTGACCCACCAGGGCCTGTCCAGCCC CGTGACCAAGAGCTTCAACAGGGGCGAGTGC |

Example 2: IgG.IL2R67A.Hl has Extended Half-Life Compared to PROLEUKIN®-(IL-2)

Naive CD-I mice were dosed I.P. and blood collected from all animals at pre-dose, 1 hour, 3, 7, 24, 31, 48, 55 and 72 hours post-dose. Blood samples were centrifuged, and plasma samples obtained. Resulting plasma samples were transferred into a single polypropylene tube and frozen at −80° C. All samples were analyzed, and concentrations of IgG.IL2R67 A.HI in plasma measured using immuno-assays. Pharmacokinetic parameters such as half-life were calculated. Each sample was run in duplicate, with each of the duplicated analyses requiring 5 µL of sample that had been diluted 1:20. Capture: goat anti-human IL-2 biotinylated antibody (R&D Systems BAF202) Detect: Alexa 647 anti-human IL-2, Clone MQ1-17H12 (Biolegend #500315) All immunoassays were conducted using an automated immunoassay: GYROLAB® Bioaffy200 with Gyros CD-200s. As shown in the graph in FIG. 2, the half-life of IgG.IL2R67A.HI is approximately 12 hours and then diminishing over the next 48 hours. The PROLEUKIN® half-life could not be shown on this graph as its half-life is approximately 4 hours.

Example 3: IgG.IL2R67 A.HJ Selectively Expands CD8 T Effectors and is Better Tolerated than IL-2 Fc or PROLEUKIN®—in Normal B6 Mice IgG.IL2R67 A.HI augments CD8+T effectors over Tregs without causing the adverse events seen with PROLEUKIN® administration. After dosing mice on day 1, CD8+T effector expansion was monitored at day 4, day 8 and day 11. At each timepoint, the CD8+T effector cell population was greatly expanded, without Treg expansion. This was in contrast to PROLEUKIN® and an IL-2Fc fusion, in which mortality and morbidity were observed at equimolar doses of IL-2.

B6 female mice were administered PROLEUKIN® (5x weekly), IL-2 Fe and IgG.IL2R67 A.HI (1x/week) at equimolar concentrations. Eight days after first treatment, spleens were processed to obtain a single cell suspension and washed in RPMI (10% FBS). Red blood cells were lysed with Red Blood Cell Lysis Buffer (Sigma #R7757) and cells counted for cell number and viability. FACS staining was performed under standard protocols using FACS buffer (1×PBS+0.5% BSA+0.05% sodium azide). Cells were stained with surface antibodies: Rat anti-mouse CD3-efluor 450 (Ebioscience #48-0032), Rat anti-mouse CD4-Pacific Blue (BD Pharmingen #558107), Rat anti-mouse CD8-PerCp (BD Pharmingen #553036), Rat anti-mouse CD44 F1TC (Pharmingen #553133), Rat anti-mouse CD25-APC (Ebioscience #17-0251), Rat anti-mouse Nk1.1 (Ebioscience #95-5941) and subsequently fixed/permeabilized and stained for FoxP3 according to the anti-Mouse/Rat FoxP3 Staining Set PE (Ebioscience 1472-5775). Cells were analyzed on the flow cytometer Becton-Dickinson LSR FORTESSA® or Becton-Dickinson FACS LSR II, and data analyzed with flow cytometry data software package FLOWJO® software.

Figure 3A:
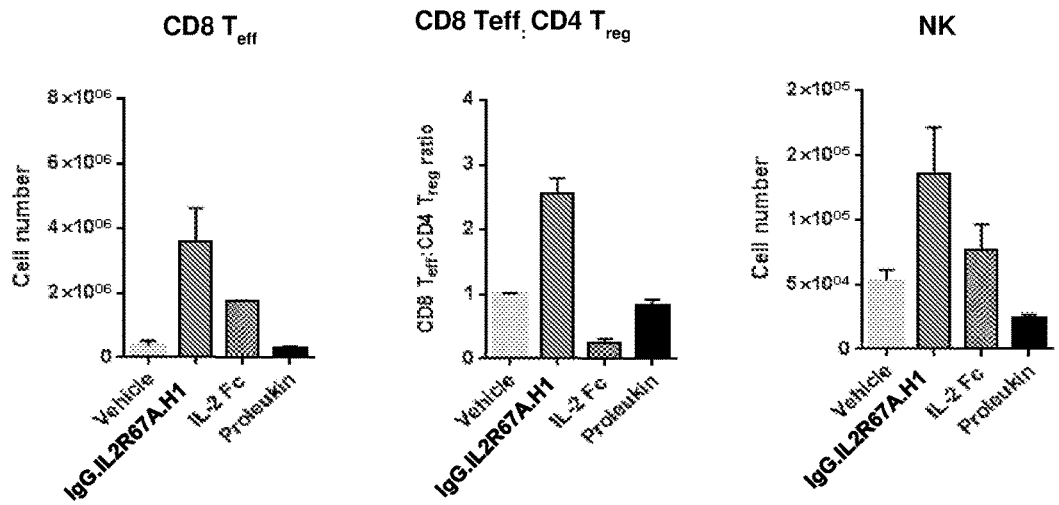
FIGS. 3A-3C demonstrate that IgG.IL2R67A.HI expands CD8+T effector cells more effectively and with less toxicity than PROLEUKIN® or an IL2-Fc fusion molecule in C57BL/6 mice at a 100 µg equivalent dose, at day 4, day S and day 11 time points.
Figure 3B:
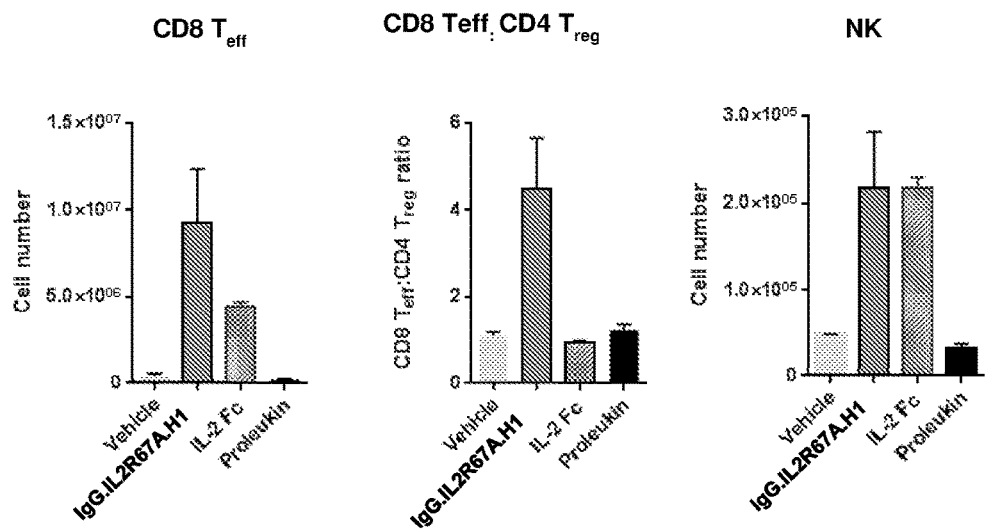
Figure 3C:
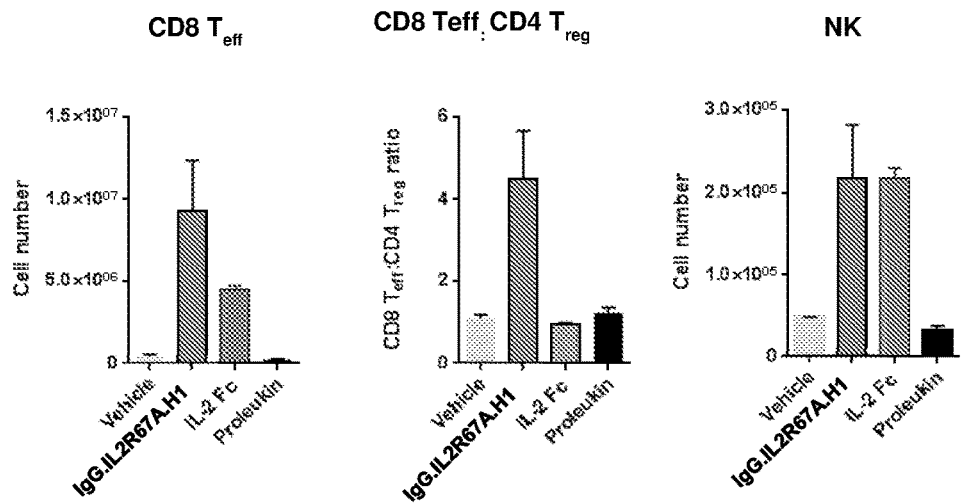
Figure 3D:
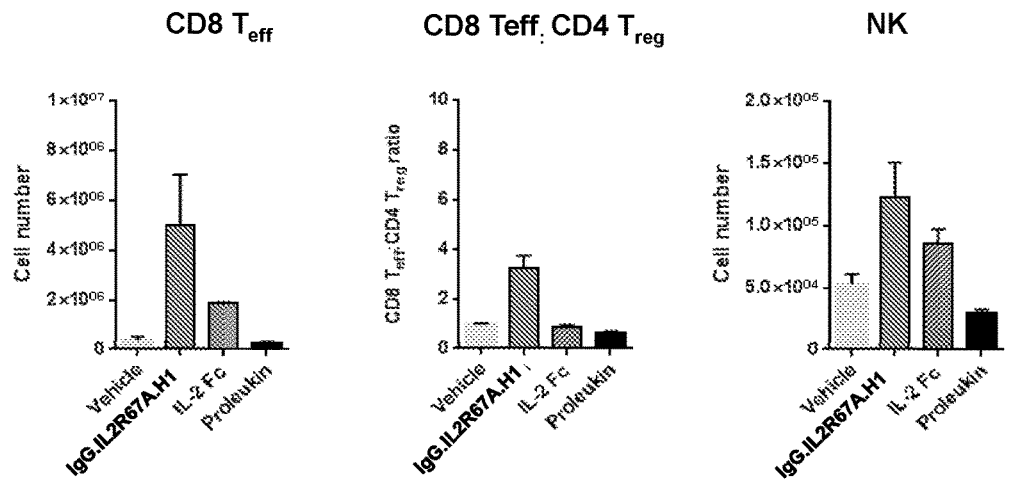
FIGS. 3D-3F demonstrate that IgG.IL2R67A.HI expands CD8+T effector cells more effectively and with less toxicity than PROLEUKIN® or an IL2-Fc fusion molecule in C57BL/6 mice at a 500 µg equivalent dose at day 4, day S and day 11 time points.
Figure 3E:
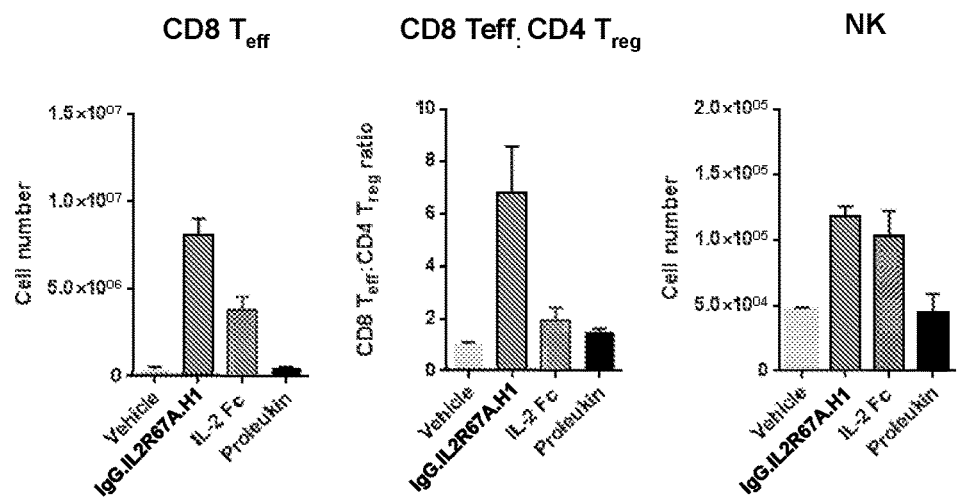
Figure 3F:
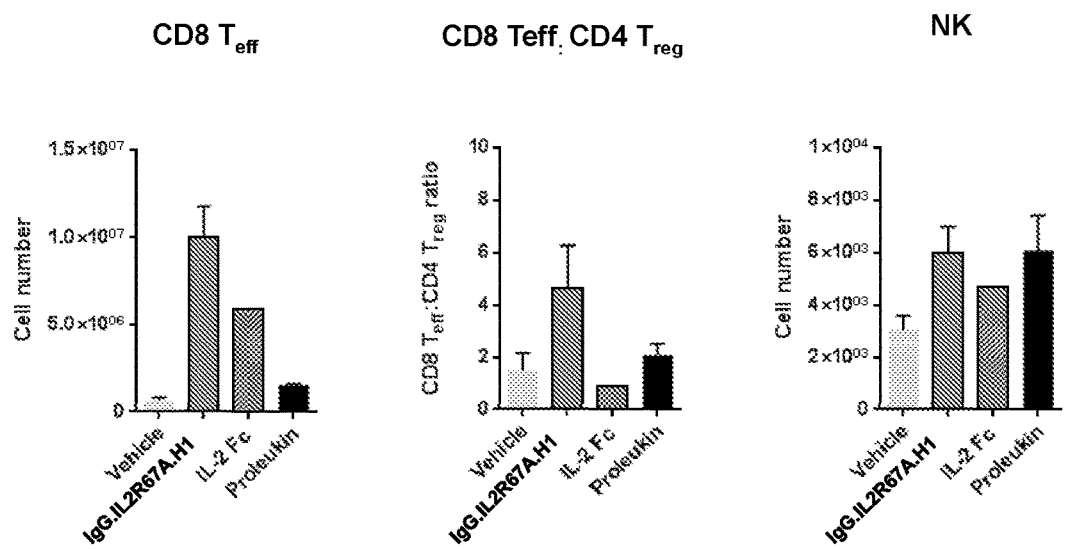

FIGS. 3A-3C shows the preferential expansion of CD8+T effector cells in B6female mice after administration of PROLEUKIN® (5× weekly), IL2-Fc and IgG.IL2R67A.HI (Ix/week) at PROLEUKIN® equimolar concentrations (IgG.IL2R67A.HI and IL2-Fc 100 µg-1 nmol IL2 equivalent). The data in the graphs demonstrate that CD8+T effector cells proliferate without similar proliferation of Tregs. Contrast this data to PROLEUKIN® which expanded both CD8+T effectors and Tregs. Note that IgG.IL2R67A.HI was superior in both absolute numbers of CD8+T effector cell expansion and in the ratio CD8+T effector cells:Tregs to an IL2-Fc fusion construct, demonstrating that there is a structural and functional basis for the IgG.IL2R67A.HI antibody cytokine engrafted protein. FIGS. 3D-3F shows that the beneficial effect of IgG.IL2R67A.HI is more apparent at higher doses.

When 500 µg (5 nmol IL2 equivalent) of IgG.IL2R67A.HI was administered to B6 mice, the preferential expansion of CD8+T effector cells was seen relative to Treg cells similar to the lower dose. However, in the IL2-Fc treatment group, mice were found dead after only a single dose at the higher level (data not shown). This indicates that IgG.IL2R67A.HI has a larger therapeutic index that IL2-Fc fusion constructs, and can be safely administered in a wider dosage range.

Figure 4A:
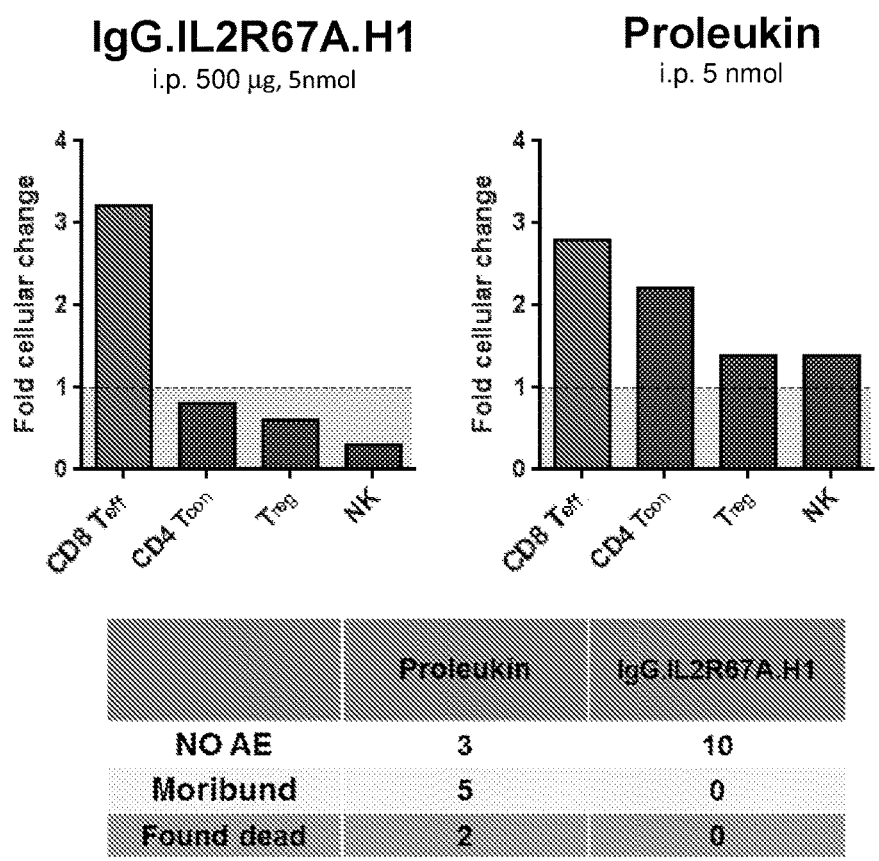
FIG. 4A shows that IgG.IL2R67A.HI selectively expands CD8+T effectors and is better tolerated than PROLEUKIN® in NOD mice.

Example 4: IgG.IL2R67 A.HJ Selectively Expands CD8 T Effector Cells, and is Better Tolerated than PROLEUKIN® in NOD Mice The non-obese diabetic (NOD) mouse develops type 1 diabetes spontaneously and is often used as an animal model for human type 1 diabetes. Using the same protocol for the B6 mice described in Example 3, IgG.IL2R67A.HI, IL2-Fc and PROLEUKIN® were administered to NOD mice at PROLEUKIN® equimolar equivalents. Again, administration of IgG.IL2R67 A.HI at this dose preferentially expanded CD8+T effector cells over Tregs as shown in the graph in FIG. 4A. In addition, administration of IgG.IL2R67A.HI showed no adverse events in NOD mice, while the PROLEUKIN® treated group had 5 moribund mice and 2 deaths. FIG. 4B is a graph reporting the dosages, fold cellular changes and cell type from the NOD mouse model.

Example 5: IgG.IL2R67 A.HJ Shows Single-Agent Efficacy in a CT26 Colon Tumor Mouse Model After studying the safety of IgG.IL2R67A.HI, its single-agent efficacy was tested in a CT26 mouse model. Murine CT26 cells are rapidly growing grade IV colon carcinoma cells, used in over 500 published studies and is one of the commonly used cell lines and models in drug development. CT26 (ATCC CRL-2638) cells were grown in sterile conditions in a 37° C. incubator with 5% CO2. The cells were cultured in RPMI 1640 media supplemented with 10% FBS. Cells were passed every 3-4 days. For the day of injection, cells were harvested (Passage 11) and re-suspended in HBSS at a concentration of $2.5 \times 10^6$/ml. Cells were Radii tested on for mycoplasma and murine viruses. Balbc mice were used. For each mouse, $0.25 \times 10^6$ cells were implanted with subcutaneously injection into right flank using a 28 g needle (100 µl injection volume). After implantation, animals were calipered and weighed 3 times per week once tumors were palpable. Caliper measurements were calculated using (L×W×W)/2. Mice were fed with normal diet and housed in SPF animal facility in accordance with the Guide for Care and Use of Laboratory Animals and regulations of the Institutional Animal Care and Use Committee.

When tumors reached about 100 mm³, mice were administered by intraperitoneal route 12.5-100 µs of lgG.IL2R67A.HI. Tumors were measured twice a week. Average tumor volumes were plotted using Prism 5 (GRAPHPAD ° software) software. An endpoint for efficacy studies was achieved when tumor size reached a volume of 1000 mm³ Following injection, mice were also closely monitored for signs of clinical deterioration. If for any reason mice showed any signs of morbidity, including respiratory distress, hunched posture, decreased activity, hind leg paralysis, tachypnea as a sign for pleural effusions, weight loss approaching 20% or 15% plus other signs, or if their ability to carry on normal activities (feeding, mobility), was impaired, mice were euthanized.

Figure 5:
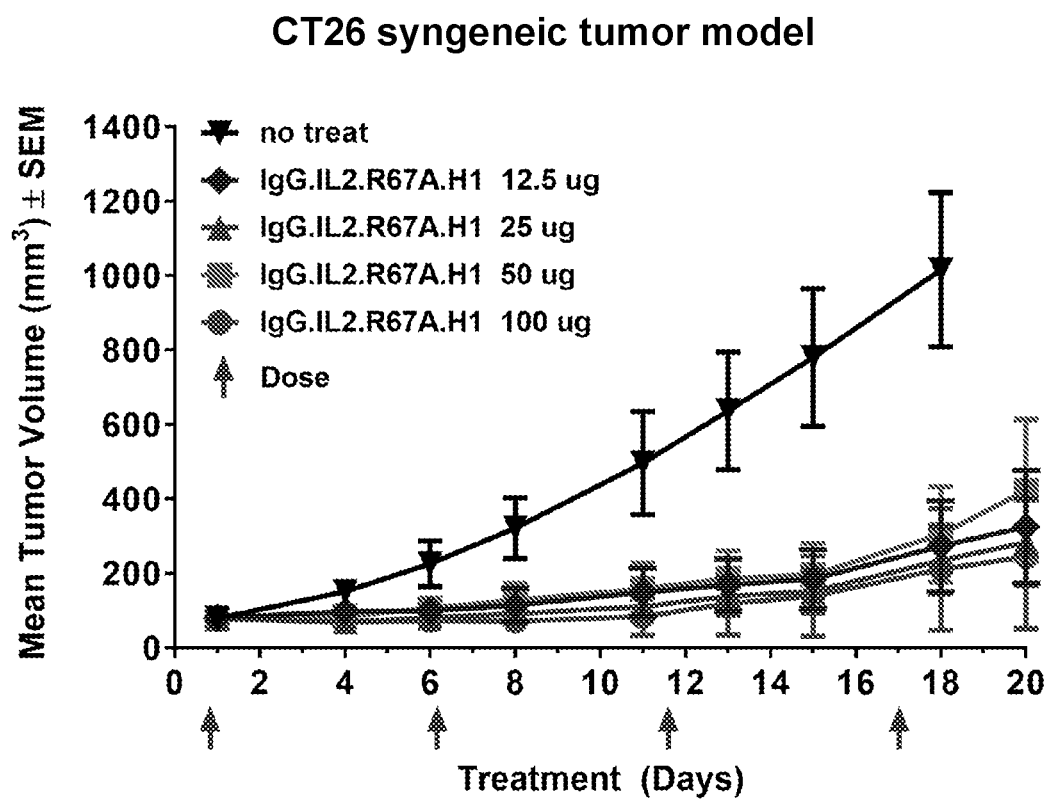
FIG. 5 shows a graph of single agent efficacy of IgG.IL2R67A.HI in a CT26 tumor model.

IgG.IL2R67 A.HI was efficacious in the CT26 mouse model at doses ranging from 12.5 µg to 100 µg, with 4 administrations of IgG.IL2R67A.HI over 17 days in a 20 day study. The tumor volume curves shown in FIG. 5 are indicative of the efficacy of IgG.IL2R67A.HI in this study, as tumor volumes were kept under 200 mm for 15 days and then under 400 mm for the remaining 5 days.

Example 6: IgG.IL2R67A.HJ and Additional Cancer Therapeutics Show Efficacy in a Bl 6 Mouse Model To assess the efficacy of IgG.IL2R67A.HI in combination with other cancer therapeutics, a B16F10 melanoma mouse model was used. B16F10 cells (ATCC CRL-6475) were grown in sterile conditions in a 37° C. incubator with 5% CO2 for two weeks. B16F10 cells were cultured in DMEM+ 10% FBS. Cells were harvested and re-suspended in FBS-free medium DMEM at a concentration of $1 \times 10^6$/100 µl. B16F10 cells were Radii tested for mycoplasma and murine viruses. Cells were implanted into the right flank of B6 mice using a 28 gauge needle (100 µl injection volume). After implant, mice were calipered and weighed 2 times per week once tumors were palpable. Caliper measurements were calculated using (L×W×W)/2.

In this study, IgG.IL2R67A.HI was used as a single agent or in combination with the TA99 antibody, which binds Trpl, an antigen that is expressed on B16F10 cells. An IL2-Fc fusion was administered as a single agent or in combination with the TA99 antibody. As a control, the TA99 antibody was administered as a single agent.

Figure 6:
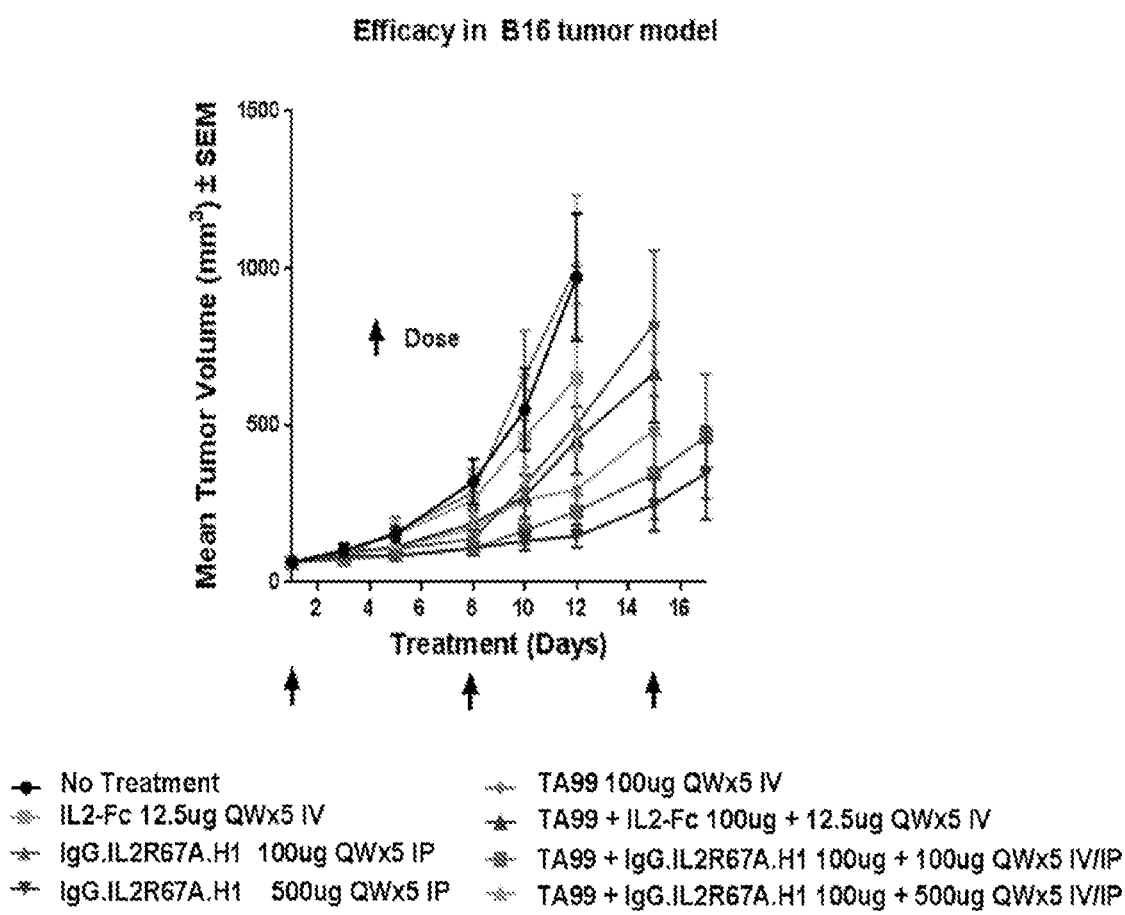
FIG. 6 presents the data of IgG.IL2R67A.HI either as a single agent or in combination with an antibody in a B16 melanoma mouse model. The graph shows that IgGIL2R67A.H1 in combination with TA99, an anti-TRPI antibody, is more efficacious than TA99 alone, an IL2-Fc fusion molecule alone, TA99 plus an IL2-Fc fusion. Synergy was seen with TA99 and IgG.IL2R67A.HI at the 100 and 500 Kg doses.

Surprisingly, IgG.IL2R67A.HI when administered as a single agent at a 500 µg dose was the most efficacious treatment in this model (FIG. 6). The next best treatment was the combination of lgG.IL2R67A.H1 (100 µg) and TA99.

This combination was more efficacious than IgGIL2F71A.H1 as a single agent at 100 μg, TA99 in combination with IgGIL2F71A.H1 at 500 μg and IL2-Fc as a single agent or as an IL2-Fc/TA99 combination. When TA99 was administered a single agent, it had no effect, and the mean tumor volume was similar to untreated control. This data demonstrates that IgG.IL2R67 A.HI is efficacious as a single agent in melanoma mouse tumor model, but it is also efficacious when paired with another anti-cancer agent.

Example 7: Activity of IgG.IL2R67A.HJ and IgG.IL2F71A.Hl in Human Cells

In order to test the activity of IgG.IL2R67A.HI on human CD8+T effectors, human peripheral blood mononuclear cells (PBMC) were assayed for pSTAT5 activity. PBMC cells were rested in serum-free test media, and plated. IgG.IL2R67A.HI, IgG.IL2F7IA.HI or PROLEUKIN® was added to the PBMCs, and incubated for 20 minutes at 37° C. After 20 min, cells were fixed with 1.6% formaldehyde, washed and stained with surface markers. After 30 minutes at room temperature, samples were washed and re-suspended cell pellets were permeabilized with −20° C. methanol, washed and stained for pSTAT5 and DNA intercalators. Cells were run on a mass cytometry application CYTOF® and data analyzed with flow cytometry data software package FLOWJO® software to quantify the level of pSTAT5 activity. The table in FIG. 7 demonstrates the preferential activation IgG.IL2R67A.HI has for CD8+T effector cells and minimizes the activation of Treg cells.

Example 8: Binding of Antibody Cytokine Engrafted Proteins

Figure 8:
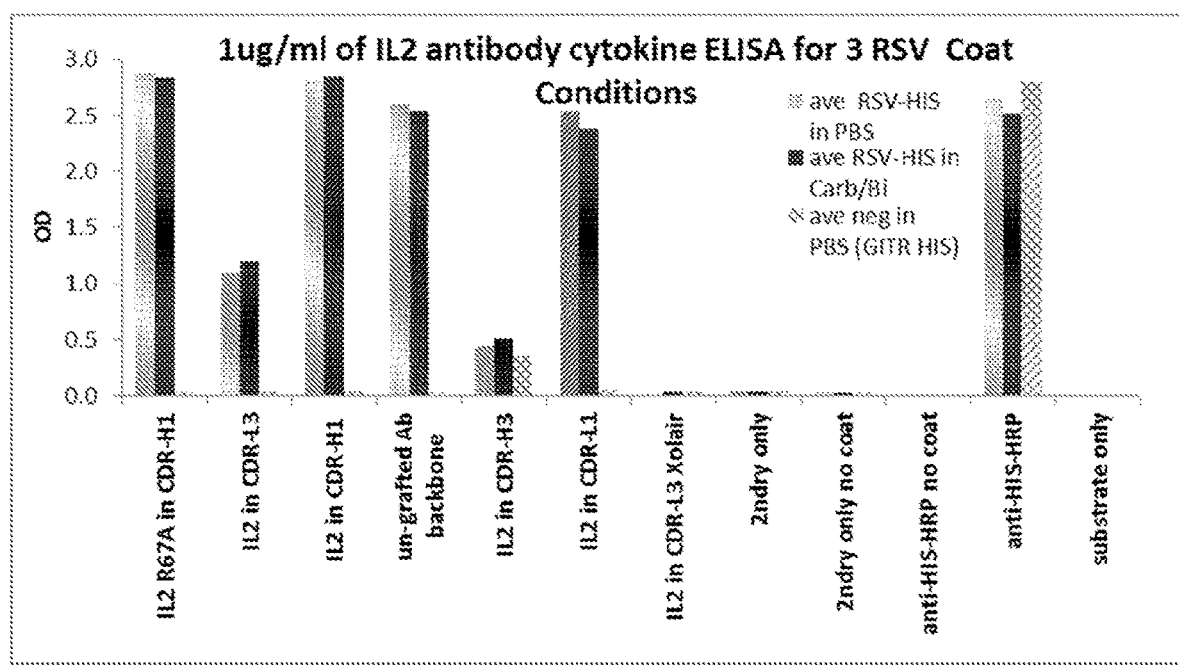
FIG. 8 shows a graph of ELISA data showing that when IL2 is engrafted into CDRHI of an anti-RSV antibody (IgG.IL2R67A.HI), RSV binding is maintained. However, binding to RSV is reduced when IL2 is engrafted into CDRL3 or CDRH3. When IL2 is engrafted into a different antibody backbone (Xolair), there is no binding to RSV.

IL2 sequences containing a mutein (SEQ ID NO:4) were inserted into CDR loops of an immunoglobulin chain scaffold. Antibody cytokine engrafted proteins were prepared using a variety of known immunoglobulin sequences which have been utilized in clinical settings as well as germline antibody sequences. One of the antibodies used has RSV as its antigen. To determine if engrafting IL2 into the CDRs of this antibody reduced or abrogated binding to RSV, an ELISA assay was run on RSV proteins either in PBS or a carbonate buffer. As shown in FIG. 8, this appears to be influenced by which CDR was chosen for IL2 engrafting. For example, IgG.IL2R67A.HI has RSV binding similar to the un-grafted (un-modified) original antibody. In contrast, engrafting IL2 into the light chain of CDR3 (CDR-L3) or into CDR-H3 reduces binding. As expected, IL2 engrafted into an irrelevant antibody (Xolair) produces no binding. This demonstrates that antibody cytokine engrafted proteins can retain binding to the original target of the antibody scaffold, or this binding can be reduced.

It is understood that the examples and embodiments described herein are for illustrative purposes and that various modifications or changes in light thereof will be suggested to persons skilled in the art and are to be included within the spirit and purview of this application and scope of the appended claims. All publications, sequence accession numbers, patents, and patent applications cited herein are hereby incorporated by reference in their entirety for all purposes.

What is claimed is:

1. An antibody cytokine engrafted protein comprising:
   (a) an IgG class heavy chain comprising an IgG class heavy chain variable region (VH), comprising Complementarity Determining Regions (CDR) HCDR1 comprising SEQ ID NO: 7, SEQ ID NO: 10, SEQ ID NO: 13, SEQ ID NO: 16, SEQ ID NO: 39, SEQ ID NO: 42, SEQ ID NO: 45, or SEQ ID NO: 48, HCDR2 comprising SEQ ID NO: 8, SEQ ID NO: 11, SEQ ID NO: 14, SEQ ID NO: 17, SEQ ID NO: 40, SEQ ID NO: 46 or SEQ ID NO: 49, and HCDR3 comprising SEQ ID NO: 9, SEQ ID NO: 12, SEQ ID NO: 15, SEQ ID NO: 18, SEQ ID NO: 41, SEQ ID NO: 44, SEQ ID NO: 47 or SEQ ID NO: 50, and wherein the HCDRs individually comprise between 0 to 1 substitution; and
   (b) an IgG class light chain comprising an IgG class light chain variable region (VL), comprising LCDR1 comprising SEQ ID NO: 23, SEQ ID NO: 26, SEQ ID NO: 29, SEQ ID NO: 32, SEQ ID NO: 55, SEQ ID NO: 58, SEQ ID NO: 61 or SEQ ID NO: 64, LCDR2 comprising SEQ ID NO: SEQ ID NO: 24, SEQ ID NO: 27, SEQ ID NO: 30, SEQ ID NO: 33, SEQ ID NO: 56, SEQ ID NO: 59, SEQ ID NO: 62 or SEQ ID NO: 65, and LCDR3 comprising SEQ ID NO: 25, SEQ ID NO: 28, SEQ ID NO: 31, SEQ ID NO: 34, SEQ ID NO: 57, SEQ ID NO: 60, SEQ ID NO: 63 or SEQ ID NO: 66, and wherein the LCDRs individually comprise between 0 to 1 substitution; and
   (c) a mutated Interleukin 2 (IL2) molecule engrafted into HCDR1, wherein the HCDR1 comprises SEQ ID NO: 7, SEQ ID NO: 10, SEQ ID NO: 13, SEQ ID NO: 16, SEQ ID NO: 39, SEQ ID NO: 42, SEQ ID NO: 45, or SEQ ID NO: 48, and wherein the mutated IL2 molecule contains a mutation that reduces the affinity of the mutated IL2 molecule to a high affinity IL2 receptor.

2. An antibody cytokine engrafted protein comprising:
   (a) an IgG class heavy chain comprising an IgG class heavy chain variable region (VH), comprising Complementarity Determining Regions (CDR) HCDR1 comprising SEQ ID NO: 7, SEQ ID NO: 10, SEQ ID NO: 13, SEQ ID NO: 16, SEQ ID NO: 39, SEQ ID NO: 42, SEQ ID NO: 45, or SEQ ID NO: 48, HCDR2 comprising SEQ ID NO: 8, SEQ ID NO: 11, SEQ ID NO: 14, SEQ ID NO: 17, SEQ ID NO: 40, SEQ ID NO: 46 or SEQ ID NO: 49, and HCDR3 comprising SEQ ID NO: 9, SEQ ID NO: 12, SEQ ID NO: 15, SEQ ID NO: 18, SEQ ID NO: 41, SEQ ID NO: 44, SEQ ID NO: 47 or SEQ ID NO: 50, and wherein the HCDRs individually comprise between 0 to 1 substitution; and
   (b) an IgG class light chain comprising an IgG class light chain variable region (VL), comprising LCDR1 comprising SEQ ID NO: 23, SEQ ID NO: 26, SEQ ID NO: 29, SEQ ID NO: 32, SEQ ID NO: 55, SEQ ID NO: 58, SEQ ID NO: 61 or SEQ ID NO: 64, LCDR2 comprising SEQ ID NO: SEQ ID NO: 24, SEQ ID NO: 27, SEQ ID NO: 30, SEQ ID NO: 33, SEQ ID NO: 56, SEQ ID NO: 59, SEQ ID NO: 62 or SEQ ID NO: 65, and LCDR3 comprising SEQ ID NO: 25, SEQ ID NO: 28, SEQ ID NO: 31, SEQ ID NO: 34, SEQ ID NO: 57, SEQ ID NO: 60, SEQ ID NO: 63 or SEQ ID NO: 66, and wherein the LCDRs individually comprise between 0 to 1 substitution, and a mutated Interleukin 2 (IL2) molecule engrafted into HCDR1, wherein the HCDR1 comprises SEQ ID NO: 7, SEQ ID NO: 10, SEQ ID NO: 13, SEQ ID NO: 16, SEQ ID NO: 39, SEQ ID NO: 42, SEQ ID NO: 45, or SEQ ID NO: 48, wherein the antibody cytokine engrafted protein preferentially expands T effector cells over regulatory T cells.

3. An antibody cytokine engrafted protein comprising:
(a) an IgG class heavy chain comprising an IgG class heavy chain variable region (VH), comprising Complementarity Determining Regions (CDR) HCDR1 comprising SEQ ID NO: 7, SEQ ID NO: 10, SEQ ID NO: 13, SEQ ID NO: 16, SEQ ID NO: 39, SEQ ID NO: 42, SEQ ID NO: 45, or SEQ ID NO: 48, HCDR2 comprising SEQ ID NO: 8, SEQ ID NO: 11, SEQ ID NO: 14, SEQ ID NO: 17, SEQ ID NO: 40, SEQ ID NO: 46 or SEQ ID NO: 49, and HCDR3 comprising SEQ ID NO: 9, SEQ ID NO: 12, SEQ ID NO: 15, SEQ ID NO: 18, SEQ ID NO: 41, SEQ ID NO: 44, SEQ ID NO: 47 or SEQ ID NO: 50, and wherein the HCDRs individually comprise between 0 to 1 substitution; and
(b) an IgG class light chain comprising an IgG class light chain variable region (VL), comprising LCDR1 comprising SEQ ID NO: 23, SEQ ID NO: 26, SEQ ID NO: 29, SEQ ID NO: 32, SEQ ID NO: 55, SEQ ID NO: 58, SEQ ID NO: 61 or SEQ ID NO: 64, LCDR2 comprising SEQ ID NO: SEQ ID NO: 24, SEQ ID NO: 27, SEQ ID NO: 30, SEQ ID NO: 33, SEQ ID NO: 56, SEQ ID NO: 59, SEQ ID NO: 62 or SEQ ID NO: 65, and LCDR3 comprising SEQ ID NO: 25, SEQ ID NO: 28, SEQ ID NO: 31, SEQ ID NO: 34, SEQ ID NO: 57, SEQ ID NO: 60, SEQ ID NO: 63 or SEQ ID NO: 66, and wherein the LCDRs individually comprise between 0 to 1 substitution; and
(c) a mutated Interleukin 2 (IL2) molecule engrafted into HCDR1, wherein the HCDR1 comprises SEQ ID NO: 7, SEQ ID NO: 10, SEQ ID NO: 13, SEQ ID NO: 16, SEQ ID NO: 39, SEQ ID NO: 42, SEQ ID NO: 45, or SEQ ID NO: 48;
wherein the antibody cytokine engrafted protein stimulates one or more of CD8$^+$ T effector cell proliferation, natural killer (NK) cell proliferation or combination thereof, greater than recombinant IL2 or aldesleukin.

4. The antibody cytokine engrafted protein of claim 1, wherein the VH comprises SEQ ID NO: 19 or SEQ ID NO: 51.

5. The antibody cytokine engrafted protein of claim 1, wherein the VL comprises SEQ ID NO: 35, or SEQ ID NO: 67.

6. The antibody cytokine engrafted protein of claim 1, wherein the IgG class heavy chain is selected from IgG1, IgG2, and IgG4.

7. The antibody cytokine engrafted protein of claim 1, wherein the IgG class heavy chain comprises SEQ ID NO: 21 or SEQ ID NO: 53.

8. The antibody cytokine engrafted protein of claim 1, wherein the IgG class light chain comprises SEQ ID NO:69 and the IgG class heavy chain comprises SEQ ID NO:53.

9. The antibody cytokine engrafted protein of claim 1, wherein the IgG class light chain comprises SEQ ID NO:37 and the IgG class heavy chain comprises SEQ ID NO:21.

10. The antibody cytokine engrafted protein of claim 1, wherein the IgG class light chain comprises SEQ ID NO:69 and the IgG class heavy chain comprises SEQ ID NO:21.

11. The antibody cytokine engrafted protein of claim 1, wherein the IgG class light chain comprises SEQ ID NO:37 and the IgG class heavy chain comprises SEQ ID NO:53.

12. The antibody cytokine engrafted protein of claim 1, wherein the IgG class light chain comprises 95% or more sequence identity with SEQ ID NO:37 and the IgG class heavy chain comprises 95% or more sequence identity with SEQ ID NO:21.

13. A method of treating cancer in an individual in need thereof, comprising administering to the individual a therapeutically effective amount of the antibody cytokine engrafted protein of claim 1.

14. The method of claim 13, wherein the cancer is selected from the group consisting of melanoma, lung cancer, colorectal cancer, prostate cancer, breast cancer, and lymphoma.

15. The method of claim 13, wherein the antibody cytokine engrafted protein is administered in combination with a therapeutic agent.

16. The method of claim 15, wherein the therapeutic agent is a second antibody cytokine engrafted protein.

17. The method of claim 15, wherein the therapeutic agent is an immune checkpoint inhibitor.

18. The method of claim 17, wherein the immune checkpoint is selected from the group consisting of: PD-1, PD-L1, PD-L2, TIM3, CTLA-4, LAG-3, CEACAM-1, CEACAM-5, VISTA, BTLA, TIGIT, LAIR1, CD160, 2B4 and TGFR.

19. The method of claim 15, wherein the therapeutic agent is a tyrosine kinase inhibitor.

20. A pharmaceutical composition comprising the antibody cytokine engrafted protein of claim 1 and a pharmaceutically acceptable carrier.

21. A method of treating cancer in an individual in need thereof, comprising administering to the individual a therapeutically effective amount of the pharmaceutical composition of claim 20.

22. The method of claim 21, wherein the cancer is selected from the group consisting of melanoma, lung cancer, colorectal cancer, prostate cancer, breast cancer, and lymphoma.

23. The method of claim 21, wherein the pharmaceutical composition is administered in combination with a therapeutic agent.

24. The method of claim 23, wherein the therapeutic agent is a second antibody cytokine engrafted protein.

25. The method of claim 23, wherein the therapeutic agent is an immune checkpoint inhibitor.

26. The method of claim 25, wherein the immune checkpoint is selected from the group consisting of: PD-1, PD-L1, PD-L2, TIM3, CTLA-4, LAG-3, CEACAM-1,CEACAM-5, VISTA, BTLA, TIGIT, LAIR1, CD160, 2B4 and TGFR.

27. The method of claim 23, wherein the therapeutic agent is a tyrosine kinase inhibitor.

* * * * *

UNITED STATES PATENT AND TRADEMARK OFFICE
CERTIFICATE OF CORRECTION

| | |
|---|---|
| PATENT NO. | : 12,006,354 B2 |
| APPLICATION NO. | : 16/616318 |
| DATED | : June 11, 2024 |
| INVENTOR(S) | : Deane et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 420 days.

Signed and Sealed this
Twenty-second Day of April, 2025

Coke Morgan Stewart
*Acting Director of the United States Patent and Trademark Office*